US009718760B2

(12) United States Patent
Lawrence et al.

(10) Patent No.: US 9,718,760 B2
(45) Date of Patent: Aug. 1, 2017

(54) PLASMINOGEN ACTIVATOR INHIBITOR-1 INHIBITORS AND METHODS OF USE THEREOF

(71) Applicants: THE REGENTS OF THE UNIVERSITY OF MICHIGAN, Ann Arbor, MI (US); EASTERN MICHIGAN UNIVERSITY, Ypsilanti, MI (US)

(72) Inventors: Daniel A. Lawrence, Ann Arbor, MI (US); Cory Emal, Ann Arbor, MI (US); Ashley Reinke, Ann Arbor, MI (US); Shih-Hon Li, Ypsilanti, MI (US); Mark Warnock, Brighton, MI (US); Gregory Abernathy, Dublin, OH (US)

(73) Assignees: THE REGENTS OF THE UNIVERSITY OF MICHIGAN, Ann Arbor, MI (US); EASTERN MICHIGAN UNIVERSITY, Ypsilanti, MI (US)

( * ) Notice: Subject to any disclaimer, the term of this patent is extended or adjusted under 35 U.S.C. 154(b) by 0 days.

(21) Appl. No.: 14/439,843

(22) PCT Filed: Oct. 31, 2013

(86) PCT No.: PCT/US2013/067695
§ 371 (c)(1),
(2) Date: Apr. 30, 2015

(87) PCT Pub. No.: WO2014/070983
PCT Pub. Date: May 8, 2014

(65) Prior Publication Data
US 2015/0315178 A1 Nov. 5, 2015

Related U.S. Application Data

(60) Provisional application No. 61/720,838, filed on Oct. 31, 2012.

(51) Int. Cl.
| | |
|---|---|
| *C07C 243/26* | (2006.01) |
| *C07C 69/84* | (2006.01) |
| *C07C 259/06* | (2006.01) |
| *C07C 271/16* | (2006.01) |
| *C07C 275/64* | (2006.01) |
| *C07C 311/17* | (2006.01) |
| *C07C 311/29* | (2006.01) |
| *C07C 311/48* | (2006.01) |
| *C07C 311/49* | (2006.01) |
| *C07D 417/04* | (2006.01) |
| *C07C 323/60* | (2006.01) |
| *C07D 249/08* | (2006.01) |
| *C07C 233/13* | (2006.01) |
| *C07C 233/56* | (2006.01) |
| *C07D 261/18* | (2006.01) |
| *C07C 235/34* | (2006.01) |
| *C07C 235/46* | (2006.01) |
| *C07D 271/113* | (2006.01) |
| *C07D 277/34* | (2006.01) |
| *C07D 207/48* | (2006.01) |
| *C07C 251/76* | (2006.01) |
| *C07D 209/08* | (2006.01) |
| *C07D 209/34* | (2006.01) |
| *C07D 213/42* | (2006.01) |

(52) U.S. Cl.
CPC ............ *C07C 69/84* (2013.01); *C07C 233/13* (2013.01); *C07C 233/56* (2013.01); *C07C 235/34* (2013.01); *C07C 235/46* (2013.01); *C07C 243/26* (2013.01); *C07C 251/76* (2013.01); *C07C 259/06* (2013.01); *C07C 271/16* (2013.01); *C07C 275/64* (2013.01); *C07C 311/17* (2013.01); *C07C 311/29* (2013.01); *C07C 311/48* (2013.01); *C07C 311/49* (2013.01); *C07C 323/60* (2013.01); *C07D 207/48* (2013.01); *C07D 209/08* (2013.01); *C07D 209/34* (2013.01); *C07D 213/42* (2013.01); *C07D 249/08* (2013.01); *C07D 261/18* (2013.01); *C07D 271/113* (2013.01); *C07D 277/34* (2013.01); *C07D 417/04* (2013.01)

(58) Field of Classification Search
CPC ...... C07C 233/56; C07C 69/84; C07C 243/26
See application file for complete search history.

(56) References Cited

U.S. PATENT DOCUMENTS

| | | | |
|---|---|---|---|
| 4,618,692 | A | 10/1986 | Scheffler et al. |
| 6,528,655 | B1 | 3/2003 | N'Zemba et al. |

(Continued)

FOREIGN PATENT DOCUMENTS

| | | |
|---|---|---|
| CN | 101351495 A | 1/2009 |
| EP | 0555893 A1 | 8/1993 |

(Continued)

OTHER PUBLICATIONS

Petyunin et al, 1964, CAPLUS Record DN 60:60623, p. 1.*

(Continued)

*Primary Examiner* — Rebecca Anderson
*Assistant Examiner* — Karen Cheng
(74) *Attorney, Agent, or Firm* — Marshall, Gerstein & Borun LLP

(57) ABSTRACT

The invention relates to plasminogen activator-1 (PAI-1) inhibitor compounds and uses thereof in the treatment of any disease or disorder associated with elevated PAI-1. The invention includes, but is not limited to, the use of such compounds to prevent or reduce thrombosis and fibrosis, to promote thrombolysis, and to modulate lipid metabolism and treat diseases or disorders associated with elevated PAI-1, cholesterol, or lipid levels.

12 Claims, No Drawings

(56) References Cited

U.S. PATENT DOCUMENTS

| | | | |
|---|---|---|---|
| 7,351,730 | B2 | 4/2008 | Mayer et al. |
| 8,759,327 | B2 | 6/2014 | Lawrence et al. |
| 9,120,744 | B2 | 9/2015 | Lawrence et al. |
| 2002/0052513 | A1 | 5/2002 | Broadhurst et al. |
| 2005/0124664 | A1 | 6/2005 | Sartori et al. |
| 2006/0058243 | A1 | 3/2006 | Chen et al. |
| 2007/0155747 | A1 | 7/2007 | Dasse et al. |
| 2010/0137194 | A1 | 6/2010 | Lawrence et al. |

FOREIGN PATENT DOCUMENTS

| | | | |
|---|---|---|---|
| EP | 1124157 | A2 | 8/2001 |
| EP | 1719763 | A1 | 11/2006 |
| JP | 2000-171937 | * | 6/2000 |
| WO | WO-92/00968 | A1 | 1/1992 |
| WO | WO-94/29267 | A1 | 12/1994 |
| WO | WO-99/42435 | A2 | 8/1999 |
| WO | WO-03/055843 | A1 | 7/2003 |
| WO | WO-2005/000330 | A1 | 1/2005 |
| WO | WO-2007/127505 | A2 | 11/2007 |
| WO | WO-2009/017848 | A1 | 2/2009 |

OTHER PUBLICATIONS

Alessi et al., Production of plasminogen activator inhibitor 1 by human adipose tissue: possible link between visceral fat accumulation and vascular disease. Diabetes. 46: 860-7 (1997).

Berkenpas et al., Molecular evolution of plasminogen activator inhibitor-1 functional stability. EMBO J. 14: 2969-77 (1995).

Biemond, Thrombolysis and reocclusion in experimental jugular vein and coronary artery thrombosis. Effects of a plasminogen activator inhibitor type 1-neutralizing monoclonal antibody. Circulation. 91: 1175 (1995).

Boncoraglio et al., An effect of the PAI-1 4G/5G polymorphism on cholesterol levels may explain conflicting assoc iatations with myocardial infarction and stroke. *Cerebrovascular Dis.* 22(2-3): 191-5 (2006).

Booth, Fibrinolysis and thrombosis. Baillieres Best. Pract. Res. Clin. Haematol. 12: 423-33 (1999).

Boucher et al., LRP: role in vascular wall integrity and protection from atherosclerosis. Science. 300: 329-32 (2003).

Bu, Receptor-associated protein: a specialized chaperone and antagonist for members of the LDL receptor gene family. Curr. Opin. Lipidol. 9: 149-55 (1998).

Butenas et al., Ultrasensitive fluorogenic substrates for serine proteases. Thromb. Haemost. 78: 1193-1201 (1997).

Cao et al., A specific role of integrin Mac-1 in accelerated macrophage efflux to the lymphatics. Blood. 106: 3234-41 (2005).

Cao et al., Endocytic receptor LRP together with tPA and PAI-1 coordinates Mac-1-dependent macrophage migration. EMBO J. 25: 1860-70 (2006).

Chen et al., 4G/5G promoter polymorphism of plasminogen activator inhibitor-1, lipid profiles, and ischemic stroke. *J. Lab. Clin. Med.* 142(2): 100-5 (2003).

Chmielewska et al., Evidence for a rapid inhibitor to tissue plasminogen activator in plasma. Thromb. Res. 31: 427-36 (1983).

Cigolini et al., Expression of plasminogen activator inhibitor-1 in human adipose tissue: a role for TNF-alpha? Atherosclerosis. 143: 81-90 (1999).

Clausen et al., Conditional gene targeting in macrophages and granulocytes using LysMcre mice. Transgenic Res. 8: 265-77 (1999).

Colucci et al., Generation in plasma of a fast-acting inhibitor of plasminogen activator in response to endotoxin stimulation. J. Clin. Invest. 75: 818-24 (1985).

Crandall et al., Characterization and comparative evaluation of a structurally unique PAI-1 inhibitor exhibiting oral in-vivo efficacy. J. Thromb. Haemost. 2: 1422-1428 (2004).

Crandall et al., Modulation of adipose tissue development by pharmacological inhibition of PAI-1. Arterioscler. Thromb. Vasc. Biol. 26: 2209-15 (2006).

Crandall et al., Release of PAI-1 by human preadipocytes and adipocytes independent of insulin and IGF-1. Biochem. Biophys. Res. Commun. 279: 984-8 (2000).

Cuchel et al., Macrophage reverse cholesterol transport: key to the regression of atherosclerosis? Circulation. 113: 2548-55 (2006).

Czekay et al., Plasminogen activator inhibitor-1 detaches cells from extracellular matrices by inactivating integrins. J. Cell. Biol. 160: 781-91 (2003).

Daci et al., Mice lacking the plasminogen activator inhibitor 1 are protected from trabecular bone loss induced by estrogen deficiency. J. Bone Miner. Res. 15: 1510-6. (2000).

De Taeye et al., Plasminogen activator inhibitor-1: a common denominator in obesity, diabetes and cardiovascular disease. Curr. Opin. Pharmacol. 5: 149-54 (2005).

De Taeye et al., Bone marrow plasminogen activator inhibitor-1 influences the development of obesity. J. Biol. Chem. 281: 32796-805 (2006).

Deng et al., Is plasminogen activator inhibitor-1 the molecular switch that governs urokinase receptor-mediated cell adhesion and release? J. Cell. Biol. 134: 1563-71 (1996).

Dichtl et al., In vivo stimulation by vascular plasminogen activator inhibitor-1 production by very low-density lipoprotein involves transcription factor binding to a VLDL-responsive element. *Thrombosis Haemastasis*, 84(4): 706-11 (2000).

Durand et al., Plasminogen activator inhibitor-I and tumour growth, invasion, and metastasis. Thromb. Haemost. 91: 438-49 (2004).

van Eck et al., Role of the macrophage very-low-density lipoprotein receptor in atherosclerotic lesion development. Artherosclerosis. 183: 230-7 (2005).

Ehrlich et al., Elucidation of structural requirements on plasminogen activator inhibitor 1 for binding to heparin. J. Biol. Chem. 267: 11606-11 (1992).

Eitzman et al., Bleomycin-induced pulmonary fibrosis in transgenic mice that either lack or overexpress the murine plasminogen activator inhibitor-1 gene. J. Clin. Invest. 97: 232-7 (1996).

Eitzman et al., Lack of plasminogen activator inhibitor-1 effect in a transgenic mouse model of metastatic melanoma. Blood. 87: 4718-22 (1996).

Elokdah et al., Tiplaxtinin, a novel, orally efficacious inhibitor of plasminogen activator inhibitor-1: design, synthesis, and preclinical characterization. J. Med. Chem. 47: 3491-4 (2004).

Erickson et al., Detection and partial characterization of an inhibitor of plasminogen activator in human platelets. J. Clin. Invest. 74: 1465-72 (1984).

Farkas et al., The recycling of apolipoprotein E in primary cultures of mouse hepatocytes. Evidence for a physiologic connection to high density lipoprotein metabolism. J. Biol. Chem. 278: 9412-7 (2003).

Fay et al., Brief report: complete deficiency of plasminogen-activator inhibitor type 1 due to a frame-shift mutation. N. Engl. J. Med. 327: 1729-33 (1992).

Fay et al., Platelets inhibit fibrinolysis in vitro by both plasminogen activator inhibitor-1-dependent and -independent mechanisms. Blood. 83: 351-6 (1994).

Gaitatzis et al., Novel insights into siderophore formation in myxobacteria. *ChemBioChem*, 6:365-74 (2005).

Giltay et al., Visceral fat accumulation is an important determinant of PAI-1 levels in young, nonobese men and women: modulation by cross-sex hormone administration. Arterioscler. Thromb. Vasc. Biol. 18: 1716-22 (1998).

Gorlatova et al., Mechanism of inactivation of plasminogen activator inhibitor-1 by a small molecule inhibitor. J. Biol. Chem. 282: 9288-96 (2007).

Gottschling-Zeller et al., Troglitazone reduces plasminogen activator inhibitor-1 expression and secretion in cultured human adipocytes. Diabetologia. 43: 377-83 (2000).

Hagglof et al., The reactive-center loop of active PAI-1 is folded close to the protein core and can be partially inserted. J. Mol. Biol. 335: 823-32 (2004).

Hamsten et al., Increased plasma levels of a rapid inhibitor of tissue plasminogen activator in young survivors of myocardial infarction. N. Engl. J. Med. 313: 1557-63 (1985).

Hasty et al., The recycling of apolipoprotein E in macrophages: influence of HDL and apolipoprotein A-I. Lipid Res. 46: 1433-9 (2005).

Heeren et al., Recycling of apoprotein E is associated with cholesterol efflux and high density lipoprotein internalization. J. Biol. Chem. 278: 14370-8 (2003).

Hekman et al., Bovine plasminogen activator inhibitor 1: specificity determinations and comparison of the active, latent, and guanidine-activated forms. Biochemistry. 27: 2911-8 (1988).

Hekman et al., Endothelial cells produce a latent inhibitor of plasminogen activators that can be activated by denaturants. J. Biol. Chem. 260: 11581-7 (1985).

Hennan et al., Evaluation of PAI-039 [{1-benzyl-5[4-(trifluoromethoxy)phenyl]-1H-indol-3-yl}(oxo)acetic acid], a novel plasminogen activator inhibitor-1 inhibitor, in a canine model of coronary artery thrombosis. J. Pharmacol. Exp. Ther. 314: 710-6 (2005).

Herz et al., LDL receptor-related protein internalizes and degrades uPA-PAI-1 complexes and is essential for embryo implantation. Cell. 71: 411-21 (1992).

Horn et al., Plasminogen activator inhibitor 1 contains a cryptic high affinity receptor binding site that is exposed upon complex formation with tissue-type plasminogen activator. Thromb. Haemost. 80: 822-8 (1998).

Huber et al., Implications of the three-dimensional structure of alpha 1-antitrypsin for structure and function of serpins. Biochemistry. 28: 8951-66 (1989).

Huber et al., Plasminogen activator inhibitor type-1 (part one): basic mechanisms, regulation, and role for thromboembolic disease. J. Thromb. Thrombolysis. 11: 183-93 (2001).

Huntington et al., Structure of a serpin-protease complex shows inhibition by deformation. Nature. 407: 923-6 (2000).

Huntington et al., The serpins: nature's molecular mousetraps. Sci. Prog. 84: 125-36 (2001).

Hussain et al., The mammalian low-density lipoprotein receptor family. Annu. Rev. Nutr. 19: 141-72 (1999).

International Preliminary Report on Patentability, International Application No. PCT/US2013/067695, May 5, 2015.

International Preliminary Report on Patentability, International Application No. PCT/US2008/60542, dated Oct. 20, 2009.

International Search Report and Written Opinion of the International Searching Authority, European Patent Office, PCT/US2008/60542, dated Nov. 21, 2008.

International Search Report and Written Opinion, International Application No. PCT/US2013/067695, mailed Apr. 4, 2014.

Jensen et al., Inhibition of plasminogen activator inhibitor-1 binding to endocytosis receptors of the low-density-lipoprotein receptor family by a peptide isolated from a phage display library. *Biochem. J.* 399(3): 387-96 (2006).

Jensen et al., The vitronectin binding area of plasminogen activator inhibitor-1, mapped by mutagenesis and protection against an inactivating organochemical ligand. FEBS Lett. 521: 91-4 (2002).

Kannel, Overview of hemostatic factors involved in atherosclerotic cardiovascular disease. Lipids. 40: 1215-20 (2005).

Kazi et al., Structure-activity relationships of synthetic analogs of (-)-epigallocatechin-3-gallate as proteasome inhibitors, Anticancer Research, 24:943-54 (2004).

Keijer et al., On the target specificity of plasminogen activator inhibitor 1: the role of heparin, vitronectin, and the reactive site. Blood. 78: 1254-61 (1991).

Kockx et al., Apolipoprotein A-I-stimulated apolipoprotein E secretion from human macrophages is independent of cholesterol efflux. J. Biol. Chem. 279: 25966-77 (2004).

Kohler et al., Plasminogen-activator inhibitor type 1 and coronary artery disease. N. Engl. J. Med. 342: 1792-1801 (2000).

Krieger et al., Scavenger receptor class B type I is a multiligand HDL receptor that influences diverse physiologic systems. J. Clin. Invest. 108: 793-7 (2001).

Krishnamurti et al., Plasminogen activator inhibitor: a regulator of ancrod-induced fibrin deposition in rabbits. et al., Blood. 69: 798 (1987).

Lambers et al., Activation of human endothelial cell-type plasminogen activator inhibitor (PAI-1) by negatively charged phospholipids. J. Biol. Chem. 262: 17492-6 (1987).

Lawrence et al., Characterization of the binding of different conformational forms of plasminogen activator inhibitor-1 to vitronectin. Implications for the regulation of pericellular proteolysis. J. Biol. Chem. 272: 7676-80 (1997).

Lawrence et al., Engineering plasminogen activator inhibitor 1 mutants with increased functional stability. Biochemistry. 33: 3643-8 (1994).

Lawrence et al., Inactivation of plasminogen activator inhibitor by oxidants. Biochemistry. 25: 6351-5 (1986).

Lawrence et al., Localization of vitronectin binding domain in plasminogen activator inhibitor-1. J. Biol. Chem. 269: 15223-8 (1994).

Lawrence et al., Molecular Basis of Thrombosis and Hemostasis, Marcel Dekker Inc., New York, 517-43 (1995).

Lawrence et al., Partitioning of serpin-proteinase reactions between stable inhibition and substrate cleavage is regulated by the rate of serpin reactive center loop insertion into beta-sheet A. J. Biol. Chem. 275: 5839-44 (2000).

Lawrence et al., Purification of active human plasminogen activator inhibitor 1 from *Escherichia coli*. Comparison with natural and recombinant forms purified from eucaryotic cells. Eur. J. Biochem. 186: 523-33 (1989).

Lawrence et al., Serpin reactive center loop mobility is required for inhibitor function but not for enzyme recognition. J. Biol. Chem. 269: 27657-62 (1994).

Lawrence et al., Serpin-protease complexes are trapped as stable acyl-enzyme intermediates. J. Biol. Chem. 270: 25309-12 (1995).

Lawrence et al., Structure-function studies of the SERPIN plasminogen activator inhibitor type 1. Analysis of chimeric strained loop mutants. J. Biol. Chem. 265: 20293-301 (1990).

Le Lay et al., Regulation of ABCA1 expression and cholesterol efflux during adipose differentiation of 3T3-L1 cells. J. Lipid Res. 44: 1499-1507 (2003).

Levi, Inhibition of plasminogen activator inhibitor-1 activity results in promotion of endogenous thrombolysis and inhibition of thrombus extension in models of experimental thrombosis. Circulation. 85: 305-12 (1992).

Levin et al., Conversion of the active to latent plasminogen activator inhibitor from human endothelial cells. Blood. 70: 1090-8 (1987).

Liang et al., Plasminogen activator inhibitor-1 modulates adipocyte differentiation. Am. J. Physiol. Endocrinol. Metab. 290: E103-13 (2006).

Lijnen et al., On the role of plasminogen activator inhibitor-1 in adipose tissue development and insulin resistance in mice. J. Thromb. Haemost. 3: 1174-9 (2005).

Lindahl et al., Stability of plasminogen activator inhibitor 1 (PAI-1). Thromb. Haemost. 62: 748-51 (1989).

Liu et al., Highly purified scavenger receptor class B, type I reconstituted into phosphatidylcholine/cholesterol liposomes mediates high affinity high density lipoprotein binding and selective lipid uptake. J. Biol. Chem. 277: 34125-35 (2002).

Lopes et al., PAI-1 polymorphisms modulate phenotypes associated with the metabolic syndrome in obese and diabetic Caucasian population. *Diabetologia*. 46(9): 1284-90 (2003).

Loskutoff et al., Detection of an unusually stable fibrinolytic inhibitor produced by bovine endothelial cells. Proc. Natl. Acad. Sci. USA. 80: 2956-60 (1983).

Loskutoff et al., The adipocyte and hemostatic balance in obesity: studies of PAI-1. Arterioscler. Thromb. Vasc. Biol. 18: 1-6 (1998).

Lundgren et al., Elaboration of type-1 plasminogen activator inhibitor from adipocytes. A potential pathogenetic link between obesity and cardiovascular disease. Circulation. 93: 106-10 (1996).

Lupu et al., Localization and production of plasminogen activator inhibitor-1 in human healthy and atherosclerotic arteries. Arterioscler. Thromb. 13: 1090-1100 (1993).

Ma et al., Prevention of obesity and insulin resistance in mice lacking plasminogen activator inhibitor 1. Diabetes. 53: 336-46 (2004).

Mavri et al., Impact of adipose tissue on plasma plasminogen activator inhibitor-1 in dieting obese women. Arterioscler. Thromb. Vasc. Biol. 19: 1582-7 (1999).

Minor et al., Plasminogen activator inhibitor type 1 promotes the self-association of vitronectin into complexes exhibiting altered incorporation into the extracellular matrix. J. Biol. Chem. 277: 10337-45 (2002).

Morange et al., Glucocorticoids and insulin promote plasminogen activator inhibitor 1 production by human adipose tissue. Diabetes. 48: 890-5 (1999).

Mottonen et al., Structural basis of latency in plasminogen activator inhibitor-1. Nature. 355: 270-3 (1992).

Naski et al., Kinetics of inactivation of alpha-thrombin by plasminogen activator inhibitor-1. Comparison of the effects of native and urea-treated forms of vitronectin. J. Biol. Chem. 268: 12367-72 (1993).

Nilsson et al., VLDL activation of plasminogen activator inhibitor-1 (PAI-1) expression: Involvement of the VLDL receptor. *J. Lipid Res.* 40(5): 913-9 (1999).

Nordt, Differential regulation by troglitazone of plasminogen activator inhibitor type 1 in human hepatic and vascular cells. J. Clin. Endocrin. Metabol. 85: 1563-8 (2000).

Ny et al., Cloning and sequence of a cDNA coding for the human beta-migrating endothelial-cell-type plasminogen activator inhibitor. Proc. Natl. Acad. Sci. USA. 83: 6776-80 (1986).

Ohashi et al., Reverse cholesterol transport and cholesterol efflux in atherosclerosis. QJM. 98: 845-56 (2005).

Podor et al., Incorporation of vitronectin into fibrin clots. Evidence for a binding interaction between vitronectin and gamma A/gamma' fibrinogen. J. Biol. Chem. 277: 7520-8 (2002).

Podor et al., New insights into the size and stoichiometry of the plasminogen activator inhibitor type-1.vitronectin complex. J. Biol. Chem. 275: 25402-10 (2000).

Podor et al., Type 1 plasminogen activator inhibitor binds to fibrin via vitronectin. J. Biol. Chem. 275: 19788-94 (2000).

PUBCHEM AKOS005831248—Compound Summary, pp. 1-3 (Jun. 18, 2007).

Reilly, Both circulating and clot-bound plasminogen activator inhibitor-1 inhibit endogenous fibrinolysis in the rat. Arterioscler. and Thromb.. 11: 1276 (1991).

Renckens et al., The role of plasminogen activator inhibitor type 1 in the inflammatory response to local tissue injury. J. Thromb. Haemost. 3: 1018-25 (2005).

Robbie et al., Inhibitors of fibrinolysis are elevated in atherosclerotic plaque. Arterioscler. Thromb. Vasc. Biol. 16: 539-45 (1996).

Rodenburg et al., Binding of urokinase-type plasminogen activator-plasminogen activator inhibitor-1 complex to the endocytosis receptors alpha2-macroglobulin receptor/low-density lipoprotein receptor-related protein and very-low-density lipoprotein receptor involved basic residues in the inhibitor. *Biochem. J.* 329(Part 1): 55-63 (1998).

Rohlmann et al., Inducible inactivation of hepatic LRP gene by cre-mediated recombination confirms role of LRP in clearance of chylomicron remnants. J. Clin. Invest. 101: 689-95 (1998).

Ross et al., Atherosclerosis—an inflammatory disease. N. Engl. J. Med. 340: 115-26 (1999).

Ruiz et al., The apoE isoform binding properties of the VLDL receptor reveal marked differences from LRP and the LDL receptor. J. Lipid Res. 46: 1721-31 (2005).

Sakamoto et al., TNF-alpha and insulin, alone and synergistically, induce plasminogen activator inhibitor-1 expression in adipocytes. Am. J. Physiol. 276: C1391-7 (1999).

Samad et al., Distribution and regulation of plasminogen activator inhibitor-1 in murine adipose tissue in vivo. Induction by tumor necrosis factor-alpha and lipopolysaccharide. J. Clin. Invest. 97: 37-46 (1996).

Samad et al., Tissue distribution and regulation of plasminogen activator inhibitor-1 in obese mice. Mol. Med. 2: 568-82 (1996).

Samad et al., Mol. Med. 2: 568-82 (1996).

Sawicki et al., A composite CMV-IE enhancer/beta-actin promoter is ubiquitously expressed in mouse cutaneous epithelium. Exp. Cell Res. 244: 367-9 (1998).

Schafer et al., Disruption of the plasminogen activator inhibitor 1 gene reduces the adiposity and improves the metabolic profile of genetically obese and diabetic ob/ob mice. FASEB J. 15: 1840-2 (2001).

Schneiderman et al., Increased type 1 plasminogen activator inhibitor gene expression in atherosclerotic human arteries. Proc. Natl. Acad. Sci. USA. 89: 6998-7002 (1992).

Seiffert et al., Constitutive and regulated expression of vitronectin. Histol. Histopathol. 12: 787-97 (1997).

Seiffert et al., The cell adhesion domain in plasma vitronectin is cryptic. J. Biol. Chem. 272: 13705-10 (1997).

Sharp et al., The active conformation of plasminogen activator inhibitor 1, a target for drugs to control fibrinolysis and cell adhesion. Structure. 7: 111-8 (1999).

Sherman et al., Saturation mutagenesis of the plasminogen activator inhibitor-1 reactive center. J. Biol. Chem. 267: 7588-95 (1992).

Shimomura et al., Enhanced expression of PAI-1 in visceral fat: possible contributor to vascular disease in obesity. Nat. Med. 2: 800-803 (1996).

Smith et al., Pivotal role of PAI-1 in a murine model of hepatic vein thrombosis. Blood. 107: 132-4 (2006).

Sprengers et al., Plasminogen activator inhibitors. Blood. 69: 381-7 (1987).

Stefansson et al., Inhibition of angiogenesis in vivo by plasminogen activator inhibitor-1. J. Biol. Chem. 276: 8135-41 (2001).

Stefansson et al., Mutants of plasminogen activator inhibitor-1 designed to inhibit neutrophil elastase and cathepsin G are more effective in vivo than their endogenous inhibitors. J. Biol. Chem. 279: 29981-7 (2004).

Stefansson et al., Old dogs and new tricks: proteases, inhibitors, and cell migration. Sci. STKE. 2003: pe24 (2003).

Stefansson et al., Plasminogen activator inhibitor-1 and vitronectin promote the cellular clearance of thrombin by low density lipoprotein receptor-related proteins 1 and 2. J. Biol. Chem. 271: 8215-20 (1996).

Stefansson et al., Plasminogen activator inhibitor-1 contains a cryptic high affinity binding site for the low density lipoprotein receptor-related protein. J. Biol. Chem. 273: 6358-66 (1998).

Stefansson et al., Plasminogen activator inhibitor-1 in tumor growth, angiogenesis and vascular remodeling. Curr. Pharm. Des. 9: 1545-64 (2003).

Stefansson et al., The serpin PAI-1 inhibits cell migration by blocking integrin alpha V beta 3 binding to vitronectin. Nature. 383: 441-3 (1996).

Stewart et al., Synthesis of 3-nitro-L-tyrosine peptides by means of active polyester intermediates derived from the nitrophenol side chain, Australian J. Chem. 3293:661-7 (1979).

Strandberg et al., The oxidative inactivation of plasminogen activator inhibitor type 1 results from a conformational change in the molecule and does not require the involvement of the P1' methionine. J. Biol. Chem. 266: 13852-8 (1991).

Suganami et al., A paracrine loop between adipocytes and macrophages aggravates inflammatory changes: role of free fatty acids and tumor necrosis factor alpha. Arterioscler. Thromb. Vasc. Biol. 25: 2062-8 (2005).

Takahashi et al., Purification and ATPase activity of human ABCA1. J. Biol. Chem. 281: 10760-8 (2006).

Takahashi et al., The very low density lipoprotein (VLDL) receptor—a peripheral lipoprotein receptor for remnant lipoproteins into fatty acid active tissues. Mol. Cell. Biochem. 248: 121-7 (2003).

Tomasini et al., Vitronectin. Prog. Hemost. Thromb. 10: 269-305 (1991).

Vague et al., Correlation between blood fibrinolytic activity, plasminogen activator inhibitor level, plasma insulin level, and relative body weight in normal and obese subjects. Metabolism. 35: 250-3 (1986).

van Mourik et al., Purification of an inhibitor of plasminogen activator (antiactivator) synthesized by endothelial cells. J. Biol. Chem. 259: 14914-21 (1984).

Vassiliou et al., A novel efflux-recapture process underlies the mechanism of high-density lipoprotein cholesteryl ester-selective uptake mediated by the low-density lipoprotein receptor-related protein. Arterioscler. Thromb. Vasc. Biol. 24: 1669-75 (2004).

Vaughan et al., Studies of recombinant plasminogen activator inhibitor-1 in rabbits. Pharmacokinetics and evidence for reactivation of latent plasminogen activator inhibitor-1 in vivo. Circ. Res. 67: 1281-6 (1990).

Vaughan, PAI-1 and atherothrombosis. J. Thromb. Haemost. 3: 1879-83 (2005).

Vezina et al., Apolipoprotein distribution in human lipoproteins separated by polyacrylamide gradient gel electrophoresis. J. Lipid Res. 29: 573-85 (1988).

Webb et al., Plasminogen activator inhibitor 1 functions as a urokinase response modifier at the level of cell signaling and thereby promotes MCF-7 cell growth. J. Cell. Biol. 152: 741-52 (2001).

Weisberg et al., Pharmacological inhibition and genetic deficiency of plasminogen activator inhibitor-1 attenuates angiotensin II/salt-induced aortic remodeling. Arterioscler. Thromb. Vasc. Biol. 25: 365-71 (2005).

Weiss et al., Neutrophils degrade subendothelial matrices in the presence of alpha-1-proteinase inhibitor. Cooperative use of lysosomal proteinases and oxygen metabolites. J. Clin. Invest. 73: 1297-1303 (1984).

Wilczynska et al., The inhibition mechanism of serpins. Evidence that the mobile reactive center loop is cleaved in the native protease-inhibitor complex. J. Biol. Chem. 270: 29652-5 (1995).

Xu et al., Apolipoproteins of HDL can directly mediate binding to the scavenger receptor SR-BI, an HDL receptor that mediates selective lipid uptake. J. Lipid Res. 38: 1289-98 (1997).

Xu et al., Conservation of critical functional domains in murine plasminogen activator inhibitor-1. J. Biol. Chem. 279: 17914-20 (2004).

Yepes et al., Plasminogen Activator Inhibitor-1, Hemostasis and Thrombosis: Basic Principles and Clinical Practice, Lippincott Williams & Wilkins, 365-80 (2006).

Zannis et al., Role of apoA-I, ABCA1, LCAT, and SR-BI in the biogenesis of HDL. J. Mol. Med. 84: 276-94 (2006).

Zhou et al., How vitronectin binds PAI-1 to modulate fibrinolysis and cell migration. Nat. Struct. Biol. 10: 541-4 (2003).

Ashton et al., Nonpeptide angiotensin II antagonists derived from 4H-1,2,4-triazoles and 3H-imidazo[1,2-b][1,2,4] triazoles, J. Med. Chem., 36(5):591-609 (1993).

Choi et al., Generation of oxamic acid libraries: antimalarials and inhibitors of Plasmodium falciparum lactate dehydrogenase, J. Comb. Chem., 9(2):292-300 (2007).

Hynes et al., Hydroxylamine derivatives as potential inhibitors of nucleic acid synthesis, J. Med. Chem., 16(5):576-8 (1973).

Supplemental Partial European Search Report, European application No. 13850232, mailed Jul. 6, 2016.

Extended European Search Report, European Patent Application No. 13850232.3, dated Oct. 10, 2016.

First Office Action (English translation), Chinese Patent Application No. 201380068795.3, dated Aug. 31, 2016.

STN Registry Database (accessed Aug. 8, 2016).

* cited by examiner

PLASMINOGEN ACTIVATOR INHIBITOR-1 INHIBITORS AND METHODS OF USE THEREOF

CROSS-REFERENCE TO RELATED APPLICATIONS

This application is the U.S. national phase of PCT/US2013/067695, filed Oct. 31, 2013, which claims the benefit of U.S. provisional application No. 61/720,838, filed Oct. 31, 2012.

GOVERNMENT RIGHTS

This invention was made in part with government support under grant number HL089407 from the National Institute of Health. As such, the United States government has certain rights in the invention.

FIELD OF THE INVENTION

The invention generally relates to methods and compositions for modulating plasminogen activator inhibitor-1 (PAI-1) activity. More particularly, the invention is directed to methods of identifying inhibitors of PAI-1 and the uses of such inhibitors in regulating PAI-1 activity. The invention also relates to uses of these inhibitors for the treatment of many diseases or disorders associated with PAI-1 activity. Such diseases or disorders include, but are not limited to, dysregulation of lipid metabolism, obesity, diabetes, polycystic ovary syndrome, bone loss induced by estrogen deficiency, fibrosis and fibrotic disease, inflammation, cell migration and migration-driven proliferation of cells, angiogenesis, and thrombosis. Such inhibitors are also contemplated to be useful for modulation of endogenous fibrinolysis, and in conjunction with pharmacologic thrombolysis.

BACKGROUND OF THE INVENTION

Plasminogen activator inhibitor-1 (PAI-1) is a 50 kDa single-chain glycoprotein that is the principal inhibitor of both urokinase type plasminogen activator (uPA) and tissue type PA (tPA). PAI-1 inhibits tPA and uPA with second-order rate constants $\sim 10^7$ $M^{-1}$ $s^{-1}$, a value that is 10-1000 times faster than the rates of PA inhibition by other PAIs. Moreover, approximately 70% of the total tPA in carefully collected normal human plasma is detected in complex with PAI-1, suggesting that inhibition of tPA by PAI-1 is a normal, ongoing process. PAI-1 can also directly inhibit plasmin. Thus, PAI-1 is the chief regulator of plasmin generation in vivo, and as such it appears to play an important role in both fibrotic and thrombotic disease. PAI-1 has three potential N-linked glycosylation sites and contains between 15 and 20% carbohydrate.

PAI-1 belongs to the Serine Protease Inhibitor super family (SERPIN), which is a gene family that includes many of the protease inhibitors found in blood, as well as other proteins with unrelated or unknown functions. Serpins are consumed in the process of protease inactivation and thus act as "suicide inhibitors." The association between a serpin and its target protease occurs at an amino acid residue, referred to as the "bait" residue, located on a surface loop of the serpin called the reactive center loop (RCL). The "bait" residue is also called the P1 residue, and is thought to mimic the normal substrate of the enzyme. Upon association of the P1 residue with the S1 site of a target protease, cleavage of the RCL occurs. This is coupled to a large conformational change in the serpin which involves rapid insertion of the RCL into the major structural feature of a serpin, β-sheet A. This results in tight docking of the protease to the serpin surface and to distortion of the enzyme structure, including its active site. RCL insertion also produces a large increase in serpin structural stability making the complex rigid and thus trapping the protease in a covalent acyl-enzyme complex with the serpin.

Native PAI-1 exists in at least two distinct conformations, an active form that is produced by cells and secreted, and an inactive or latent form that accumulates in cell culture medium over time. In blood and tissues, most of the PAI-1 is in the active form; however, in platelets both active and latent forms of PAI-1 are found. In active PAI-1, the RCL is exposed on the surface of the molecule, but upon reaction with a protease, the cleaved RCL integrates into the center of β sheet A. In the latent form, the RCL is intact, but instead of being exposed, the entire amino terminal side of the RCL is inserted as the central strand into the β sheet A. This accounts for the increased stability of latent PAI-1 as well as its lack of inhibitory activity.

Active PAI-1 spontaneously converts to the latent form with a half-life of one to two hours at 37° C., and latent PAI-1 can be converted back into the active form by treatment with denaturants. Negatively charged phospholipids can also convert latent PAI-1 to the active form, suggesting that cell surfaces may modulate PAI-1 activity. The observation that latent PAI-1 infused into rabbits is apparently converted to the active form is consistent with this hypothesis. The spontaneous reversible interconversion between the active and latent structures is unique for PAI-1 and distinguishes it from other serpins; however, the biological significance of the latent conformation remains unknown.

Other non-inhibitory forms of PAI-1 have also been identified. The first form results from oxidation of one or more critical methionine residues within active PAI-1. This form differs from latent PAI-1 in that it can be partially reactivated by an enzyme that specifically reduces oxidized methionine residues. Oxidative inactivation of PAI-1 may be an additional mechanism for the regulation of PAI-1, and oxygen radicals produced locally by neutrophils or other cells may inactivate PAI-1 and thus facilitate the generation of plasmin at sites of infection or in areas of tissue remodeling. PAI-1 also exists in two different cleaved forms. As noted above, PAI-1 in complex with a protease is cleaved in its RCL. Uncomplexed PAI-1 can also be found with its RCL cleaved, which can arise from dissociation of PAI-1-PA complexes or from cleavage of the RCL by a non-target protease at a site other than the P1. None of these forms of PAI-1 are able to inhibit protease activity; however, they may interact with other ligands.

The interaction of PAI-1 with non-protease ligands plays an essential role in PAI-1 function. PAI-1 binds with high affinity to heparin, the cell adhesion protein vitronectin, and members the endocytic low-density lipoprotein receptor (LDL-R) family, such as the lipoprotein receptor-related protein (LRP), and the very low density lipoprotein receptor (VLDL-R). These non-protease interactions are important for both PAI-1 localization and function, and they are largely conformationally controlled through structural changes associated with RCL insertion. In blood, most of the active PAI-1 circulates in complex with the glycoprotein vitronectin. The PAI-1 binding site for vitronectin has been localized to a region on the edge of β-sheet A in the PAI-1 structure. The binding site for LDL-R family members is less well characterized, but has been identified, in a region of PAI-1 associated with alpha helix D that is adjacent to the vitronectin binding domain. The heparin binding domain on PAI-1 has also been mapped. This site also localizes to alpha helix D in a region homologous to the heparin binding domain of antithrombin III, and may overlap with the binding site for LDL-R family members.

Vitronectin circulates in plasma and is present in the extracellular matrix primarily at sites of injury or remodeling. PAI-1 and vitronectin appear to have a significant functional interdependence. Vitronectin stabilizes PAI-1 in its active conformation, thereby increasing its biological half-life.

Vitronectin also enhances PAI-1 inhibitory efficiency for thrombin approximately 300-fold. In turn, PAI-1 binding to vitronectin alters its conformation from the native plasma form, which does not support cell adhesion, to an "activated" form that is competent to bind integrins. However, integrin binding is blocked by the presence of PAI-1. As noted above, the association of PAI-1 with vitronectin is conformationally controlled and upon inhibition of a protease, the conformational change in PAI-1 associated with RCL insertion results in a loss of high affinity for vitronectin and a gain in affinity for LDL-R family members. This is due to RCL insertion in PAI-1, disrupting the vitronectin binding site, while simultaneously exposing a cryptic receptor binding site that is revealed only when PAI-1 is in a complex with a protease, which results in an approximately 100,000-fold shift in the relative affinity of PAI-1 from vitronectin to LDL-R family members and a subsequent shift in PAI-1 localization from vitronectin to the cellular receptor. Thus, PAI-1 association with vitronectin and LDL-R is conformationally controlled.

High PAI-1 levels are associated with various diseases and disorders. For example, high PAI-1 levels are associated with acute diseases, such as sepsis and myocardial infarction, and chronic disorders, such as cancer, atherosclerosis, and type 2 diabetes. In addition, high PAI-1 levels are associated with cardiovascular disease, wherein PAI-1 expression is significantly increased in severely atherosclerotic vessels, and PAI-1 protein levels rise consistently during disease progression from normal vessels to fatty streaks to atherosclerotic plaques. Increased PAI-1 levels are also linked to obesity, and insulin resistance.

In addition, elevated plasma levels of PAI-1 have been associated with thrombotic events, and antibody neutralization of PAI-1 activity resulted in promotion of endogenous thrombolysis and reperfusion. Elevated levels of PAI-1 have also been implicated in polycystic ovary syndrome and bone loss induced by estrogen deficiency.

PAI-1 is synthesized in both murine and human adipocytes. There is also a strong correlation between the amount of visceral fat and plasma levels of PAI-1 in humans and mice. This dramatic up-regulation of PAI-1 in obesity has lead to the suggestion that adipose tissue itself may directly contribute to elevated systemic PAI-1, which in-turn increases the probability of vascular disease through increased thrombosis, and accelerated atherosclerosis. Notably, very recent data suggests that PAI-1 may also play a direct role in obesity.

In one study, genetically obese and diabetic ob/ob mice crossed into a PAI-1 deficient background had significantly reduced body weight and improved metabolic profiles compared to ob/ob mice with PAI-1. Likewise, nutritionally-induced obesity and insulin resistance were dramatically attenuated in mice genetically deficient in PAI-1 and in mice treated with an orally active PAI-1 inhibitor. The improved adiposity and insulin resistance in PAI-1-deficient mice may be related to the observation that PAI-1 deficient mice on a high fat diet had increased metabolic rates and total energy expenditure compared to wild-type mice, and peroxysome proliferator-activated receptor (PPARγ) and adiponectin were maintained. However, the precise mechanism involved was not shown and may be complex, since the overexpression of PAI-1 in mice also impaired adipose tissue formation. Taken together, these observations suggest that PAI-1 plays a previously unrecognized direct role in obesity and insulin resistance that involves interactions beyond its identified activities of modulating fibrinolysis and tissue remodeling.

Indeed, if PAI-1 positively regulates adipose tissue development, then the association of increased PAI-1 expression with developing obesity may constitute a positive feedback loop promoting adipose tissue expansion and dysregulation of normal cholesterol homeostasis. Thus, there exists a need in the art for a greater understanding of how PAI-1 is involved in metabolism, obesity and insulin resistance. The invention provides methods of identifying and using inhibitors of PAI-1.

SUMMARY OF THE INVENTION

The invention provides plasminogen activator inhibitor-1 (PAI-1) inhibitors and uses thereof in the treatment of any disease or disorder associated with elevated PAI-1 levels in a subject. Such uses include, but are not limited to, the treatment of many diseases or disorders associated with elevated PAI-1 levels or activity as discussed herein below. The invention further provides compositions comprising isolated PAI-1 inhibitors and a pharmaceutically acceptable carrier, wherein the PAI-1 inhibitors are present in an amount effective to inhibit PAI-1.

Such PAI-1 inhibitors include, but are not limited to, any of the compounds of Formulas I to XXIX or any of the compounds depicted in Tables 1, 3, 5, 7, 9, 11, 12, and 14, including C256, C259, C265, C267, C276, C277, C288, C309, C311, C280, C300, C313, C314, C320, C323, C326, C328, C334, C342, C240, C241, C246, C248, C251, C255, C260, C261, C262, C263, C264, C266, C268, C278, C281, C282, C287, C289, C295, C296, C297, C301, C304, C305, C307, C310, C322, C336, C339, C340, C341, C362, C279, C285, C286, C299, C306, C330, C344, C345, C346, C347, C348, C356, C357, C358, C359, C360, C361, C363, C364, C284, C152, C155, C173, C189, C191, C197, C224, C292, C293, C294, C153, C162, C163, C165, C188, C195, C157, C158, C182, C183, C170, C171, C172, C175, C177, C179, C180, C186, C193, C205, C160, C187, C190, C198, C232, C233, C249, C270, C271, C272, C273, C274, C275, C303, C210, C168, C176, C184, C185, C196, C156, C161, C200, C204, C236, C201, C208, C213, C216, C220, C221, C222, C223, C199, C207, C225, C227, C228, and C229 as set out herein.

In a further embodiment, methods of treating or preventing a disease or disorder associated with elevated levels of PAI-1 or elevated PAI-1 activity are provided. The methods comprise administering a PAI-1 inhibitor to the subject in an amount effective to treat the disease or disorder. In one aspect, the disease or disorder includes, but is not limited to, cancer, septicemia, a disorder associated with a dysregulation of lipid metabolism, a proliferative disease or disorder, psoriasis, fibrosis and fibrotic disease, coagulation homeostasis, cerebrovascular disease, vascular disease, microvascular disease, hypertension, dementia, atherosclerosis, osteoporosis, osteopenia, arthritis, asthma, heart failure, arrhythmia, angina, hormone insufficiency, Alzheimer's disease, inflammation, sepsis, fibrinolytic disorder, stroke, dementia, coronary heart disease, myocardial infarction, stable and unstable angina, peripheral arterial disease, acute vascular syndrome, thrombosis, prothrombosis, pulmonary embolism, insulin resistance, non-insulin dependent diabetes mellitus, Type 1 and 2 diabetes and related diabetic diseases, obesity, hyperglycemia, hyperinsulinemia, malignant lesions, premalignant lesions, gastrointestinal malignancies, liposarcoma, epithelial tumor, an extracellular matrix accumulation disorder, neoangiogenesis, myelofibrosis, fibrinolytic impairment, polycystic ovary syndrome, bone loss induced by estrogen deficiency, angiogenesis, neoangiogenesis, myelofibrosis, or fibrinolytic impairment.

In some aspects, the disease or disorder involving thrombosis or prothrombosis includes, but is not limited to, formation of atherosclerotic plaques, venous and/or arterial thrombosis, deep vein thrombosis, arterial thrombosis, myocardial ischemia, atrial fibrillation, deep vein thrombosis, a coagulation syndrome, pulmonary thrombosis, cerebral thrombosis, a thromboembolic complication of surgery, and peripheral arterial occlusion.

In some aspects, the disease or disorder involving microvascular disease includes, but is not limited to, nephropathy, neuropathy, retinopathy and nephrotic syndrome.

In some aspects, the disease or disorder involving fibrosis or an extracellular matrix accumulation includes, but is not limited to, renal fibrosis, chronic obstructive pulmonary disease, polycystic ovary syndrome, restenosis, renovascular disease, diabetic nephropathy, or organ transplant rejection.

In some aspects, the disease or disorder involving dysregulation of lipid metabolism includes, but is not limited to, high cholesterol, elevated triglycerides, elevated levels of VLDL or LDL, and low levels of HDL. In various aspects, therefore, the PAI-1 inhibitor compounds of the invention are used in methods of modulating cholesterol and/or lipid uptake and/or lipid clearance. In some aspects, the PAI-1 inhibitor compounds decrease PAI-1 binding to ApoE, ApoA, VLDL, VLDL-R, ApoA-R, or LDL. In yet another aspect, the PAI-1 inhibitor compounds bind to PAI-1 in the presence of vitronectin and/or uPA. In one aspect, the PAI-1 inhibitor is administered to a subject in an amount effective to inhibit VLDL or ApoE or ApoA binding to VLDL-R. In one aspect, the PAI-1 inhibitor is administered to a subject in an amount effective to affect HDL or ApoE or ApoA binding to an ApoA receptor. In particular aspects, the PAI-1 inhibitor is used to increase HDL and/or decrease VLDL in a subject.

In another embodiment, the PAI-1 inhibitor compounds of the invention are useful for modulation of endogenous fibrinolysis and for use in pharmacologic thrombolysis.

In some aspects, the subject is human.

Uses of compounds of the invention for the production of a medicament for the treatment or prevention of any disease or disorder discussed herein are also provided. The compounds of the invention are inhibitors of the serine protease inhibitor PAI-1, and are therefore useful in the treatment or prophylaxis of those processes which involve the production and/or action of PAI-1.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. Additional features and variations of the invention will be apparent to those skilled in the art from the entirety of this application, and all such features are intended as aspects of the invention.

DETAILED DESCRIPTION OF THE INVENTION

The invention describes materials and methods for the inhibition of plasminogen activator inhibitor-1 (PAI-1). In exemplary aspects, the invention describes PAI-1 inhibitor compounds.

PAI-1 Inhibitor Compounds of the Invention

As used herein, the term "haloalkyl" refers to a hydrocarbon group substituted with one or more halogens selected from F, Cl, Br, and I.

As used herein, the term "cycloalkyl" refers to a cyclic hydrocarbon group, e.g., cyclopropyl, cyclobutyl, cyclohexyl, cyclopentyl, cyclohexyl, cycloheptyl, and cyclooctyl. As used herein, the term "heterocycloalkyl" or "heterocyclic ring" refers to a cyclic hydrocarbon group having one or more heteroatoms, for example, one to three heteroatoms, independently selected from the group consisting of oxygen, nitrogen, and sulfur.

As used herein, the term "aryl" refers to a monocyclic or polycyclic aromatic group, preferably a monocyclic or bicyclic aromatic group. Unless otherwise indicated, an aryl group can be unsubstituted or substituted with one or more, and in particular one to four, groups independently selected from, for example, —OH, —OR (including —OCH$_3$), —F, —Cl, —Br, —I, —CF$_3$, —NO$_2$, —NO, —N(R)$_2$, —N(R)$_3^+$, —C(O)R, —C(O)OR, —CHO, —C(O)NH$_2$, —C(O)SR, —CN, —S(O)$_2$R, —SO$_3$R, —SO$_3$H, —SO$_2$N(R)$_2$, —S=O, aryl, and heteroaryl. Exemplary aryl groups include, but are not limited to, phenyl, tolyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or polycyclic ring system containing one or more aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, —OH, —OR (including —OCH$_3$), —F, —Cl, —Br, —I, —CF$_3$, —NO$_2$, —NO, —N(R)$_2$, —N(R)$_3^+$, —C(O)R, —C(O)OR, —CHO, —C(O)NH$_2$, —C(O)SR, —CN, —S(O)$_2$R, —SO$_3$R, —SO$_3$H, —SO$_2$N(R)$_2$, —S=O, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

As used herein, the term "substituted benzyl" refers to a benzyl group substituted with one or more, and in particular one to four, groups independently selected from, for example, —OH, —OR (including —OCH$_3$), —F, —Cl, —Br, —I, —CF$_3$, —NO$_2$, —NO, —N(R)$_2$, —N(R)$_3^+$, —C(O)R, —C(O)OR, —CHO, —C(O)NH$_2$, —C(O)SR, —CN, —S(O)$_2$R, —SO$_3$R, —SO$_3$H, —SO$_2$N(R)$_2$, —S=O, aryl, and heteroaryl.

As used herein, the term "amino acid" refers to naturally occurring and non-natural amino acids, as well as amino acid analogs. Naturally encoded amino acids include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), pyrrolysine, and selenocysteine. Amino acid analogs refers to compounds that have the same basic chemical structure as a naturally occurring amino acid, i.e., a carbon that is bound to a hydrogen, a carboxyl group, an amino group, and an R group, for example, 3-nitrotyrosine, homoserine, norleucine, methionine sulfoxide, methionine methyl sulfonium. Such analogs have modified R groups (such as 3-nitrotyrosine) or modified peptide backbones, but retain the same basic chemical structure as a naturally occurring amino acid. Amino acid analogs also include amino acid esters (e.g., amino acid alkyl esters, such as amino acid methyl esters) and acylated amino acids (e.g., acetylated amino acids).

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, prodrugs, salts of such prodrugs, or any other adduct or derivative which upon administration to a patient in need is capable of providing, directly or indirectly, a compound as otherwise described herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any salt or salt of an ester of a compound of this invention that, upon administration to a recipient, is capable of providing, either directly or indirectly, a compound of this invention.

Pharmaceutically acceptable salts are well known in the art. For example, S. M. Berge et al. describe pharmaceutically acceptable salts in detail in *J. Pharmaceutical Sciences*, 1977, 66, 1-19, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The term "prodrug" as used herein refers to compounds that are rapidly converted to an active form (i.e., drug) within the body or cells thereof by the action of endogenous enzymes or other chemicals and/or conditions. Prodrug design is discussed generally in Hardma et al. (Eds.), Goodman and Gilman's The Pharmacological Basis of Therapeutics, 9th ed., pp. 11-16 (1996). Prodrugs of the compounds disclosed herein include, but are not limited to, esters formed from available hydroxyl or carboxyl groups (also referred to as ester prodrugs or prodrug esters), amides formed from available amino, amido, or carboxyl groups, thioesters formed from available thiol or carboxyl groups, carbonates formed from available hydroxyl or carboxyl groups, carbamates formed from available hydroxyl, amino, or amido groups, carbamides formed from available amido or amino groups, sulfonate esters and sulfate esters formed from available hydroxyl groups, sulfonamides formed from available amino groups, and phosphonamides formed from available amino groups. Suitable ester prodrugs include, but are not limited to, aliphatic esters, aryl esters, benzyl esters, and derivatives thereof.

Compounds of the invention include those of formula I or a salt, ester, or prodrug thereof:

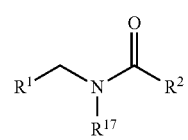

I wherein:

$R^1$ is selected from the group consisting of $C_1$ to $C_{12}$ alkyl, $-L^1-C_3-C_6$ cycloalkyl, $-L^2-C_2-C_6$ heterocycloalkyl, benzyl, $-L^3$-aryl, and $-L^4$-heteroaryl;

$R^2$ is selected from the group consisting of $-L^5-C(=O)R^3$, $-L^6-R^4$, and $NHR^5$;

$R^3$ is selected from the group consisting of $OR^6$, $NR^7R^8$, and $NHNHR^9$;

$R^5$ is selected from the group consisting of $OR^{10}$, $C_1$ to $C_{12}$ alkyl, $-L^7-C_3-C_6$ cycloalkyl, $-L^8-C_2-C_6$ heterocycloalkyl, benzyl, $-L^9$-aryl, and $-L^{10}$-heteroaryl;

$R^8$ is selected from the group consisting of $OR^{11}$, $N=R^{12}R^{13}$, $-L^{11}-R^{14}$, $NHSO_2R^{15}$, and $NHR^{16}$;

$R^6$, $R^7$, $R^9$, $R^{10}$, $R^{11}$, $R^{12}$, $R^{13}$, and $R^{17}$ are independently selected from the group consisting of H and $C_1$ to $C_{12}$ alkyl;

$R^4$, $R^{14}$, $R^{15}$, and $R^{16}$ are independently selected from the group consisting of -$L^{12}$-$C_3$-$C_6$ cycloalkyl, -$L^{13}$-$C_2$-$C_6$ heterocycloalkyl, benzyl, -$L^{14}$-aryl, and -$L^{15}$-heteroaryl; and $L^1$, $L^2$, $L^3$, $L^4$, $L^5$, $L^6$, $L^7$, $L^8$, $L^9$, $L^{10}$, $L^{11}$, $L^{12}$, $L^{13}$, $L^{14}$ and $L^{15}$ are independently selected from the group consisting of null, $C_1$ to $C_{12}$ alkylene, and $C_1$ to $C_{12}$ alkenylene.

Compounds of the invention include those of formula II or a salt, ester, or prodrug thereof:

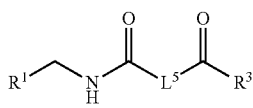

II wherein $R^1$, $L^5$, and $R^3$ are as defined above for formula I.

Compounds of the invention include those of formula III or a salt, ester, or prodrug thereof:

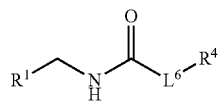

III wherein $R^1$, $L^6$, and $R^4$ are as defined above for formula I.

Compounds of the invention include those of formula IV or a salt, ester, or prodrug thereof:

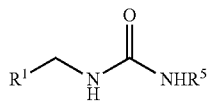

IV wherein $R^1$ and $R^5$ are as defined above for formula I.

Compounds of the invention include those of formula V or a salt, ester, or prodrug thereof:

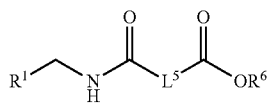

V wherein $R^1$, $L^5$, and $R^6$ are as defined above for formula I.

Compounds of the invention include those of formula VI or a salt, ester, or prodrug thereof:

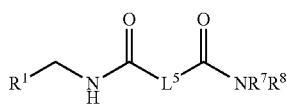

VI wherein $R^1$, $L^5$, $R^7$, and $R^8$ are as defined above for formula I.

Compounds of the invention include those of formula VII or a salt, ester, or prodrug thereof:

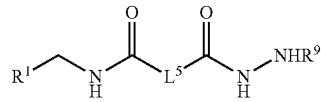

VII wherein $R^1$, $L^5$, and $R^9$ are as defined above for formula I.

In formulas I to VII, $R^1$ is selected from $C_1$ to $C_{12}$ alkyl, -$L^1$-$C_3$-$C_6$ cycloalkyl, -$L^2$-$C_2$-$C_6$ heterocycloalkyl, benzyl, -$L^3$-aryl, and -$L^4$-heteroaryl, and is optionally substituted with one, two, three, or more substituent groups that are the same or different. Suitable substituent groups include, but are not limited to, F, Cl, Br, I, $CF_3$, $CH_3$, $OCF_3$, $OCH_3$, and —CN. Additional $R^1$ groups include, but are not limited to, optionally substituted phenyl, halophenyl (e.g., fluorophenyl, chlorophenyl, bromophenyl, iodophenyl), dihalophenyl (e.g., difluorophenyl, dichlorophenyl, dibromophenyl, diiodophenyl), trihalophenyl (e.g., trifluorophenyl, trichlorophenyl, tribromophenyl, triiodophenyl), (trifluoromethyl)phenyl, fluoro(trifluoromethyl)phenyl, chloro(trifluoromethyl)phenyl, bromo(trifluoromethyl)phenyl, iodo(trifluoromethyl)phenyl, tolyl, xylyl, fluorotolyl, chlorotolyl, bromotolyl, iodotolyl, fluoroxylyl, chloroxylyl, bromoxylyl, iodoxylyl, methoxyphenyl, dimethoxyphenyl, (trifluoromethoxy)phenyl, cyanophenyl, dimethoxybenzyl, methylisoxazolyl, 3H-1,3,4-oxadiazol-2-one-5-yl, methyl, ethyl, propyl, butyl, pentyl, hexyl, heptyl, octyl, nonyl, decyl, undecyl, and dodecyl. Further $R^1$ groups include

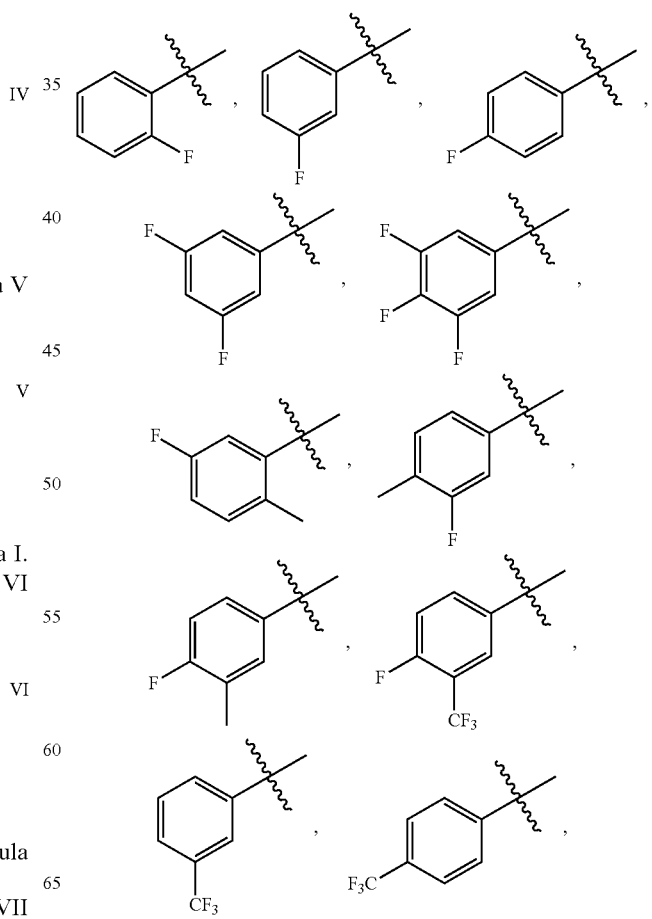

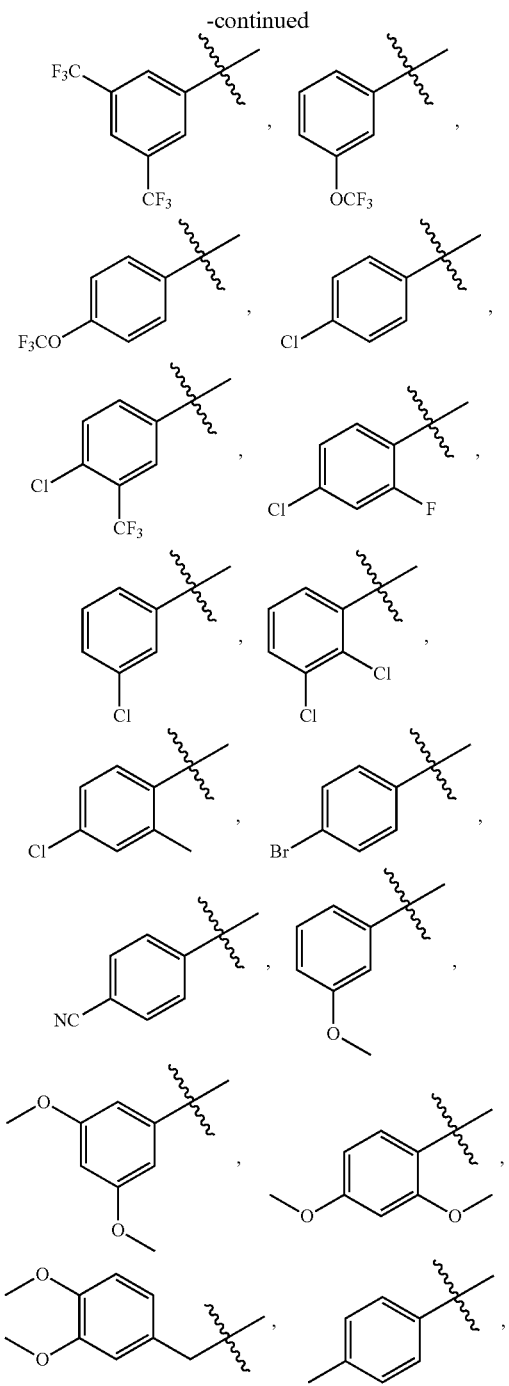

pentyl, and butyl.

R⁴, R¹⁴, R¹⁵, and R¹⁶ are independently selected from -L¹²-C₃-C₆ cycloalkyl, -L¹³-C₂-C₆ heterocycloalkyl, benzyl, -L¹⁴-aryl, and -L¹⁵-heteroaryl, and are optionally substituted with one, two, three, or more substituent groups that are the same or different. Suitable substituent groups include, but are not limited to, F, Cl, Br, I, CF₃, CH₃, OCF₃, OCH₃, and —CN. Additional R⁴, R¹⁴, R¹⁵, and R¹⁶ groups include, but are not limited to, optionally substituted phenyl, halophenyl (e.g., fluorophenyl, chlorophenyl, bromophenyl, iodophenyl), dihalophenyl (e.g., difluorophenyl, dichlorophenyl, dibromophenyl, diiodophenyl), trihalophenyl (e.g., trifluorophenyl, trichlorophenyl, tribromophenyl, triiodophenyl), (trifluoromethyl)phenyl, fluoro(trifluoromethyl)phenyl, chloro(trifluoromethyl)phenyl, bromo(trifluoromethyl)phenyl, iodo(trifluoromethyl)phenyl, tolyl, xylyl, fluorotolyl, chlorotolyl, bromotolyl, iodotolyl, fluoroxylyl, chloroxylyl, bromoxylyl, iodoxylyl, methoxyphenyl, dimethoxyphenyl, (trifluoromethoxy)phenyl, cyanophenyl, dimethoxybenzyl, methylisoxazolyl, and 3H-1,3,4-oxadiazol-2-one-5-yl. Further R⁴ groups include

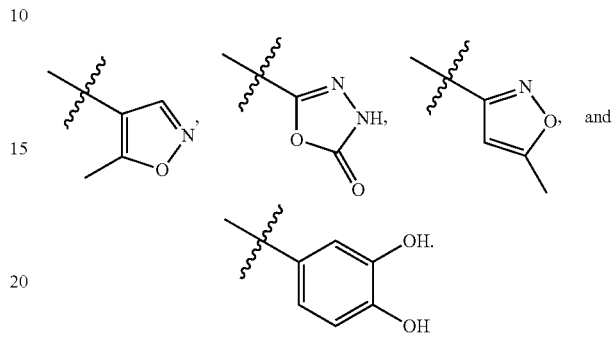

R⁵ is selected from OR¹⁰, C₁ to C₁₂ alkyl, -L⁷-C₃-C₆ cycloalkyl, -L⁸-C₂-C₆ heterocycloalkyl, benzyl, -L⁹-aryl, and -L¹⁰-heteroaryl, and is optionally substituted with one, two, three, or more substituent groups that are the same or different. Suitable substituent groups include, but are not limited to, F, Cl, Br, I, CF₃, CH₃, OCF₃, OCH₃, and —CN. Additional R⁵ groups include, but are not limited to, optionally substituted phenyl, halophenyl (e.g., fluorophenyl, chlorophenyl, bromophenyl, iodophenyl), dihalophenyl (e.g., difluorophenyl, dichlorophenyl, dibromophenyl, diiodophenyl), trihalophenyl (e.g., trifluorophenyl, trichlorophenyl, tribromophenyl, triiodophenyl), (trifluoromethyl)phenyl, fluoro(trifluoromethyl)phenyl, chloro(trifluoromethyl)phenyl, bromo(trifluoromethyl)phenyl, iodo(trifluoromethyl)phenyl, tolyl, xylyl, fluorotolyl, chlorotolyl, bromotolyl, iodotolyl, fluoroxylyl, chloroxylyl, bromoxylyl, iodoxylyl, methoxyphenyl, dimethoxyphenyl, (trifluoromethoxy)phenyl, cyanophenyl, dimethoxybenzyl, methylisoxazolyl, 3H-1,3,4-oxadiazol-2-one-5-yl, methyl, ethyl, propyl, butyl, pentyl, hexyl, heptyl, octyl, nonyl, decyl, undecyl, and dodecyl. Further R⁵ groups include OH.

R⁶, R⁷, R⁹, R¹⁰, R¹¹, R¹², R¹³, and R¹⁷ are independently selected from H and C₁ to C₁₂ alkyl, including C₁ alkyl, C₂ alkyl, C₃ alkyl, C₄ alkyl, C₅ alkyl, C₆ alkyl, C₇ alkyl, C₈ alkyl, C₉ alkyl, C₁₀ alkyl, C₁₁ alkyl, and C₁₂ alkyl.

R⁸ is selected from OR¹¹, N=R¹²R¹³, -L¹¹-R¹⁴, NHSO₂R¹⁵, and NHR¹⁶. Exemplary R⁸ groups include, but are not limited to, OH, OCH₃, N=(CH₃)₂,

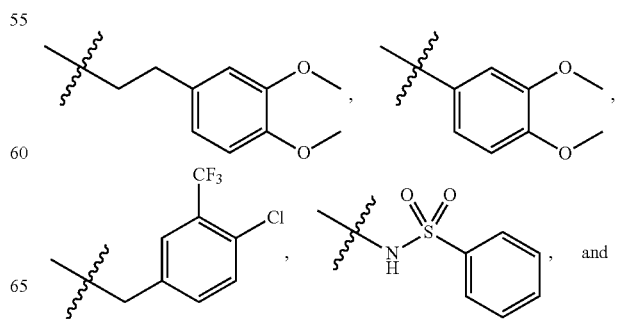

-continued

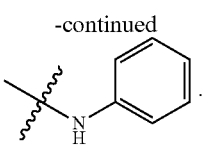

$L^1$, $L^2$, $L^3$, $L^4$, $L^5$, $L^6$, $L^7$, $L^8$, $L^9$, $L^{10}$, $L^{11}$, $L^{12}$, $L^{13}$, $L^{14}$, and $L^{15}$ are independently selected from null (a bond), $C_1$ to $C_{12}$ alkylene, including $C_1$ alkylene, $C_2$ alkylene, $C_3$ alkylene, $C_4$ alkylene, $C_5$ alkylene, $C_6$ alkylene, $C_7$ alkylene, $C_8$ alkylene, $C_9$ alkylene, $C_{10}$ alkylene, $C_{11}$ alkylene, and $C_{12}$ alkylene, and $C_1$ to $C_{12}$ alkenylene, including $C_1$ alkenylene, $C_2$ alkenylene, $C_3$ alkenylene, $C_4$ alkenylene, $C_5$ alkenylene, $C_6$ alkenylene, $C_7$ alkenylene, $C_8$ alkenylene, $C_9$ alkenylene, $C_{10}$ alkenylene, $C_{11}$ alkenylene, and $C_{12}$ alkenylene.

Exemplary compounds of the invention have a formula selected from C256, C259, C265, C267, C276, C277, C288, C309, C311, C280, C300, C313, C314, C320, C323, C326, C328, C334, C342, C240, C241, C246, C248, C251, C255, C260, C261, C262, C263, C264, C266, C268, C278, C281, C282, C287, C289, C295, C296, C297, C301, C304, C305, C307, C310, C322, C336, C339, C340, C341, C362, C279, C285, C286, C299, C306, C330, C344, C345, C346, C347, C348, C356, C357, C358, C359, C360, C361, C363, C364, C284, and salts, esters, or prodrugs thereof. These compounds are depicted in Table 1 herein below.

TABLE 1

| No. | Structure | PAI-1/ uPA IC$_{50}$ in buffer (μM) | PAI-1/ uPA IC$_{50}$ in 1.5% BSA buffer (μM) | PAI-1/ uPA IC$_{50}$ in 10% plasma buffer (μM) |
|---|---|---|---|---|
| C256 | 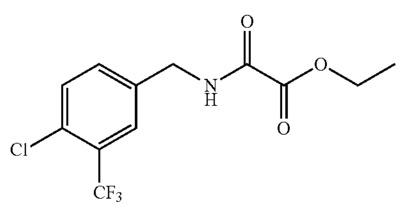 [SMILES: CCOC(=O)C(=O)NCc1ccc(Cl)c(C(F)(F)F)c1] | 1040, 1353 | 204, 235 | 214 |
| C259 | 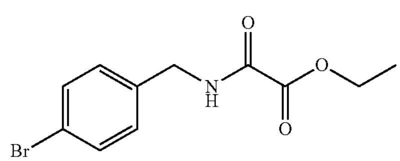 [SMILES: CCOC(=O)C(=O)NCc1ccc(Br)cc1] | 2892, 3141 | 625, 760 | 526 |
| C265 | 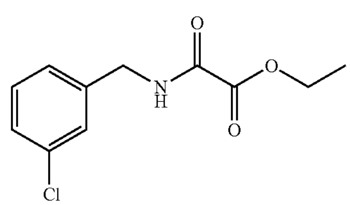 [SMILES: CCOC(=O)C(=O)NCc1cccc(Cl)c1] | 4018 | | |
| C267 | 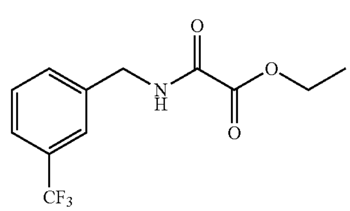 [SMILES: CCOC(=O)C(=O)NCc1cccc(C(F)(F)F)c1] | 3794 | | |
| C276 | 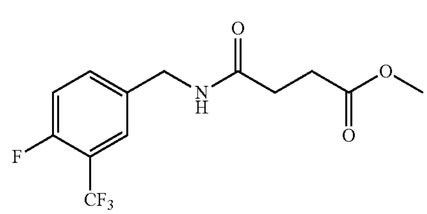 [SMILES: COC(=O)CCC(=O)NCc1ccc(F)c(C(F)(F)F)c1] | 1438 | 428 | 476 |

Synthesized PAI-1 Inhibitor Compounds

TABLE 1-continued
Synthesized PAI-1 Inhibitor Compounds
| No. | Structure | PAI-1/ uPA IC$_{50}$ in buffer (μM) | PAI-1/ uPA IC$_{50}$ in 1.5% BSA buffer (μM) | PAI-1/ uPA IC$_{50}$ in 10% plasma buffer (μM) |
|---|---|---|---|---|
| C277 | 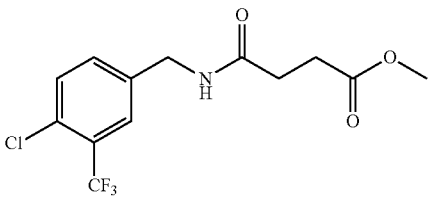 [SMILES: COC(=O)CCC(=O)NCc1ccc(Cl)c(C(F)(F)F)c1] | 750.6, 719 | 165.4, 158 | 148, 142 |
| C288 | 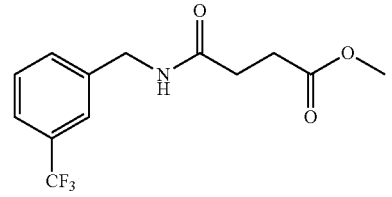 [SMILES: COC(=O)CCC(=O)NCc1cccc(C(F)(F)F)c1] | 2909 | 1061 | 752 |
| C309 | 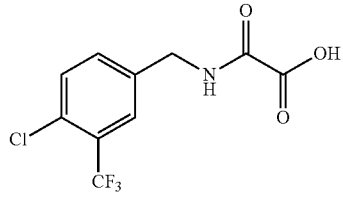 [SMILES: O=C(O)C(=O)NCc1ccc(Cl)c(C(F)(F)F)c1] | 1200 | | |
| C311 | 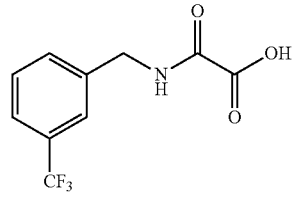 | | | |
| C280 | 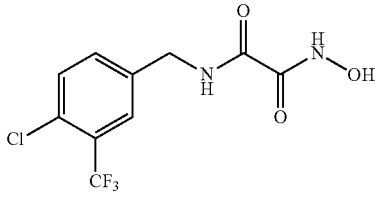 [SMILES: O=C(NO)C(=O)NCc1ccc(Cl)c(C(F)(F)F)c1] | 207, 203 | 166, 159 | 168 |
| C300 | 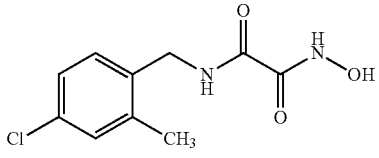 [SMILES: Cc1cc(Cl)ccc1CNC(=O)C(=O)NO] | 5491 | | |
| C313 | 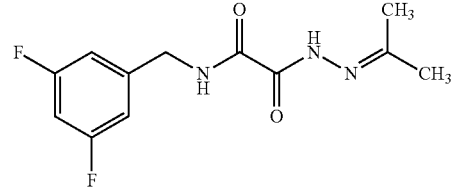 [SMILES: CC(C)=NNC(=O)C(=O)NCc1cc(F)cc(F)c1] | 1196 | 532 | 490 |

TABLE 1-continued

Synthesized PAI-1 Inhibitor Compounds

| No. | Structure | PAI-1/ uPA IC$_{50}$ in buffer (μM) | PAI-1/ uPA IC$_{50}$ in 1.5% BSA buffer (μM) | PAI-1/ uPA IC$_{50}$ in 10% plasma buffer (μM) |
|---|---|---|---|---|
| C314 | 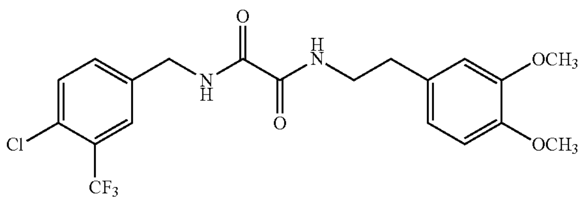 [SMILES: COc1ccc(CCNC(=O)C(=O)NCc2ccc(Cl)c(C(F)(F)F)c2)cc1OC] | | | |
| C320 | 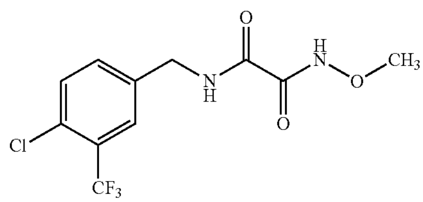 [SMILES: CONC(=O)C(=O)NCc1ccc(Cl)c(C(F)(F)F)c1] | 329 | 513 | 693 |
| C323 | 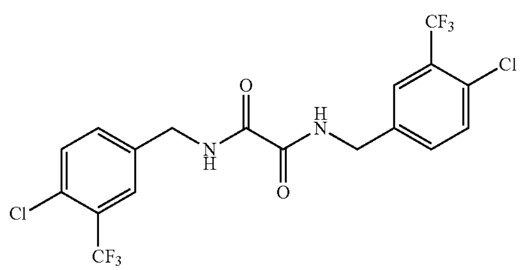 [SMILES: O=C(NCc1ccc(Cl)c(C(F)(F)F)c1)C(=O)NCc1ccc(Cl)c(C(F)(F)F)c1] | | | |
| C326 | 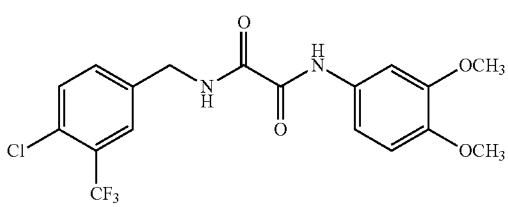 [SMILES: COc1ccc(NC(=O)C(=O)NCc2ccc(Cl)c(C(F)(F)F)c2)cc1OC] | | | |
| C328 | 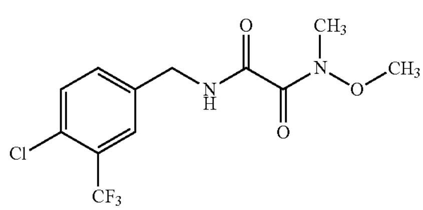 [SMILES: CON(C)C(=O)C(=O)NCc1ccc(Cl)c(C(F)(F)F)c1] | 713 | 345 | 318 |
| C334 | 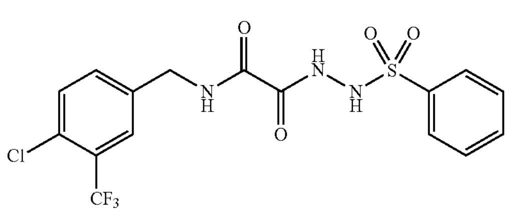 [SMILES: O=C(NCc1ccc(Cl)c(C(F)(F)F)c1)C(=O)NNS(=O)(=O)c1ccccc1] | 189 | | |

TABLE 1-continued

Synthesized PAI-1 Inhibitor Compounds

| No. | Structure | PAI-1/ uPA IC$_{50}$ in buffer (µM) | PAI-1/ uPA IC$_{50}$ in 1.5% BSA buffer (µM) | PAI-1/ uPA IC$_{50}$ in 10% plasma buffer (µM) |
|---|---|---|---|---|
| C342 | 4-Cl, 3-CF$_3$-benzyl-NH-C(O)-C(O)-NH-NH-phenyl | | | |
| C240 | pentyl-NH-C(O)-C(O)-NH-NH$_2$ | 3766, 3912 | 2221, 1973 | 1208 |
| C241 | butyl-NH-C(O)-C(O)-NH-NH$_2$ | 1933 | | |
| C246 | 3,4-(H$_3$CO)$_2$-phenethyl-NH-C(O)-C(O)-NH-NH$_2$ | 2559 | | |
| C248 | 4-F-benzyl-NH-C(O)-C(O)-NH-NH$_2$ | 1190, 1313 | 652, 646 | 478 |
| C251 | 4-Cl, 3-CF$_3$-benzyl-NH-C(O)-C(O)-NH-NH$_2$ | 68.6, 76 | 110, 123 | 108 |
| C255 | 4-F$_3$CO-benzyl-NH-C(O)-C(O)-NH-NH$_2$ | 2064, 1780 | 221, 292 | 279 |
| C260 | 4-Br-benzyl-NH-C(O)-C(O)-NH-NH$_2$ | 147, 187 | 43, 545 | 525 |

TABLE 1-continued

Synthesized PAI-1 Inhibitor Compounds

| No. | Structure | PAI-1/ uPA IC$_{50}$ in buffer (μM) | PAI-1/ uPA IC$_{50}$ in 1.5% BSA buffer (μM) | PAI-1/ uPA IC$_{50}$ in 10% plasma buffer (μM) |
|---|---|---|---|---|
| C261 | 4-F, 3-CF$_3$ benzyl-NH-C(O)-C(O)-NH-NH$_2$ | 102, 103 | 68, 86 | 69 |
| C262 | 4-F, 3-CH$_3$ benzyl-NH-C(O)-C(O)-NH-NH$_2$ | 170, 187 | 63, 84 | 86 |
| C263 | 2-F benzyl-NH-C(O)-C(O)-NH-NH$_2$ | 2837 | 1685 | 1356 |
| C264 | 3-F benzyl-NH-C(O)-C(O)-NH-NH$_2$ | 2121 | 1175 | 1248 |
| C266 | 3-Cl benzyl-NH-C(O)-C(O)-NH-NH$_2$ | 568, 549 | 126 | 219 |
| C268 | 3-OCF$_3$ benzyl-NH-C(O)-C(O)-NH-NH$_2$ | 135, 134 | 65 | 77 |
| C278 | 4-Cl, 3-CF$_3$ benzyl-NH-C(O)-CH$_2$-CH$_2$-C(O)-NH-NH$_2$ | 640, 642 | 118, 130 | 142 |

TABLE 1-continued

Synthesized PAI-1 Inhibitor Compounds

| No. | Structure | PAI-1/ uPA IC$_{50}$ in buffer (μM) | PAI-1/ uPA IC$_{50}$ in 1.5% BSA buffer (μM) | PAI-1/ uPA IC$_{50}$ in 10% plasma buffer (μM) |
|---|---|---|---|---|
| C281 | 2,4-dimethoxybenzyl oxalohydrazide | 2285 | | |
| C282 | 4-chloro-2-methylbenzyl oxalohydrazide | 225, 219 | 163, 154 | 121 |
| C287 | 4-fluoro-3-(trifluoromethyl)benzyl succinohydrazide | 1187 | 363 | 304 |
| C289 | 3-(trifluoromethyl)benzyl succinohydrazide | 2725 | 1099 | 733 |
| C295 | 3-methoxybenzyl oxalohydrazide | 1337 | 776 | 736 |
| C296 | 4-(trifluoromethyl)benzyl oxalohydrazide | 112 | 69 | 64 |
| C297 | 3-(trifluoromethyl)benzyl oxalohydrazide | 136 | 111 | 87 |

TABLE 1-continued

Synthesized PAI-1 Inhibitor Compounds

| No. | Structure | PAI-1/ uPA IC$_{50}$ in buffer (μM) | PAI-1/ uPA IC$_{50}$ in 1.5% BSA buffer (μM) | PAI-1/ uPA IC$_{50}$ in 10% plasma buffer (μM) |
|---|---|---|---|---|
| C301 | 2,3-dichlorobenzyl oxalohydrazide | 173 | 128 | 106 |
| C304 | 3,4,5-trifluorobenzyl oxalohydrazide | 162 | 90 | 74 |
| C305 | 3-fluoro-4-methylbenzyl oxalohydrazide | 224 | 81 | 62 |
| C307 | 4-chloro-2-fluorobenzyl oxalohydrazide | 465 | 99 | 101 |
| C310 | 3-(trifluoromethyl)benzyl N'-tert-butyl oxalohydrazide | | | |
| C322 | 3,5-dimethoxybenzyl oxalohydrazide | 4315 | | |
| C336 | 4-cyanobenzyl oxalohydrazide | 5469 | 892 | 851 |

TABLE 1-continued

Synthesized PAI-1 Inhibitor Compounds

| No. | Structure | PAI-1/ uPA IC$_{50}$ in buffer (μM) | PAI-1/ uPA IC$_{50}$ in 1.5% BSA buffer (μM) | PAI-1/ uPA IC$_{50}$ in 10% plasma buffer (μM) |
|---|---|---|---|---|
| C339 | 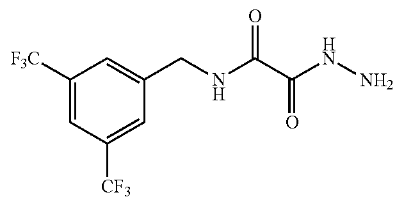 [SMILES: NNC(=O)C(=O)NCc1cc(C(F)(F)F)cc(C(F)(F)F)c1] | 282 | 247 | 303 |
| C340 | 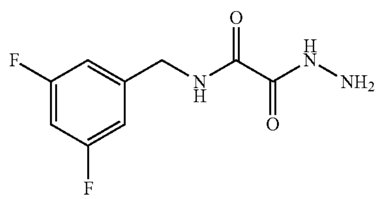 [SMILES: NNC(=O)C(=O)NCc1cc(F)cc(F)c1] | 337 | 249 | 272 |
| C341 | 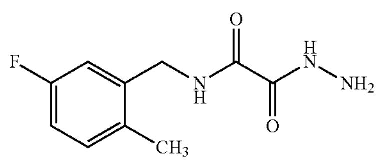 [SMILES: Cc1ccc(F)cc1CNC(=O)C(=O)NN] | 900 | 1460 | 1868 |
| C362 | 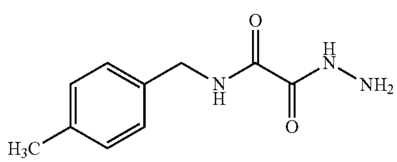 | 533 | 353 | 229 |
| C279 | 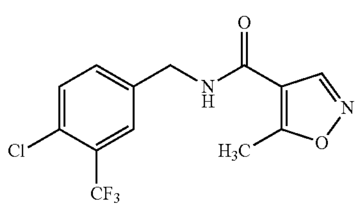 [SMILES: Cc1oncc1C(=O)NCc1ccc(Cl)c(C(F)(F)F)c1] | 539, 593 | 545, 504 | 680 |
| C285 | 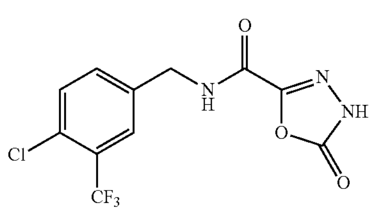 [SMILES: O=C(NCc1ccc(Cl)c(C(F)(F)F)c1)c1n[nH]c(=O)o1] | 422, 388 | 265 | 306 |
| C286 | 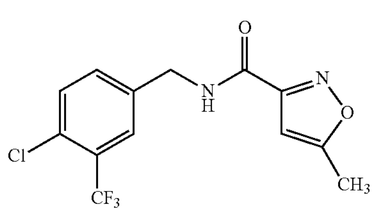 [SMILES: Cc1cc(C(=O)NCc2ccc(Cl)c(C(F)(F)F)c2)no1] | 580 | | |

TABLE 1-continued

Synthesized PAI-1 Inhibitor Compounds

| No. | Structure | PAI-1/uPA IC$_{50}$ in buffer (μM) | PAI-1/uPA IC$_{50}$ in 1.5% BSA buffer (μM) | PAI-1/uPA IC$_{50}$ in 10% plasma buffer (μM) |
|---|---|---|---|---|
| C299 | 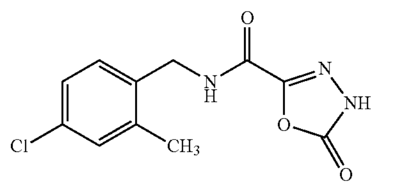 [SMILES: Cc1cc(Cl)ccc1CNC(=O)c1n[nH]c(=O)o1] | 238 | 739 | 628 |
| C306 | 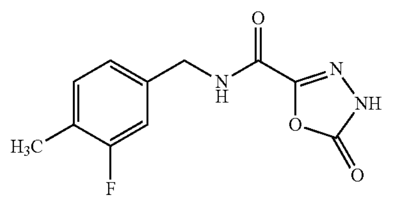 [SMILES: Cc1ccc(CNC(=O)c2n[nH]c(=O)o2)cc1F] | 1159 | 403 | 405 |
| C330 | 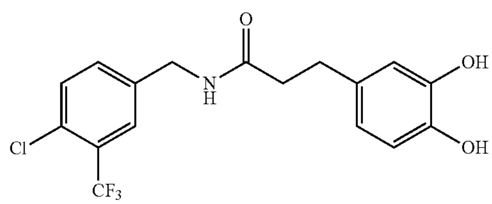 [SMILES: O=C(CCc1ccc(O)c(O)c1)NCc1ccc(Cl)c(C(F)(F)F)c1] | 365, 423* | 112 | 115 |
| C344 | 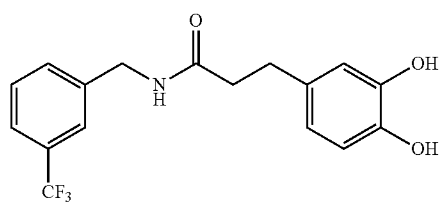 [SMILES: O=C(CCc1ccc(O)c(O)c1)NCc1cccc(C(F)(F)F)c1] | 1002 | 830 | 866 |
| C345 | 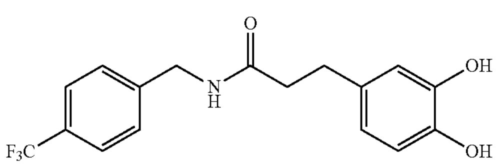 [SMILES: O=C(CCc1ccc(O)c(O)c1)NCc1ccc(C(F)(F)F)cc1] | 1469 | 673 | 539 |
| C346 | 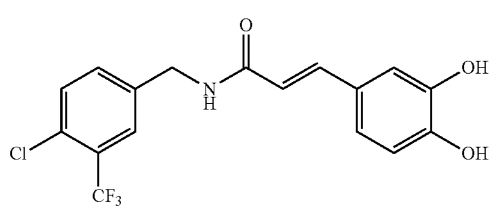 [SMILES: O=C(/C=C/c1ccc(O)c(O)c1)NCc1ccc(Cl)c(C(F)(F)F)c1] | 353 | | |
| C347 | 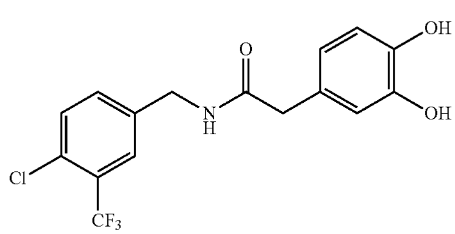 [SMILES: O=C(Cc1ccc(O)c(O)c1)NCc1ccc(Cl)c(C(F)(F)F)c1] | 888 | 309 | 293 |

TABLE 1-continued

Synthesized PAI-1 Inhibitor Compounds

| No. | Structure | PAI-1/ uPA IC$_{50}$ in buffer (μM) | PAI-1/ uPA IC$_{50}$ in 1.5% BSA buffer (μM) | PAI-1/ uPA IC$_{50}$ in 10% plasma buffer (μM) |
|---|---|---|---|---|
| C348 | 4-Cl-3-CF$_3$-benzyl-NH-C(O)-3,4-dihydroxyphenyl | 99 | 454 | 240 |
| C356 | 3,4,5-trifluorobenzyl-NH-C(O)-CH$_2$CH$_2$-3,4-dihydroxyphenyl | 1100 | 1241 | 544 |
| C357 | 3-OCF$_3$-benzyl-NH-C(O)-CH$_2$CH$_2$-3,4-dihydroxyphenyl | 1370 | 1227 | 567 |
| C358 | 4-F-3-CH$_3$-benzyl-NH-C(O)-CH$_2$CH$_2$-3,4-dihydroxyphenyl | 1501 | 1229 | 619 |
| C359 | 4-Cl-benzyl-NH-C(O)-CH$_2$CH$_2$-3,4-dihydroxyphenyl | 3373 | 2084 | 974 |
| C360 | 4-Br-benzyl-NH-C(O)-3,4-dihydroxyphenyl | 164 | 1670 | 771 |
| C361 | 4-Cl-benzyl-NH-C(O)-3,4-dihydroxyphenyl | 232 | 2000 | 851 |

TABLE 1-continued

Synthesized PAI-1 Inhibitor Compounds

| No. | Structure | PAI-1/ uPA IC$_{50}$ in buffer (μM) | PAI-1/ uPA IC$_{50}$ in 1.5% BSA buffer (μM) | PAI-1/ uPA IC$_{50}$ in 10% plasma buffer (μM) |
| --- | --- | --- | --- | --- |
| C363 | 4-(CF$_3$)benzyl-NH-C(O)-(3,4-dihydroxyphenyl) | 199 | 751 | 309 |
| C364 | 3-(CF$_3$)benzyl-NH-C(O)-(3,4-dihydroxyphenyl) | 475 | 898 | 533 |
| C284 | 4-Cl-3-(CF$_3$)benzyl-NH-C(O)-NH-OH | 2481 | | |

*pH 7.8 was used.

Comparative compounds that do not demonstrate PAI-1 inhibitory activity in buffer (40 mM HEPES, 100 mM NaCl, 0.05% Tween-20, 10% DMSO, pH 7.4) in the assay described in Example 11 herein are depicted in Table 2.

TABLE 2

Synthesized Comparative Compounds

| No. | Structure |
| --- | --- |
| E242 | 3,4-dimethoxyphenyl-NH-C(O)-C(O)-O-ethyl |
| E243 | 4-Br-2-(CF$_3$)phenyl-NH-C(O)-C(O)-O-ethyl |
| E244 | 4-Br-2-F-phenyl-NH-C(O)-C(O)-O-ethyl |
| E245 | hexyl-NH-C(O)-C(O)-O-ethyl |
| E247 | 4-F-benzyl-NH-C(O)-C(O)-O-ethyl |
| E254 | 4-(OCF$_3$)benzyl-NH-C(O)-C(O)-O-ethyl |
| E257 | 4-methoxy-2-methylphenyl-NH-C(O)-C(O)-O-ethyl |

TABLE 2-continued

Synthesized Comparative Compounds

| No. | Structure |
|---|---|
| E258 | 2-(OCF3)benzyl-NH-C(O)-C(O)-O-ethyl |
| E290 | methyl 4-[4-(methyl succinate-oxy)benzyl-NH-C(O)-CH2CH2-C(O)-O-methyl] |
| E319 | 4-cyanobenzyl-NH-C(O)-C(O)-O-ethyl |
| E308 | 4-Cl-3-CF3-benzyl-NH-C(O)-CH2CH2-C(O)-OH |
| E312 | 3,5-bis(CF3)-benzyl-NH-C(O)-C(O)-NH-N=C(CH3)2 |
| E324 | 4-Cl-3-CF3-benzyl-NH-C(O)-C(O)-NH-CH2-(4-OCF3-phenyl) |
| E325 | 4-Cl-3-CF3-benzyl-NH-C(O)-C(O)-NH-O-CH2-phenyl |
| E329 | 4-Cl-3-CF3-benzyl-NH-C(O)-C(O)-N(indoline) |
| E331 | 4-Cl-3-CF3-benzyl-NH-C(O)-C(O)-N(piperidine) |
| E332 | 4-Cl-3-CF3-benzyl-NH-C(O)-C(O)-N(n-hexyl)2 |
| E335 | 4-Cl-3-CF3-benzyl-NH-C(O)-C(O)-NH-CH2CH2CH2-phenyl |
| E343 | 4-Cl-3-CF3-benzyl-NH-C(O)-C(O)-N(isobutyl)2 |
| E338 | 4-Cl-3-CF3-benzyl-NH-C(O)-C(O)-NH-CH2-(4-F-phenyl) |
| E234 | benzyl-NH-C(O)-C(O)-NH-NH2 |
| E235 | phenethyl-NH-C(O)-C(O)-NH-NH2 |
| E237 | 4-Br-2-CF3-phenyl-NH-C(O)-C(O)-NH-NH2 |

TABLE 2-continued

Synthesized Comparative Compounds

| No. | Structure |
|---|---|
| E238 | 3,4-dimethoxyphenyl-NH-C(O)-C(O)-NHNH₂ |
| E252 | 2-(trifluoromethoxy)benzyl-NH-C(O)-C(O)-NHNH₂ |
| E253 | 4-methoxy-2-methylphenyl-NH-C(O)-C(O)-NHNH₂ |
| E269 | 2-(naphthalen-2-yl)ethyl-NH-C(O)-C(O)-NHNH₂ |
| E291 | 4-hydroxybenzyl-NH-C(O)-CH₂CH₂-C(O)-NHNH₂ |
| E327 | 4-chloro-3-(trifluoromethyl)benzyl-NH-C(O)-C(O)-NH-NH-(2,4-difluorophenyl) |
| E333 | 4-chloro-3-(trifluoromethyl)benzyl-NH-C(O)-C(O)-NH-NH-C(O)-(3-bromophenyl) |
| E321 | 4-chloro-3-(trifluoromethyl)benzyl-NH-C(O)-CH=CH-(3,4-dimethoxyphenyl) |
| E349 | 4-chloro-3-(trifluoromethyl)benzyl-NH-C(O)-CH=CH-(3,4-difluorophenyl) |
| E350 | 4-chloro-3-(trifluoromethyl)benzyl-NH-C(O)-CH=CH-(4-fluorophenyl) |
| E351 | 4-chloro-3-(trifluoromethyl)benzyl-NH-C(O)-CH=CH-(4-trifluoromethylphenyl) |
| E352 | 4-chloro-3-(trifluoromethyl)benzyl-NH-C(O)-CH=CH-(3-trifluoromethoxyphenyl) |
| E353 | 4-chloro-3-(trifluoromethyl)benzyl-NH-C(O)-CH=CH-(benzo[d][1,3]dioxol-5-yl) |
| E354 | 4-chloro-3-(trifluoromethyl)benzyl-NH-C(O)-CH₂CH₂-(4-hydroxyphenyl) |
| E355 | 4-chloro-3-(trifluoromethyl)benzyl-NH-C(O)-CH₂CH₂-(3,4-dichlorophenyl) |
| E283 | 4-chloro-3-(trifluoromethyl)benzyl-NH-C(O)-NH-NH₂ |

TABLE 2-continued

Synthesized Comparative Compounds

| No. | Structure |
|---|---|
| E298 | 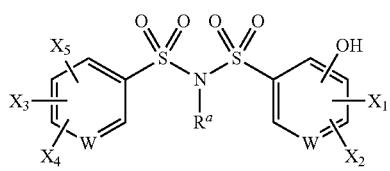 |

Compounds of the invention include those of formula VIII or a salt, ester, or prodrug thereof:

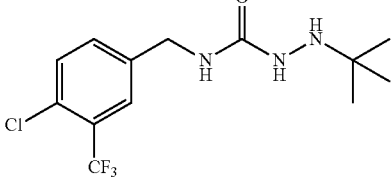

VIII wherein:

W is C or N;

$X_1$, $X_2$, $X_3$, $X_4$, and $X_5$ are independently selected from the group consisting of —H, —OH, —OR, —F, —Cl, —Br, —I, —NO$_2$, —NO, —N(R)$_2$, —N(R)$_3^+$, —C(O)R, —C(O)OR, —CHO, —C(O)NH$_2$, —C(O)SR, —CN, —S(O)$_2$R, —SO$_3$R, —SO$_3$H, —SO$_2$N(R)$_2$, —S=O, $C_1$ to $C_{12}$ alkyl, aryl, substituted aryl, heteroaryl, and substituted heteroaryl;

R is selected from the group consisting of $C_1$ to $C_6$ alkyl, $C_3$ to $C_6$ cycloalkyl, CH$_2$—$C_3$-$C_6$ cycloalkyl, phenyl, tolyl, and benzyl;

$R^a$ is selected from the group consisting of $C_1$ to $C_{12}$ alkyl, $C_3$ to $C_6$ cycloalkyl, (CH$_2$)$_m$—$C_3$-$C_6$ cycloalkyl, $C_2$ to $C_6$ heterocycloalkyl, (CH$_2$)$_m$—$C_2$-$C_6$ heterocycloalkyl, $C_2$ to $C_6$ heterocycloalkyl, (CH$_2$)$_m$—$C_2$-$C_6$ heterocycloalkyl, benzyl, aryl, (CH$_2$)$_m$-aryl, heteroaryl, (CH$_2$)$_m$-heteroaryl, and substituted derivatives thereof; and m is 1, 2, 3, 4, 5, or 6.

In some embodiments, compounds of the invention include those of formula VIII as defined above with the proviso that at most two of $X_1$, $X_2$, $X_3$, $X_4$, and $X_5$ are OH.

In some embodiments, compounds of the invention include those of formula VIII as defined above excluding compounds having a formula

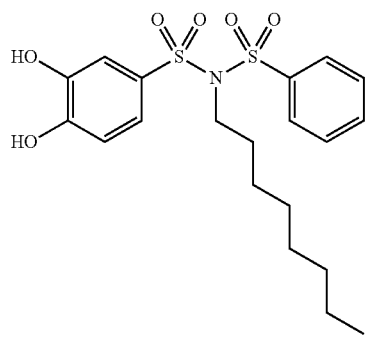

In some embodiments, compounds of the invention include those of formula VIII as defined above with the proviso that at most three of $X_1$, $X_2$, $X_3$, $X_4$, and $X_5$ are H.

Compounds of the invention include those of formula IX or a salt, ester, or prodrug thereof:

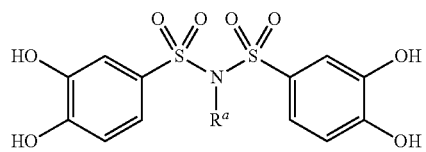

IX wherein $R^a$ is selected from the group consisting of benzyl, aryl, (CH$_2$)$_m$-aryl, heteroaryl, (CH$_2$)$_m$-heteroaryl, and substituted derivatives thereof; and m is 1, 2, 3, 4, 5, or 6.

In some embodiments, compounds of the invention include those of formula VIII or IX as defined above wherein $R^a$ is selected from the group consisting of:

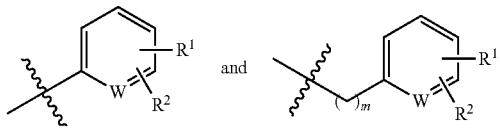

wherein: W is C or N; and $R^1$ and $R^2$ are independently selected from the group consisting of —H, —F, —Cl, —Br, —I, —CF$_3$, $C_1$ to $C_{12}$ alkyl, and phenyl.

Exemplary compounds of the invention have a formula selected from C152, C155, C173, C189, C191, C197, C224, C292, C293, C294, C153, C162, C163, C165, C188, C195, C157, C158, C182, C183, and salts, esters, or prodrugs thereof. These compounds are depicted in Table 3 herein below.

TABLE 3

| | | PAI-1/ uPA IC$_{50}$ (μM) | PAI-1/ tPA IC$_{50}$ (μM) | ATIII/ αIIa IC$_{50}$ (μM) |
|---|---|---|---|---|
| No. | Structure | | | |
| C152 | | 1.57 | 1.71 | 87 |
| C155 | | 30.44 | 34.84 | 2326 |
| C173 | | 19.2 | | |
| C189 | | 2.29 | | |

TABLE 3-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C191 | 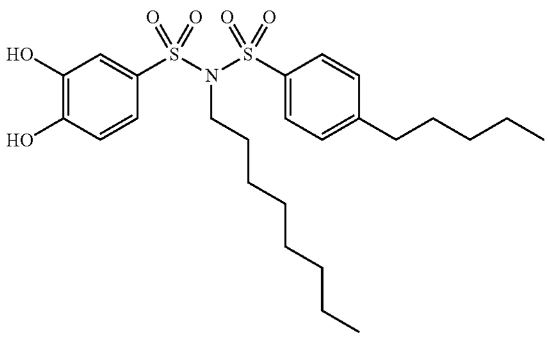 [SMILES: CCCCCCCCN(S(=O)(=O)c1ccc(CCCCC)cc1)S(=O)(=O)c1ccc(O)c(O)c1] | 1.28 | | |
| C197 | 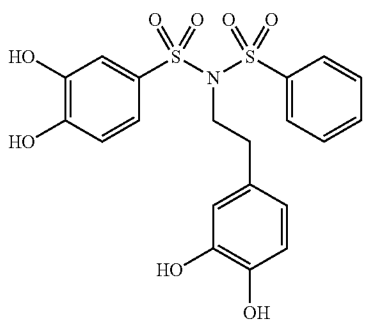 [SMILES: O=S(=O)(c1ccccc1)N(CCc1ccc(O)c(O)c1)S(=O)(=O)c1ccc(O)c(O)c1] | 0.173 | | |
| C224 | 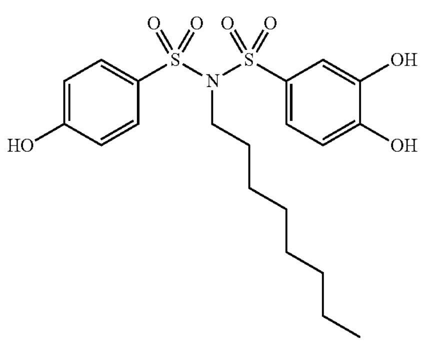 [SMILES: CCCCCCCCN(S(=O)(=O)c1ccc(O)cc1)S(=O)(=O)c1ccc(O)c(O)c1] | 4.34 | | |
| C292 | 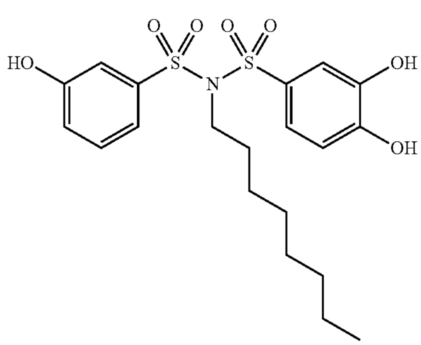 [SMILES: CCCCCCCCN(S(=O)(=O)c1cccc(O)c1)S(=O)(=O)c1ccc(O)c(O)c1] | 4.94, 68* | | |

TABLE 3-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C293 | 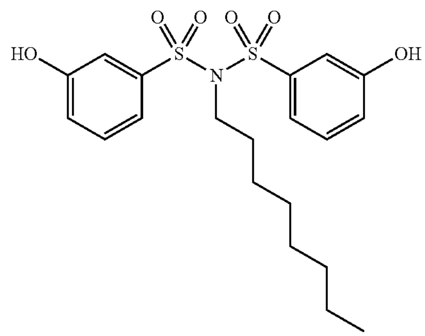 [SMILES: CCCCCCCCN(S(=O)(=O)c1cccc(O)c1)S(=O)(=O)c1cccc(O)c1] | 77.6, 123* | | |
| C294 | 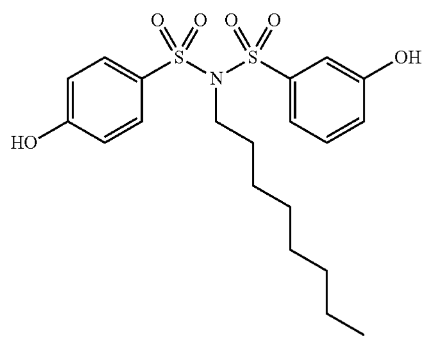 [SMILES: CCCCCCCCN(S(=O)(=O)c1ccc(O)cc1)S(=O)(=O)c1cccc(O)c1] | 120.5, 234* | | |
| C153 | 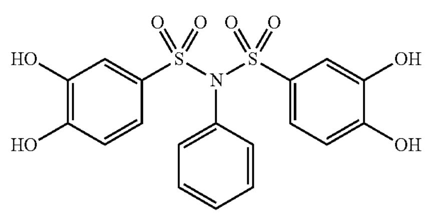 [SMILES: O=S(=O)(c1ccc(O)c(O)c1)N(c1ccccc1)S(=O)(=O)c1ccc(O)c(O)c1] | 0.70 | 1.02 | |
| C162 | 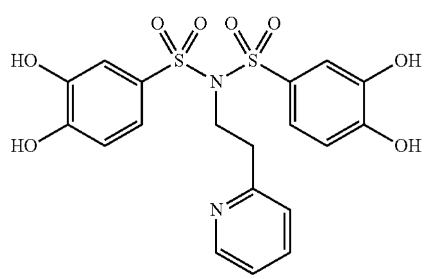 [SMILES: O=S(=O)(c1ccc(O)c(O)c1)N(CCc1ccccn1)S(=O)(=O)c1ccc(O)c(O)c1] | 3.90 | 7.59 | |
| C163 | 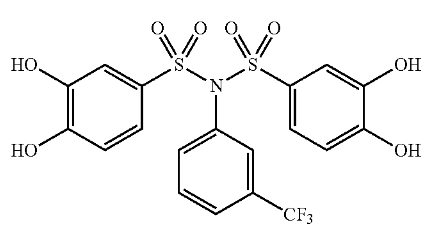 [SMILES: O=S(=O)(c1ccc(O)c(O)c1)N(c1cccc(C(F)(F)F)c1)S(=O)(=O)c1ccc(O)c(O)c1] | 0.288 | 0.611 | |

TABLE 3-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C165 | 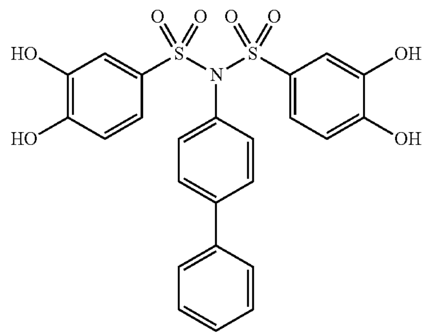 [SMILES: O=S(=O)(c1ccc(O)c(O)c1)N(c1ccc(-c2ccccc2)cc1)S(=O)(=O)c1ccc(O)c(O)c1] | 0.35 | 0.51 | |
| C188 | 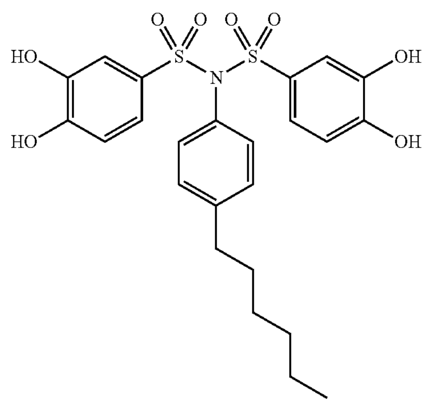 [SMILES: CCCCCCc1ccc(N(S(=O)(=O)c2ccc(O)c(O)c2)S(=O)(=O)c2ccc(O)c(O)c2)cc1] | 0.12 | | |
| C195 | 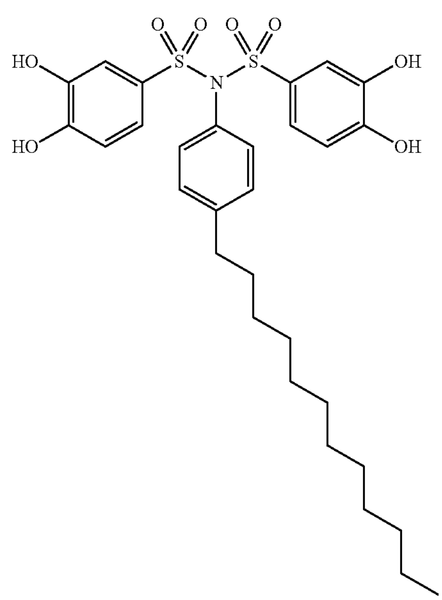 [SMILES: CCCCCCCCCCCCc1ccc(N(S(=O)(=O)c2ccc(O)c(O)c2)S(=O)(=O)c2ccc(O)c(O)c2)cc1] | 0.92 | | |

TABLE 3-continued
Synthesized PAI-1 Inhibitor Compounds
| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C157 | 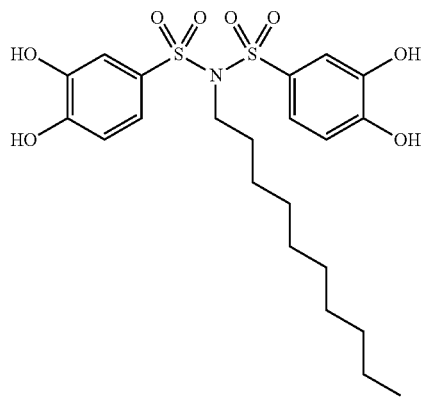 [SMILES: CCCCCCCCCCN(S(=O)(=O)c1ccc(O)c(O)c1)S(=O)(=O)c1ccc(O)c(O)c1] | 0.25 | 0.98 | 44.37 |
| C158 | 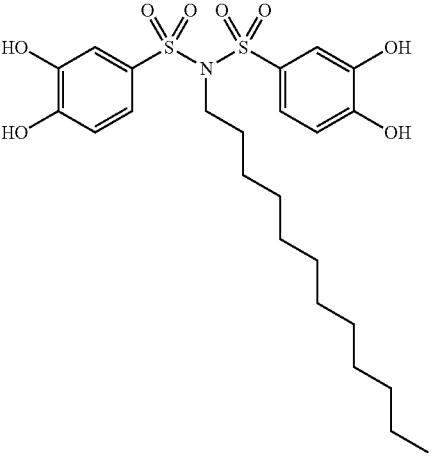 [SMILES: CCCCCCCCCCCCN(S(=O)(=O)c1ccc(O)c(O)c1)S(=O)(=O)c1ccc(O)c(O)c1] | 2.60 | 1.44 | 547 |
| C182 | 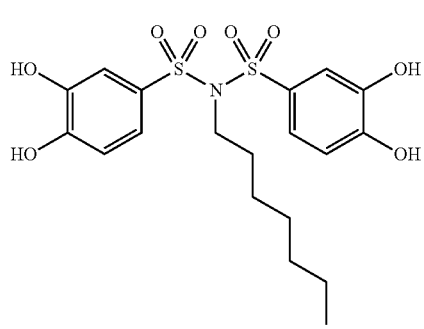 [SMILES: CCCCCCCN(S(=O)(=O)c1ccc(O)c(O)c1)S(=O)(=O)c1ccc(O)c(O)c1] | 0.033 | | |

TABLE 3-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C183 | 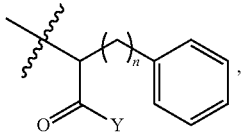 | 0.18 | | |

*pH 7.4 was used.

Comparative compounds that do not demonstrate PAI-1 inhibitory activity in buffer (40 mM HEPES, 100 mM NaCl, 0.05% Tween-20, 10% DMSO, pH 7.8) in the assay described in Example 12 herein are depicted in Table 4.

TABLE 4

Synthesized Comparative Compounds

| No. | Structure |
|---|---|
| E174 | 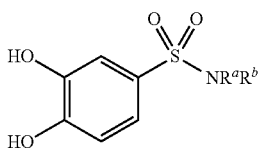 |

Compounds of the invention include those of formula X or a salt, ester, or prodrug thereof:

X wherein $R^a$ is $C_1$ to $C_{12}$ alkyl, $R^b$ is selected from the group consisting of $C_1$ to $C_{12}$ alkyl, aryl, heteroaryl, $(CH_2)_m$—R, and

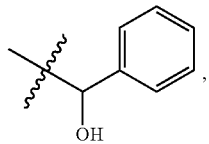 [SMILES: *C(O)c1ccccc1]

or $R^a$ and $R^b$ taken together with the N atom to which they are bonded form an optionally substituted 3- to 8-membered heterocyclic ring;

m is 1, 2, 3, 4, 5, or 6;

n is 0, 1, 2, 3, 4, 5, or 6;

Y is selected from the group consisting of $NH_2$ and OH; and

R selected from the group consisting of substituted phenyl and heteroaryl.

In some embodiments, compounds of the invention include those of formula X as defined above wherein $R^a$ is selected from the group consisting of butyl, pentyl, hexyl, heptyl, octyl, nonyl, and decyl. In some embodiments, compounds of the invention include those of formula X as defined above wherein $R^b$ is selected from the group consisting of butyl, pentyl, hexyl, heptyl, octyl, nonyl, decyl, fluorophenyl, chlorophenyl, bromophenyl, iodophenyl, trifluoromethylphenyl, and dichlorohydroxyphenyl.

Compounds of the invention include those of formula XI or a salt, ester, or prodrug thereof:

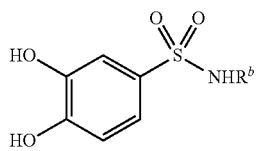

XI wherein

R$^b$ is selected from the group consisting of aryl, heteroaryl, (CH$_2$)$_m$—R, and

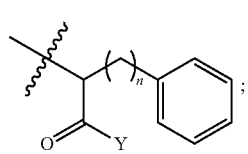

m is 1, 2, 3, 4, 5, or 6;

n is 0, 1, 2, 3, 4, 5, or 6;

Y is selected from the group consisting of NH$_2$ and OH; and

R selected from the group consisting of

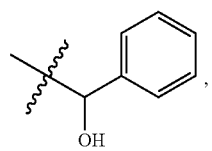 [SMILES: *C(O)c1ccccc1]

CO$_2$H, phenyl, substituted phenyl and heteroaryl.

Compounds of the invention include those of formula XII or a salt, ester, or prodrug thereof:

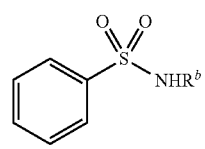

XII wherein

R$^b$ is selected from the group consisting of aryl, heteroaryl, (CH$_2$)$_m$—R, and

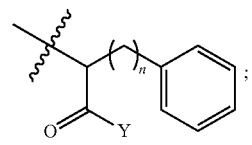

m is 1, 2, 3, 4, 5, or 6;

n is 0, 1, 2, 3, 4, 5, or 6;

Y is selected from the group consisting of NH$_2$ and OH; and

R selected from the group consisting of

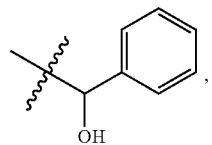 [SMILES: *C(O)c1ccccc1]

CO$_2$H, phenyl, substituted phenyl and heteroaryl.

Exemplary compounds of the invention have a formula selected from C170, C171, C172, C175, C177, C179, C180, C186, C193, C205, C160, C187, C190, C198, C232, C233, C249, C270, C271, C272, C273, C274, C275, C303, C210, and salts, esters, or prodrugs thereof. These compounds are depicted in Table 5 herein below.

TABLE 5

| | Synthesized PAI-1 Inhibitor Compounds | | | |
|---|---|---|---|---|
| No. | Structure | PAI-1/ uPA IC$_{50}$ (μM) | PAI-1/ tPA IC$_{50}$ (μM) | ATIII/ αIIa IC$_{50}$ (μM) |
| C170 | | 5.49 | | |

TABLE 5-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C171 | 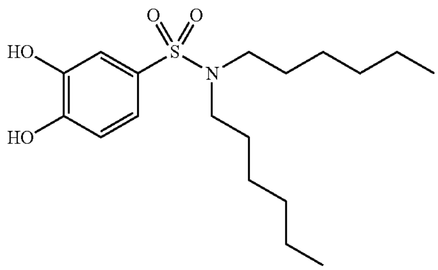 [SMILES: CCCCCCN(CCCCCC)S(=O)(=O)c1ccc(O)c(O)c1] | 1.67 | | |
| C172 | 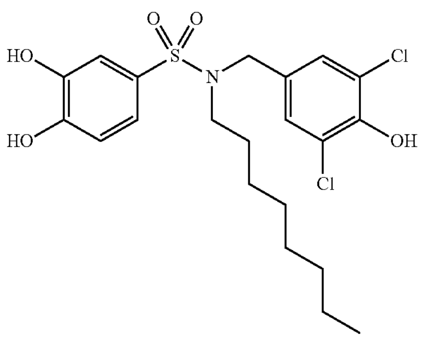 [SMILES: CCCCCCCCN(Cc1cc(Cl)c(O)c(Cl)c1)S(=O)(=O)c1ccc(O)c(O)c1] | 1.98 | | |
| C175 | 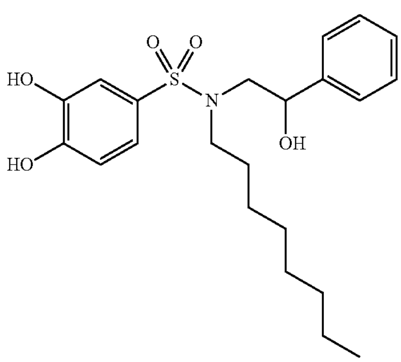 [SMILES: CCCCCCCCN(CC(O)c1ccccc1)S(=O)(=O)c1ccc(O)c(O)c1] | 6.74 | | |
| C177 | 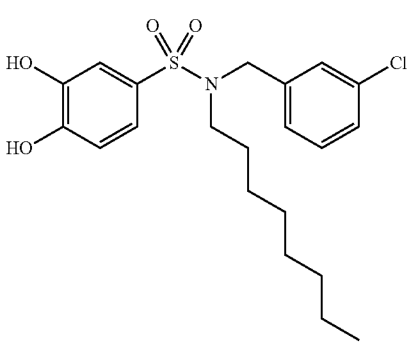 [SMILES: CCCCCCCCN(Cc1cccc(Cl)c1)S(=O)(=O)c1ccc(O)c(O)c1] | 5.11 | | |

TABLE 5-continued

Synthesized PAI-1 Inhibitor Compounds

| No. | Structure | PAI-1/uPA IC$_{50}$ (μM) | PAI-1/tPA IC$_{50}$ (μM) | ATIII/αIIa IC$_{50}$ (μM) |
|---|---|---|---|---|
| C179 | 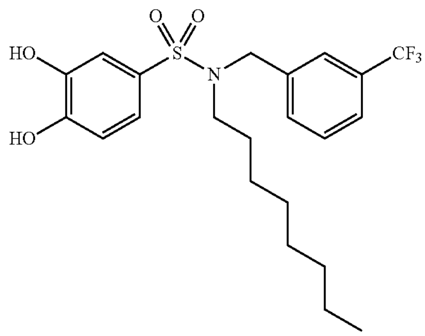 [SMILES: CCCCCCCCN(Cc1cccc(C(F)(F)F)c1)S(=O)(=O)c1ccc(O)c(O)c1] | 2.40 | | |
| C180 | 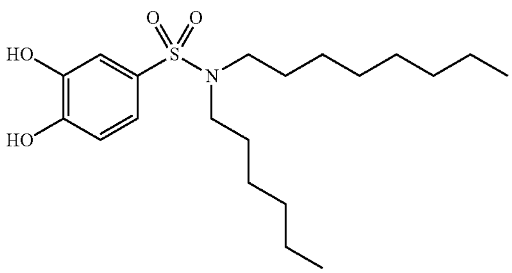 [SMILES: CCCCCCCCN(CCCCCC)S(=O)(=O)c1ccc(O)c(O)c1] | 1.34 | | |
| C186 | 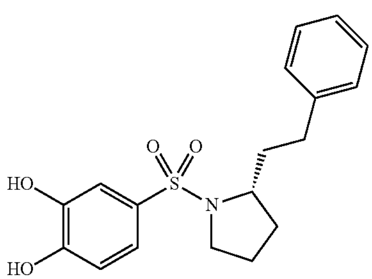 [SMILES: O=S(=O)(c1ccc(O)c(O)c1)N1CCC[C@H]1CCc1ccccc1] | 6.98 | | |
| C193 | 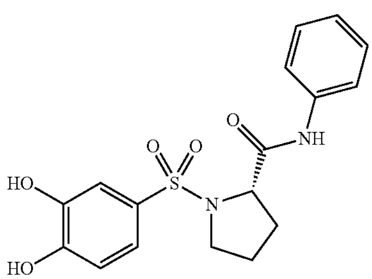 [SMILES: O=C(Nc1ccccc1)[C@@H]1CCCN1S(=O)(=O)c1ccc(O)c(O)c1] | 552 | | |
| C205 | 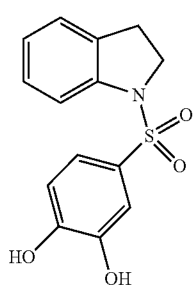 [SMILES: O=S(=O)(c1ccc(O)c(O)c1)N1CCc2ccccc21] | 5.05 | | |

TABLE 5-continued
Synthesized PAI-1 Inhibitor Compounds
| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C160 | 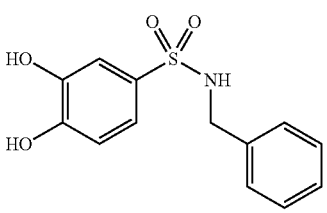 [SMILES: O=S(=O)(NCc1ccccc1)c1ccc(O)c(O)c1] | 39.04 | 58.16 | 2326 |
| C187 | 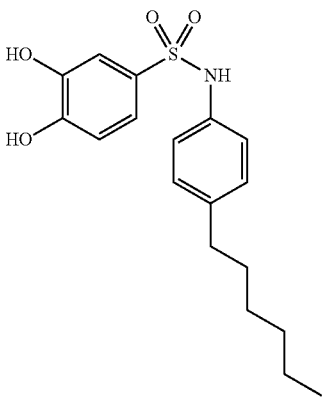 [SMILES: CCCCCCc1ccc(NS(=O)(=O)c2ccc(O)c(O)c2)cc1] | 0.91 | | |
| C190 | 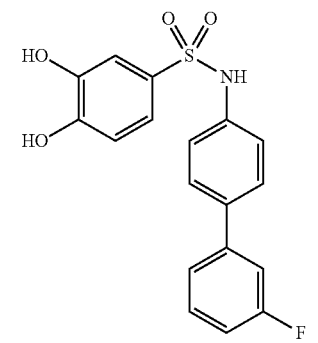 [SMILES: O=S(=O)(Nc1ccc(-c2cccc(F)c2)cc1)c1ccc(O)c(O)c1] | 9.70 | | |
| C198 | 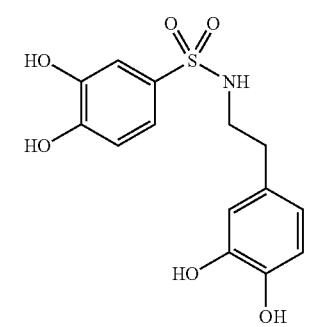 [SMILES: O=S(=O)(NCCc1ccc(O)c(O)c1)c1ccc(O)c(O)c1] | 0.051 | | |

TABLE 5-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C232 | 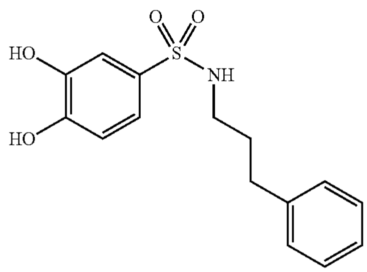 [SMILES: O=S(=O)(NCCCc1ccccc1)c1ccc(O)c(O)c1] | 13.3 | | |
| C233 | 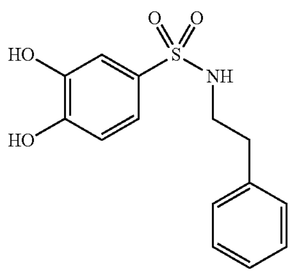 [SMILES: O=S(=O)(NCCc1ccccc1)c1ccc(O)c(O)c1] | 74.8 | | |
| C249 | 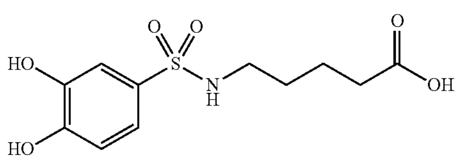 [SMILES: O=C(O)CCCCNS(=O)(=O)c1ccc(O)c(O)c1] | 663 | | |
| C270 | 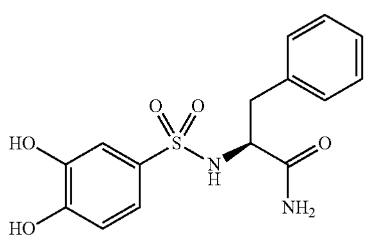 [SMILES: NC(=O)[C@H](Cc1ccccc1)NS(=O)(=O)c1ccc(O)c(O)c1] | 29.5 | | |
| C271 | 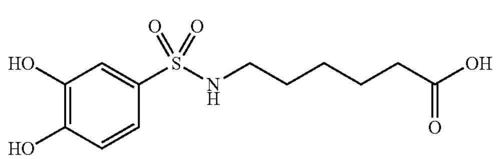 [SMILES: O=C(O)CCCCCNS(=O)(=O)c1ccc(O)c(O)c1] | 1.82 | | |
| C272 | 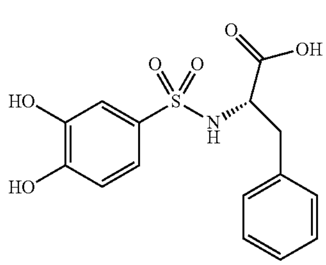 [SMILES: O=C(O)[C@H](Cc1ccccc1)NS(=O)(=O)c1ccc(O)c(O)c1] | 16.4 | | |

TABLE 5-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C273 | 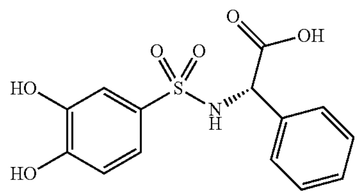 [SMILES: O=C(O)[C@@H](NS(=O)(=O)c1ccc(O)c(O)c1)c1ccccc1] | 55.6 | | |
| C274 | 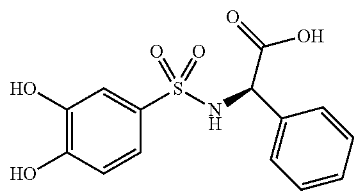 [SMILES: O=C(O)[C@H](NS(=O)(=O)c1ccc(O)c(O)c1)c1ccccc1] | 73.6 | | |
| C275 | 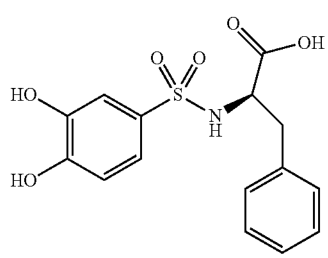 [SMILES: O=C(O)[C@@H](Cc1ccccc1)NS(=O)(=O)c1ccc(O)c(O)c1] | 30.5 | | |
| C303 | 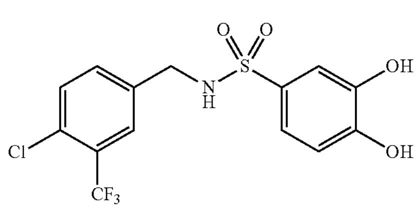 [SMILES: O=S(=O)(NCc1ccc(Cl)c(C(F)(F)F)c1)c1ccc(O)c(O)c1] | 12.6*, 13.6 | | |

TABLE 5-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C210 | 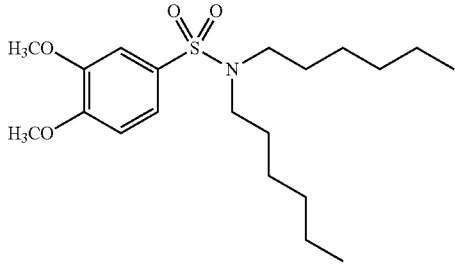 [SMILES: CCCCCCN(CCCCCC)S(=O)(=O)c1ccc(OC)c(OC)c1] | 189.6 | | |

*pH 7.4 was used.

Comparative compounds that do not demonstrate PAI-1 inhibitory activity in buffer (40 mM HEPES, 100 mM NaCl, 0.05% Tween-20, 10% DMSO, pH 7.8) in the assay described in Example 12 herein are depicted in Table 6.

TABLE 6

Synthesized Comparative Compounds

| No. | Structure |
|---|---|
| E169 | 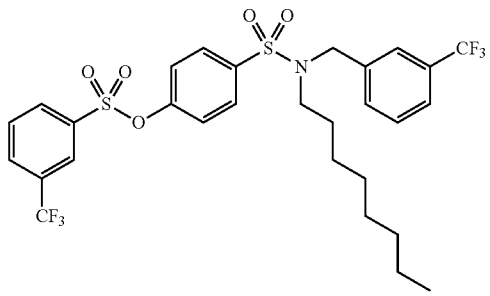 [SMILES: CCCCCCCCN(Cc1cccc(C(F)(F)F)c1)S(=O)(=O)c1ccc(OS(=O)(=O)c2cccc(C(F)(F)F)c2)cc1] |
| E178 | 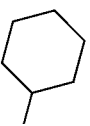 |
| E192 | 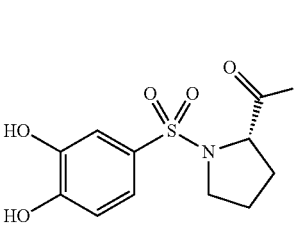 |

TABLE 6-continued

Synthesized Comparative Compounds

| No. | Structure |
|---|---|
| E194 | 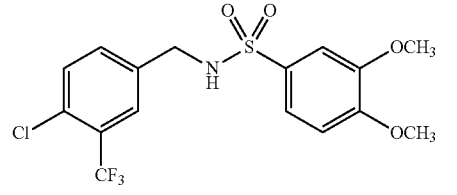 |

A comparative compound that does not demonstrate PAI-1 inhibitory activity in buffer (40 mM HEPES, 100 mM NaCl, 0.05% Tween-20, 10% DMSO, pH 7.4) in the assay described in Example 11 herein is depicted below.

E302

Exemplary compounds of the invention have a formula selected from C168, C176, C184, C185, C196, C156, C161, C200, C204, C236, and salts, esters, or prodrugs thereof. These compounds are depicted in Table 7 herein below.

TABLE 7
| | Synthesized PAI-1 Inhibitor Compounds | | | |
|---|---|---|---|---|
| No. | Structure | PAI-1/ uPA IC$_{50}$ (μM) | PAI-1/ tPA IC$_{50}$ (μM) | ATIII/ αIIa IC$_{50}$ (μM) |
| C168 | 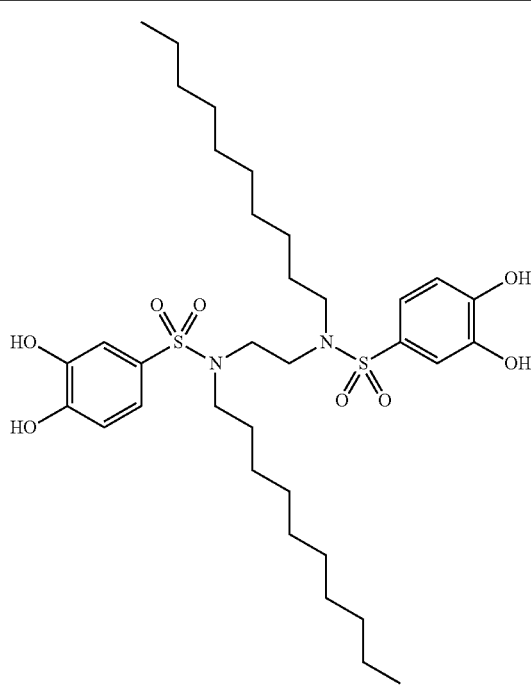 | | 1.98 | |
| C176 | 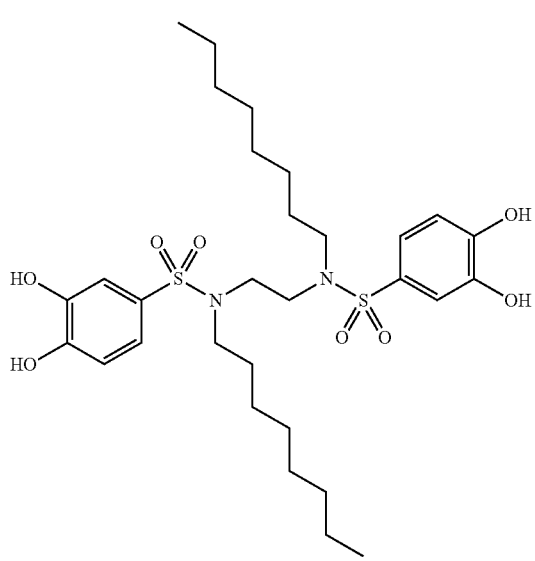 [SMILES: CCCCCCCCN(CCN(CCCCCCCC)S(=O)(=O)c1ccc(O)c(O)c1)S(=O)(=O)c1ccc(O)c(O)c1] | | 0.62 | |

TABLE 7-continued
Synthesized PAI-1 Inhibitor Compounds
| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C184 | 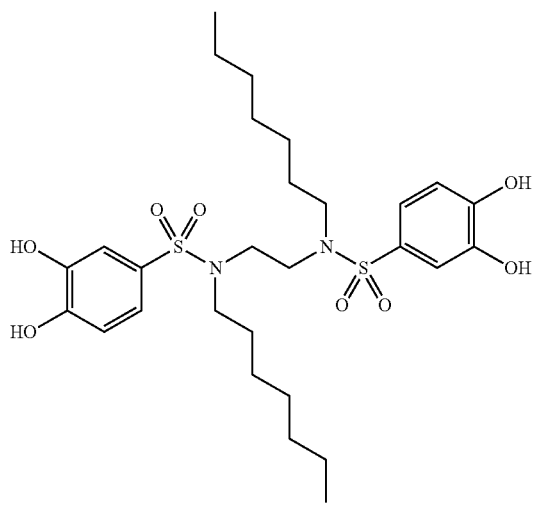 [SMILES: CCCCCCCN(CCN(CCCCCCC)S(=O)(=O)c1ccc(O)c(O)c1)S(=O)(=O)c1ccc(O)c(O)c1] | 0.59 | | |
| C185 | 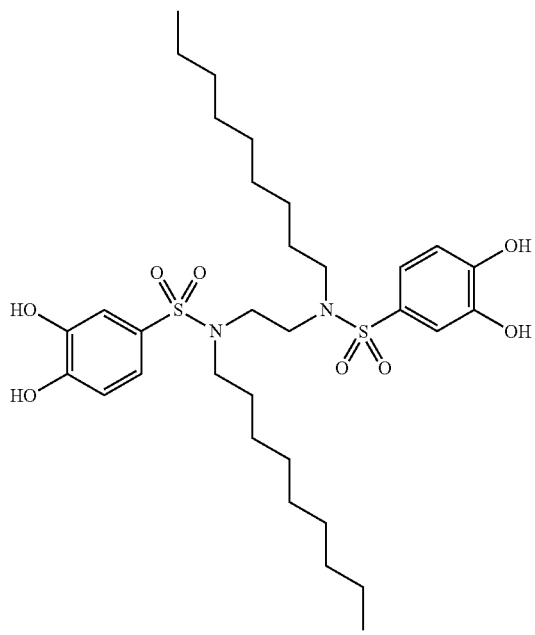 [SMILES: CCCCCCCCCN(CCN(CCCCCCCCC)S(=O)(=O)c1ccc(O)c(O)c1)S(=O)(=O)c1ccc(O)c(O)c1] | 0.42 | | |

TABLE 7-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C196 | 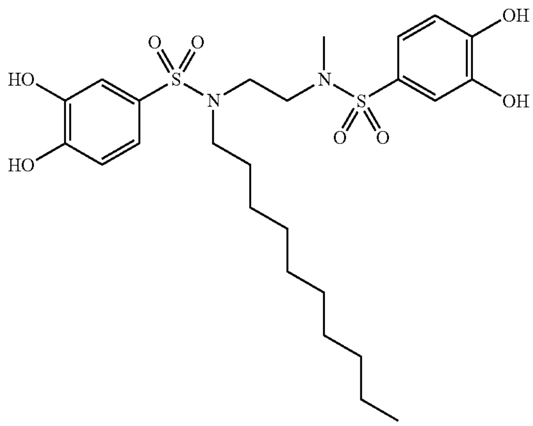 [SMILES: CCCCCCCCCCN(CCN(C)S(=O)(=O)c1ccc(O)c(O)c1)S(=O)(=O)c1ccc(O)c(O)c1] | 0.45 | | |
| C156 | 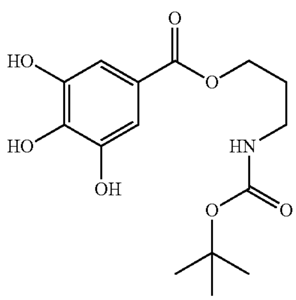 [SMILES: CC(C)(C)OC(=O)NCCCOC(=O)c1cc(O)c(O)c(O)c1] | 188.7 | 581.2 | |
| C161 | 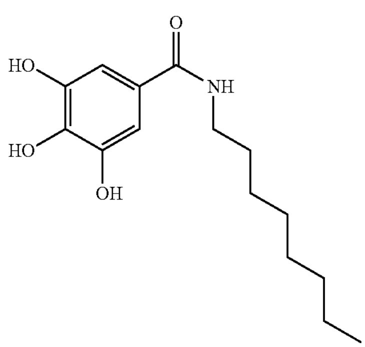 [SMILES: CCCCCCCCNC(=O)c1cc(O)c(O)c(O)c1] | 3.70 | 2.21 | 1670 |
| C200 | 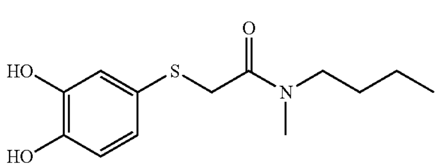 [SMILES: CCCCN(C)C(=O)CSc1ccc(O)c(O)c1] | 58.37 | | |

TABLE 7-continued

Synthesized PAI-1 Inhibitor Compounds

| No. | Structure | PAI-1/ uPA IC$_{50}$ (μM) | PAI-1/ tPA IC$_{50}$ (μM) | ATIII/ αIIa IC$_{50}$ (μM) |
|---|---|---|---|---|
| C204 | 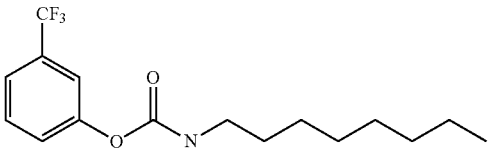 | 0.035 | | |
| C236 | 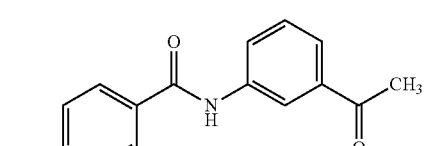 | 174 | | |

Comparative compounds that do not demonstrate PAI-1 inhibitory activity in buffer (40 mM HEPES, 100 mM NaCl, 0.05% Tween-20, 10% DMSO, pH 7.4) in the assay described in Example 11 herein are depicted in Table 8.

TABLE 8

Synthesized Comparative Compounds

| No. | Structure |
|---|---|
| E164 | 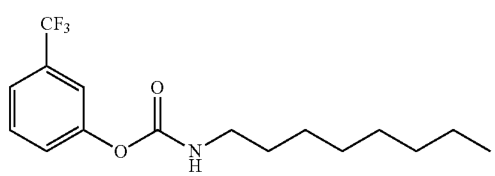 [SMILES: CCCCCCCCNC(=O)Oc1cccc(C(F)(F)F)c1] |
| E250 | 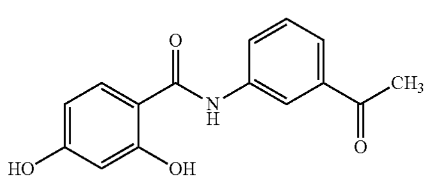 [SMILES: CC(=O)c1cccc(NC(=O)c2ccc(O)cc2O)c1] |
| E181 | 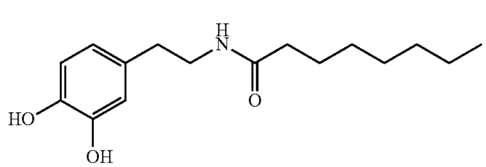 [SMILES: CCCCCCCC(=O)NCCc1ccc(O)c(O)c1] |
| E167 | |
| E166 | |

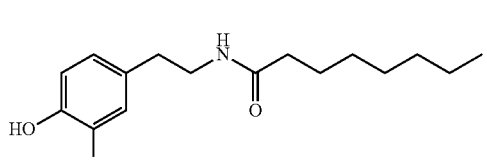

Compounds of the invention include those of formula XIII or a salt, ester, or prodrug thereof:

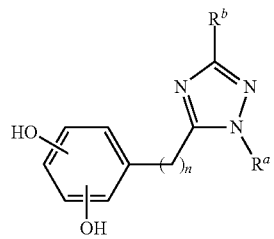

XIII wherein n is 0 or 1;

$R^a$ and $R^b$ are independently selected from the group consisting of $C_1$ to $C_{12}$ alkyl, $C_3$ to $C_6$ cycloalkyl, $(CH_2)_m$—$C_3$-$C_6$ cycloalkyl, $C_2$ to $C_6$ heterocycloalkyl, $(CH_2)_m$—$C_2$-$C_6$ heterocycloalkyl, $C_2$ to $C_6$ heterocycloalkyl, $(CH_2)_m$—$C_2$-$C_6$ heterocycloalkyl, benzyl, aryl, $(CH_2)_m$-aryl, heteroaryl, $(CH_2)_m$-heteroaryl, and substituted derivatives thereof; and m is 1, 2, 3, 4, 5, or 6.

In some embodiments, compounds of the invention include those of formula XIII as defined above wherein $R^a$ and $R^b$ are independently selected from the group consisting of butyl, pentyl, cyclopropyl, phenyl, difluorophenyl, and hydroxyphenyl.

Exemplary compounds of the invention have a formula selected from C201, C208, C213, C216, C220, C221, C222, C223, and salts, esters, or prodrugs thereof. These compounds are depicted in Table 9 herein below.

TABLE 9

| | Synthesized PAI-1 Inhibitor Compounds | |
|---|---|---|
| No. | Structure | PAI-1/ uPA $IC_{50}$ in buffer (μM) |
| C201 | | 181 |

TABLE 9-continued

| | Synthesized PAI-1 Inhibitor Compounds | |
|---|---|---|
| No. | Structure | PAI-1/ uPA $IC_{50}$ in buffer (μM) |
| C208 | | 77.2 |
| C213 | | |
| C216 | | |
| C220 | | 116.46 |

TABLE 9-continued

Synthesized PAI-1 Inhibitor Compounds

| No. | Structure | PAI-1/ uPA IC$_{50}$ in buffer (μM) |
|---|---|---|
| C221 | (structure) | 1608 |
| C222 | (structure) | 236 |
| C223 | (structure) | 124.6 |

Comparative compounds that do not demonstrate PAI-1 inhibitory activity in buffer (40 mM HEPES, 100 mM NaCl, 0.05% Tween-20, 10% DMSO, pH 7.8) in the assay described in Example 12 herein are depicted in Table 10.

TABLE 10

Synthesized Comparative Compounds

| No. | Structure |
|---|---|
| E202 | (structure) |
| E209 | (structure) |
| E211 | (structure) |
| E212 | (structure) |

TABLE 10-continued

Synthesized Comparative Compounds

| No. | Structure |
|---|---|
| E215 | 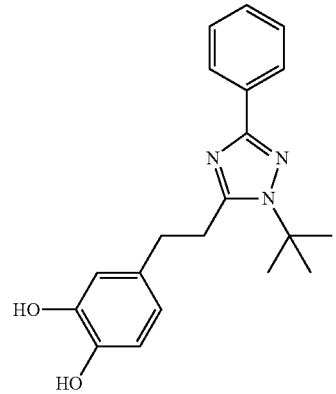 [SMILES: CC(C)(C)n1nc(-c2ccccc2)nc1CCc1ccc(O)c(O)c1] |
| E217 | 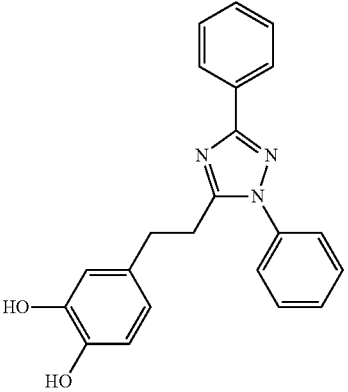 [SMILES: Oc1ccc(CCc2nc(-c3ccccc3)nn2-c2ccccc2)cc1O] |
| E218 | 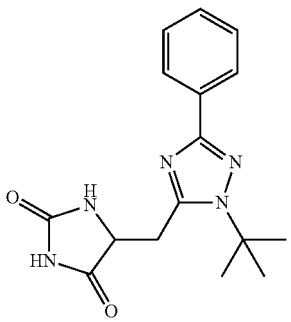 [SMILES: CC(C)(C)n1nc(-c2ccccc2)nc1CC1NC(=O)NC1=O] |
| E219 | 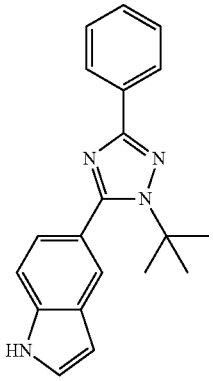 [SMILES: CC(C)(C)n1nc(-c2ccccc2)nc1-c1ccc2[nH]ccc2c1] |

TABLE 10-continued

Synthesized Comparative Compounds

| No. | Structure |
|---|---|
| E226 | 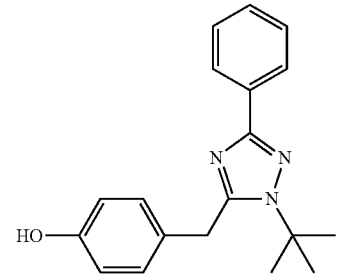 [SMILES: CC(C)(C)n1nc(-c2ccccc2)nc1Cc1ccc(O)cc1] |

Compounds of the invention include those of formula XIV or a salt, ester, or prodrug thereof:

XIV
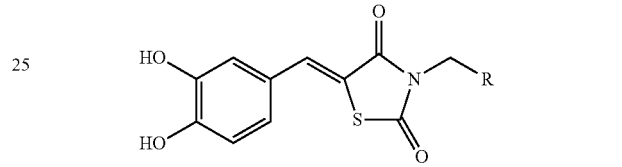

wherein R is selected from the group consisting of phenyl and substituted biphenyl.

Exemplary compounds of the invention have a formula selected from C199, C203, C206, C207, and salts, esters, or prodrugs thereof. These compounds are depicted in Table 11 herein below.

TABLE 11

Synthesized PAI-1 Inhibitor Compounds

| No. | Structure | PAI-1/ uPA IC$_{50}$ in buffer (μM) |
|---|---|---|
| C199 | 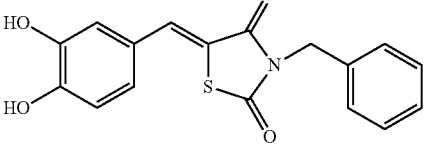 | 5.36 |
| C203 | 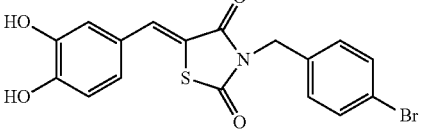 | 17.07 |
| C206 | 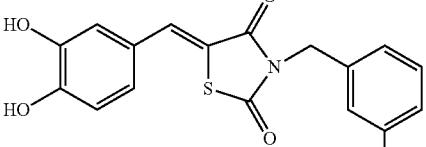 | 4.96 |

TABLE 11-continued

Synthesized PAI-1 Inhibitor Compounds

| No. | Structure | PAI-1/ uPA IC$_{50}$ in buffer (μM) |
|---|---|---|
| C207 | [structure: HO, HO-substituted benzylidene thiazolidinedione with N-benzyl-biphenyl-O-CF$_3$ substituent] | 16.83 |

Compounds of the invention include those of formula XV or a salt, ester, or prodrug thereof:

XV

[structure of formula XV]

wherein:

V is selected from the group consisting of (CH$_2$)$_n$, C$_3$ to C$_8$ cycloalkyl, (CH$_2$)$_n$—C$_3$-C$_8$ cycloalkyl-(CH$_2$)$_p$, aryl, (CH$_2$)$_n$-aryl-(CH$_2$)$_p$, heteroaryl, (CH$_2$)$_n$-heteroaryl-(CH$_2$)$_p$,

[structure showing a bis-benzoate ester linker]

and substituted derivatives thereof;

n and p are independently 0, 1, 2, 3, 4, 5, or 6;

X$_1$, X$_2$, X$_3$, X$_4$, X$_5$ and X$_6$ are independently selected from the group consisting of —H, —OH, —OR, —F, —Cl, —Br, —I, —NO$_2$, —NO, —N(R)$_2$, —N(R)$_3$$^+$, —C(O)R, —C(O)OR, —CHO, —C(O)NH$_2$, —C(O)SR, —CN, —S(O)$_2$R, —SO$_3$R, —SO$_3$H, —SO$_2$N(R)$_2$, —S=O, C$_1$ to C$_{12}$ alkyl, aryl, substituted aryl, heteroaryl, and substituted heteroaryl;

R is selected from the group consisting of C$_1$ to C$_6$ alkyl, C$_3$ to C$_6$ cycloalkyl, CH$_2$—C$_3$-C$_6$ cycloalkyl, phenyl, tolyl, and benzyl;

Y$_1$ is selected from the group consisting of O, NH, NR$^a$, S, and CH$_2$;

Y$_2$ is selected from the group consisting of O, NH, NR$^b$, S, and CH$_2$;

R$^a$ and R$^b$ are independently selected from the group consisting of C$_1$ to C$_{12}$ alkyl, C$_3$ to C$_6$ cycloalkyl, (CH$_2$)$_m$—C$_3$-C$_6$ cycloalkyl, C$_2$ to C$_6$ heterocycloalkyl, (CH$_2$)$_m$—C$_2$-C$_6$ heterocycloalkyl, benzyl, aryl, (CH$_2$)$_m$-aryl, heteroaryl, (CH$_2$)$_m$-heteroaryl, and substituted derivatives thereof;

m is 1, 2, 3, 4, 5, or 6; and

Z$_1$, Z$_2$, Z$_3$, and Z$_4$ are independently selected from the group consisting of C, P—OH, S, and S=O.

Compounds of the invention include those of formula XVI or a salt, ester, or prodrug thereof:

XVI

[structure of formula XVI]

wherein V, n, p, X$_1$, X$_2$, X$_3$, X$_4$, X$_5$, X$_6$, Y$_1$, Y$_2$, R$^a$, R$^b$, Z$_1$, Z$_2$, Z$_3$, and Z$_4$ are as defined above for formula XV.

Compounds of the invention include those of formula XVII or a salt, ester, or prodrug thereof:

XVII

[structure of formula XVII]

wherein:

X$_1$, X$_2$, X$_3$, X$_4$, X$_5$ and X$_6$ are independently selected from the group consisting of —H, —OH, —OR, —F, —Cl, —Br, —I, —NO$_2$, —NO, —N(R)$_2$, —N(R)$_3$$^+$, —C(O)R, —C(O)OR, —CHO, —C(O)NH$_2$, —C(O)SR, —CN, —S(O)$_2$R, —SO$_3$R, —SO$_3$H, —SO$_2$N(R)$_2$, —S=O, C$_1$ to C$_{12}$ alkyl, aryl, substituted aryl, heteroaryl, and substituted heteroaryl;

R is selected from the group consisting of C$_1$ to C$_6$ alkyl, C$_3$ to C$_6$ cycloalkyl, CH$_2$—C$_3$-C$_6$ cycloalkyl, phenyl, tolyl, and benzyl;

R$^b$ is selected from the group consisting of H, C$_1$ to C$_{12}$ alkyl, C$_3$ to C$_6$ cycloalkyl, (CH$_2$)$_m$—C$_3$-C$_6$ cycloalkyl, C$_2$ to C$_6$ heterocycloalkyl, (CH$_2$)$_m$—C$_2$-C$_6$ heterocycloalkyl, benzyl, aryl, (CH$_2$)$_m$-aryl, heteroaryl, (CH$_2$)$_m$-heteroaryl, and substituted derivatives thereof;

m is 1, 2, 3, 4, 5, or 6; and

Z$_4$ is selected from the group consisting of C, P—OH, S, and S=O.

Compounds of the invention include those of formula XVIII or a salt, ester, or prodrug thereof:

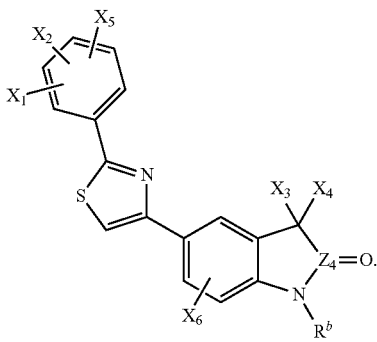

XVIII wherein X$_1$, X$_2$, X$_3$, X$_4$, X$_5$, X$_6$, R$^b$, and Z$_4$ are as defined above for formula XVII.

In some embodiments, compounds of the invention include those of formula XVII or XVIII as defined above wherein X$_1$ and X$_2$ are independently selected from —OH and —OR.

Compounds of the invention include those of formula XIX or a salt, ester, or prodrug thereof:

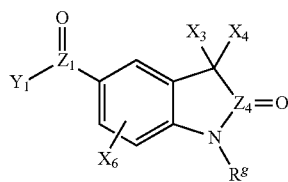

XIX wherein:

X$_3$, X$_4$, and X$_6$ are independently selected from the group consisting of —H, —OH, —OR, —F, —Cl, —Br, —I, —NO$_2$, —NO, —N(R)$_2$, —N(R)$_3$$^+$, —C(O)R, —C(O)OR, —CHO, —C(O)NH$_2$, —C(O)SR, —CN, —S(O)$_2$R, —SO$_3$R, —SO$_3$H, —SO$_2$N(R)$_2$, —S=O, aryl, substituted aryl, heteroaryl, and substituted heteroaryl;

R is selected from the group consisting of C$_1$ to C$_6$ alkyl, C$_3$ to C$_6$ cycloalkyl, CH$_2$—C$_3$-C$_6$ cycloalkyl, phenyl, tolyl, and benzyl;

Y$_1$ is selected from the group consisting of CHR$^a$R$^b$, OR$^a$, NHR$^a$, NR$^a$R$^b$, and SR$^a$;

R$^a$ and R$^b$ are independently selected from the group consisting of C$_1$ to C$_{12}$ alkyl, C$_3$ to C$_6$ cycloalkyl, (CH$_2$)$_m$—C$_3$-C$_6$ cycloalkyl, C$_2$ to C$_6$ heterocycloalkyl, (CH$_2$)$_m$—C$_2$-C$_6$ heterocycloalkyl, benzyl, aryl, (CH$_2$)$_m$-aryl, heteroaryl, (CH$_2$)$_m$-heteroaryl, —U, (CH$_2$)$_m$—U, and substituted derivatives thereof, or R$^a$ and R$^b$ taken together with the N atom to which they are bonded form a 3- to 8-membered heterocyclic ring;

U is selected from the group consisting of —NR$^c$R$^d$, —NR$^c$C(O)R$^e$, —NR$^c$C(O)OR$^e$, —NR$^c$C(O)NR$^f$R$^e$, —NR$^c$C(O)SR$^e$, —NR$^c$P(O)(OH)R$^e$, —NR$^c$P(O)(OH)OR$^e$, —NR$^c$P(O)(OH)NR$^f$R$^e$, —NR$^c$P(O)(OH)SR$^e$, —NR$^c$S(O)R$^e$, —NR$^c$S(O)OR$^e$, —NR$^c$S(O)NR$^f$R$^e$, —NR$^c$S(O)SR$^e$, —NR$^c$S(O)$_2$R$^e$, —NR$^c$S(O)$_2$OR$^e$, —NR$^c$S(O)$_2$NR$^f$R$^e$, —NR$^c$S(O)$_2$SR$^e$, —OR$^f$, —OC(O)R$^e$, —OC(O)OR$^e$, —OC(O)NR$^f$R$^e$, —OC(O)SR$^e$, —OP(O)(OH)R$^e$, —OP(O)(OH)OR$^e$, —OP(O)(OH)NR$^d$R$^e$, —OP(O)(OH)SR$^e$, —OS(O)R$^e$, —OS(O)OR$^e$, —OS(O)NR$^d$R$^e$, —OS(O)SR$^e$, —OS(O)$_2$R$^e$, —OS(O)$_2$OR$^e$, —OS(O)$_2$NR$^d$R$^e$, —OS(O)$_2$SR, —C(O)OR$^c$, —C(O)NR$^c$R$^d$, —C(O)SR$^c$, and —C(O)R$^c$;

R$^c$ and R$^d$ are independently selected from the group consisting of H, C$_1$ to C$_{12}$ alkyl, C$_1$ to C$_{12}$ haloalkyl, C$_3$ to C$_6$ cycloalkyl, (CH$_2$)$_m$—C$_3$-C$_6$ cycloalkyl, C$_2$ to C$_6$ heterocycloalkyl, (CH$_2$)$_m$—C$_2$-C$_6$ heterocycloalkyl, benzyl, aryl, (CH$_2$)$_m$-aryl, heteroaryl, (CH$_2$)$_m$-heteroaryl, and substituted derivatives thereof, or R$^c$ and R$^d$ taken together with the N atom to which they are bonded form a 3- to 8-membered heterocyclic ring;

R$^e$, R$^f$, and R$^g$ are independently selected from the group consisting of H, C$_1$ to C$_{12}$ alkyl, C$_1$ to C$_{12}$ haloalkyl, C$_3$ to C$_6$ cycloalkyl, (CH$_2$)$_m$—C$_3$-C$_6$ cycloalkyl, C$_2$ to C$_6$ heterocycloalkyl, (CH$_2$)$_m$—C$_2$-C$_6$ heterocycloalkyl, benzyl, aryl, (CH$_2$)$_m$-aryl, heteroaryl, (CH$_2$)$_m$-heteroaryl, and substituted derivatives thereof;

m is 1, 2, 3, 4, 5, or 6; and

Z$_1$ and Z$_4$ are independently selected from the group consisting of C, P—OH, S, and S=O.

Exemplary compounds of the invention have a formula selected from C225, C227, C228, C229, and salts, esters, or prodrugs thereof. These compounds are depicted in Table 12 herein below.

TABLE 12

Synthesized PAI-1 Inhibitor Compounds

| No. | Structure | PAI-1/ uPA IC$_{50}$ in buffer (μM) |
|---|---|---|
| C225 | 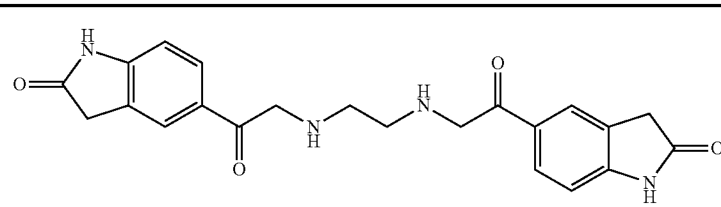 | 163 |

TABLE 12-continued

Synthesized PAI-1 Inhibitor Compounds

| No. | Structure | PAI-1/ uPA IC$_{50}$ in buffer (μM) |
|---|---|---|
| C227 | 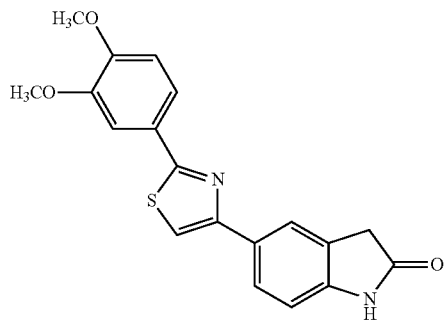 [SMILES: COc1ccc(-c2nc(-c3ccc4c(c3)CC(=O)N4)cs2)cc1OC] | 205 |
| C228 | 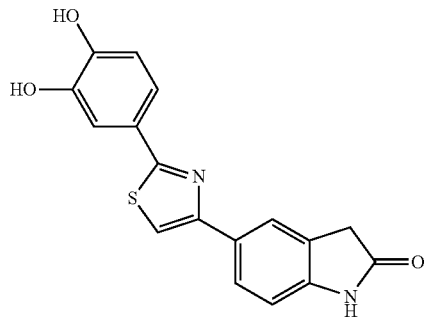 [SMILES: O=C1Cc2cc(-c3csc(-c4ccc(O)c(O)c4)n3)ccc2N1] | 14.8 |
| C229 | 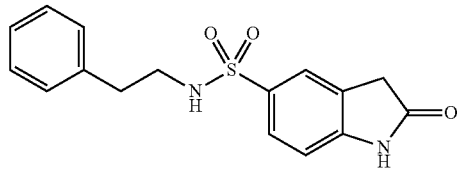 [SMILES: O=C1Cc2cc(S(=O)(=O)NCCc3ccccc3)ccc2N1] | 1288 |

Comparative compounds that do not demonstrate PAI-1 inhibitory activity in buffer (40 mM HEPES, 100 mM NaCl, 0.05% Tween-20, 10% DMSO, pH 7.4) in the assay described in Example 11 herein are depicted in Table 13.

TABLE 13

Synthesized Comparative Compounds

| No. | Structure |
|---|---|
| E230 | 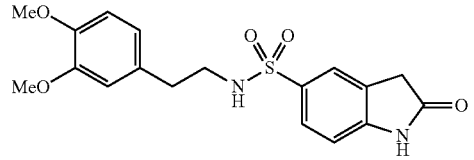 [SMILES: COc1ccc(CCNS(=O)(=O)c2ccc3c(c2)CC(=O)N3)cc1OC] |

TABLE 13-continued

Synthesized Comparative Compounds

| No. | Structure |
|---|---|
| E231 | 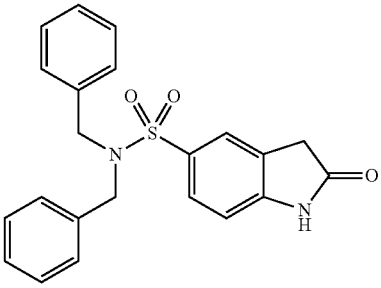 [SMILES: O=C1Cc2cc(S(=O)(=O)N(Cc3ccccc3)Cc3ccccc3)ccc2N1] |

TABLE 13-continued

Synthesized Comparative Compounds

| No. | Structure |
|---|---|
| E315 | 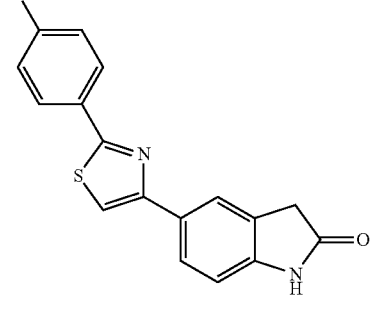 |
| E316 | 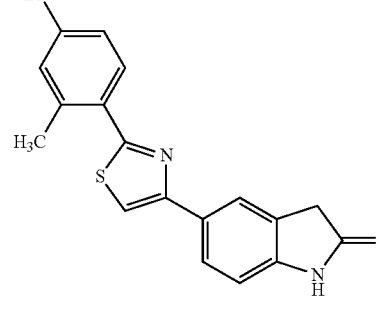 |
| E317 | 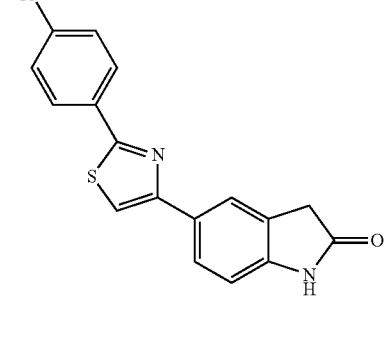 |
| E318 | 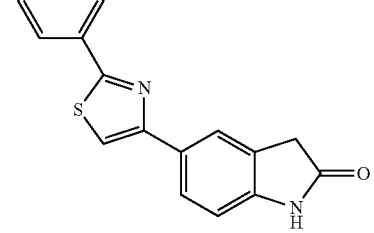 |

Compounds for use in the methods of the invention include those of formula XX to XXIX or a salt, ester, or prodrug thereof. Compounds of formula XX to XXIX that demonstrate PAI-1 inhibitory activity are depicted in Table 14.

TABLE 14

PAI-1 Inhibitor Compounds

| Compound No. | Structure | Supplier |
|---|---|---|
| XX | 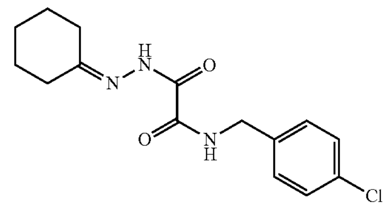 [SMILES: O=C(NCc1ccc(Cl)cc1)C(=O)NN=C1CCCCC1] | Chembridge |
| XXI | 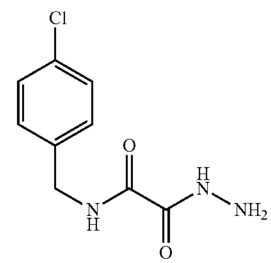 [SMILES: NNC(=O)C(=O)NCc1ccc(Cl)cc1] | Synthon Labs |
| XXII | 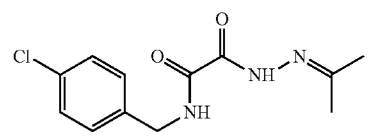 [SMILES: CC(C)=NNC(=O)C(=O)NCc1ccc(Cl)cc1] | Vitas M Labs |
| XXIII | 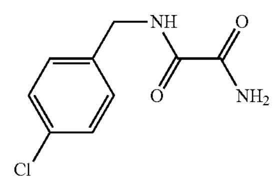 [SMILES: NC(=O)C(=O)NCc1ccc(Cl)cc1] | Chembridge |
| XXIV | 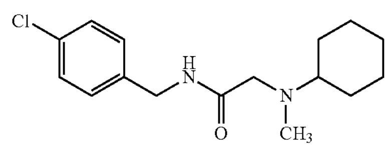 [SMILES: CN(CC(=O)NCc1ccc(Cl)cc1)C1CCCCC1] | Chembridge |
| XXV | 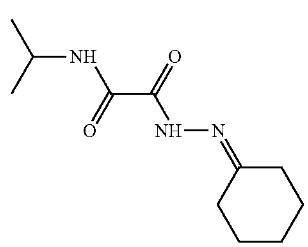 [SMILES: CC(C)NC(=O)C(=O)NN=C1CCCCC1] | Chembridge |
| XXVI | 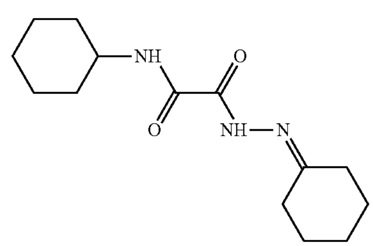 [SMILES: O=C(NN=C1CCCCC1)C(=O)NC1CCCCC1] | Chembridge |

TABLE 14-continued

PAI-1 Inhibitor Compounds

| Compound No. | Structure | Supplier |
|---|---|---|
| XXVII | (structure) | Synthon Labs |
| XXVIII | (structure) | Synthon Labs |
| XXIX | (structure) | Enamine |

Methods of Making Inhibitors of PAI-1 Activity

The compounds of the present invention can be readily prepared according to the following reaction schemes or modification thereof using readily available starting materials, reagents and conventional synthetic procedures. It is also possible to make use of variants of these process steps, which in themselves are known to and well within the preparatory skill of the medicinal chemist.

Derivatives of PAI-1 inhibitors are also included herein. Such derivatives include molecules modified by one or more water soluble polymer molecules, such as polyethylene glycol, or by the addition of polyamino acids, including fusion proteins (procedures for which are well-known in the art). Such derivatization may occur singularly or there may be multiple sites of derivatization.

Primary High-Throughput Screen for PAL-1 Inhibition

High-throughput screening was carried out using the protocol described below. All screening was performed in the Center for Chemical Genomics in the Life Sciences Institute at the University of Michigan. For assay validation, the Microsource Spectrum 2000 was screened both in HEPES-buffered saline (HBS) and in HBS containing 15 mg/mL BSA. All other libraries were screened in HBS with 15 mg/mL BSA only. Purified compound libraries screened were the NIH Clinical Collection, Chemical Methodologies Libraries Development (Boston University), Maybridge, Chembridge, ChemDiv, National Cancer Institute-Development Therapeutics Program Library, the Cayman Cannabinoid and Epigenetics collections, EMD Protein Kinase collection, and the Enzo Autophagy, Protease, Natural products, REDOX, and Wnt Pathway libraries. Together, these libraries totaled approximately 152,899 purified compounds. For primary screening, all reagents except for compounds were added using a Thermo Scientific Multidrop Combi.

Briefly, 6 µL of 15 nM PAI-1 in 15 mg/mL BSA was added per well, followed by addition of 200 nL of compound using a Beckman Biomek FX with a pin-tool attachment liquid handling system. One compound was added per well, yielding a compound concentration of approximately 32 µM (3.2% DMSO) in the presence of PAI-1. Following a 15-minute incubation, 3 µL of 15 nM uPA in HEPES-buffered saline (HBS) was added per well, for final concentrations of PAI-1 and uPA of 10 nM and 5 nM, respectively. A 2:1 PAI-1:uPA ratio was chosen to enrich for the most active compounds, as greater than half of the PAI-1 must be inactivated before a signal is generated. After an additional 15-minute incubation, 3 µL of the pNA/AMC substrate mixture was added in HBS to yield final concentrations of 200 µM and 100 µM, respectively. The mixture of uPA and substrates in the absence of PAI-1 served as a positive control, while the negative control consisted of the mixture uPA and substrates along with PAI-1. Following a 90-minute incubation to allow for substrate turnover, quenching of WPF by pNA (ex/em 430/470 nm) and AMC fluorescence (ex/em 380/470) were recorded using a BMG Labtech Pherastar plate reader. All data was analyzed using Tripos Benchware Dataminer.

Using this HTS protocol, 152,899 purified compounds were screened from 15 different collections in the Center for Chemical Genomics (CCG) at the University of Michigan. Compounds were considered PAI-1 inactivators if a change in both the pNA and AMC signals was observed that was greater than three standard deviations (>3SD) from the negative control. Compounds that displayed a change in only one of the reporter signals were classified as false-positives and not considered for further evaluation. The average Z-factor values (Z'), which serve as a statistical gauge for the quality of the HTS assay, for pNA and AMC were 0.72 and 0.68, respectively, indicating that the pNA/AMC dual-reporter system is a statistically excellent assay.

Because the pNA and AMC fluorescence reads were recorded individually, the data from each signal was also compared separately to explore the hit rates using pNA or AMC versus the dual-reporter system. Interestingly, a significantly high hit rate was observed for each reporter alone. Analysis of the AMC reporter alone revealed that 20.3% of compounds displayed a change in signal greater than 3SD from the negative control, exemplifying an high hit rate for a primary screen and portraying the difficulty in triaging compounds for confirmation and follow-up. For the pNA reporter only, the hit rate was lower relative to AMC, but also high at 8.7%. Upon applying both signals for the hit criteria, the overall hit rate was significantly reduced to 1.5% (2,363 compounds), indicating a reduction in the false-positive rate of 7.2-18.8%, depending upon which single reporter was used. Together, these HTS results demonstrate the usefulness and efficiency of applying a dual-reporter system for ruling out false-positives compared to a single reporter assay.

Confirmation and Dose-Response Testing for PAI-1 Inhibition

Confirmation testing for purified compounds was performed as described for the primary assay except that compounds were stamped in triplicate. In addition, a 'pre-read' was recorded after addition of PAI-1, compound and uPA, but prior to substrate mixture addition. Compounds that showed a change in pNA and AMC signals >3SD in at least 2 out of 3 wells were further examined. Of this subset, only compounds that showed <3SD change in signal in 2 or less wells relative to the negative control in the pre-read were chosen for dose-response testing. Based on these criteria, 300 compounds were chosen for dose-response testing in the CCG. For this analysis, varying volumes (29-600 nL) of compound were stamped in duplicate using a TTP Labtech Mosquito X1 liquid handling system, resulting in an approximate final concentration of 12-250 µM. Development was carried out as described for the primary screen.

Methods of Using PAI-1 Inhibitors

As mentioned herein above, it is contemplated that methods of the invention include treating a disease or disorder associated with elevated levels of PAI-1 comprising administering a PAI-1 inhibitor. In one aspect, the subject is a mammal. In a preferred aspect, the mammalian subject is human.

In one embodiment, the invention includes PAI-1 inhibitor compounds and methods of using the compounds in the treatment of many diseases or disorders associated with PAI-1 activity. Such conditions, e.g., diseases or disorders, include, but are not limited to, dysregulation of lipid metabolism, obesity, diabetes, polycystic ovary syndrome, bone loss induced by estrogen deficiency, fibrosis and fibrotic disease, inflammation, cell migration and migration-driven proliferation of cells, and angiogenesis or thrombosis. In one aspect, such inhibitors are also contemplated to be useful for modulation of endogenous fibrinolysis, and in conjunction with pharmacologic thrombolysis. In another aspect, the invention includes PAI-1 inhibitor compounds and methods of using the compounds in the treatment of acute diseases associated with high PAI-1 levels, such as, but not limited to, sepsis, myocardial infarction, and thrombosis, compared to PAI-1 levels in normal subjects known not to suffer from sepsis, myocardial infarction, or thrombosis. In another aspect, the PAI-1 inhibitor compounds of the invention are used in methods for treating diseases and disorders associated with high PAI-1 levels, such as, but not limited to, cancer, atherosclerosis, insulin resistance, type 2 diabetes, and fibrotic diseases compared to PAI-1 levels in normal subjects known not to suffer from these diseases or disorders. In another aspect, the invention includes PAI-1 inhibitor compounds for regulating lipid metabolism, including increasing circulating HDL and/or decreasing circulating VLDL in a subject.

In various aspects, a PAI-1 inhibitor is useful in the treatment of any condition, including a disease or disorder, wherein the lowering of PAI-1 levels will provide benefits. The PAI-1 inhibitor is useful alone, or in combination with other compounds, which may act as to promote the reduction of PAI-1 levels.

One of the therapeutic embodiments of the invention is the provision, to a subject in need thereof, compositions comprising one or more PAI-1 inhibitor. In one aspect, the PAI-1 inhibitor is isolated from a known compound or is chemically synthesized. In another aspect, the PAI-1 inhibitor formulation for therapy in a subject is selected based on the route of administration and in certain aspects includes liposome and micelle formulations as well as classic pharmaceutical preparations.

The PAI-1 inhibitor is formulated into an appropriate preparation and administered to one or more sites within the subject in a therapeutically effective amount. In one embodiment, the PAI-1 inhibitor-based therapy is effected via continuous or intermittent intravenous administration. In one aspect, the PAI-1 inhibitor-based therapy is effected via continuous or intermittent intramuscular or subcutaneous administration. In another aspect, the PAI inhibitor-based therapy is effected via oral or buccal administration. By "effective amount" the invention refers to an amount of PAI-1 inhibitor compound that is sufficient to support an observable change in the level of one or more biological activities of PAI-1, plasminogen activator, HDL, LDL, or VLDL and/or an observable change in an indication for which the method of treatment is intended. The change may be reduced level of PAI-1 activity. In one aspect, the change is an increase in plasminogen activator, and/or HDL and/or a reduction in LDL and VLDL.

In various aspects, administration of the compositions is systemic or local, and in still other aspects comprises a single site injection of a therapeutically-effective amount of the PAI-1 inhibitor composition. Any route known to those of skill in the art for the administration of a therapeutic composition of the invention is contemplated including, for example, intravenous, intramuscular, subcutaneous, oral, or a catheter for long-term administration.

Alternatively, it is contemplated that the therapeutic composition is delivered to the patient at multiple sites. The multiple administrations are rendered simultaneously or are administered over a period of several hours. It is likewise contemplated that the therapeutic composition is taken on a regular basis via oral administration. In certain cases, it is beneficial to provide a continuous flow of the therapeutic composition. Additional therapy is administered on a period basis, for example, daily, weekly, or monthly.

In addition to therapies based solely on the delivery of the PAI-1 inhibitor composition, combination therapy is specifically contemplated. In the context of the invention, it is contemplated that the PAI-1 inhibitor composition therapy is used similarly in conjunction with other agents commonly used for the treatment of elevated levels of PAI-1, LDL and VLDL.

To achieve the appropriate therapeutic outcome, using the methods and compositions of the invention, one would generally provide a composition comprising a PAI-1 inhibitor and at least one other therapeutic agent (second therapeutic agent). In one aspect of the invention, it is contemplated that methods include administration or inclusion of at least one additional factor or other drug. Such drugs include drugs used to manage cardiovascular disease including, but not limited to, cholesterol lowering drugs, such as statins, anti-inflammatories, and ACE inhibitors. Such drugs also include drugs targeting neurological disorders including, but not limited to drugs for targeting stroke, seizures, and Alzheimer's Disease. In another aspect, the additional drugs include, but are not limited to, drugs targeting diabetes. These are all disorders associated with elevated levels of PAI-1 and, therefore, it is contemplated that combination therapy may be used with PAI-1 inhibitors and other known therapies.

The combination therapy compositions are provided in a combined amount effective to produce the desired therapeutic outcome in the treatment of increased levels of PAI-1, VLDL, or LDL and/or make a detectable change in an indication as described herein. This process involves administering the PAI-1 inhibitor and the second agent(s) or factor(s) at the same time. Methods thus include administering a single composition or pharmacological formulation that includes both agents, or administering two distinct compositions or formulations, at the same time, wherein one composition includes the PAI-1 inhibitor therapeutic composition and the other includes the second therapeutic agent.

Alternatively, the PAI-1 inhibitor treatment precedes or follows the second therapeutic agent treatment by intervals ranging from minutes to weeks. In embodiments where the second therapeutic agent and the PAI-1 inhibitor are administered separately, one generally ensures that a significant period of time did not expire between the times of each delivery, such that the second therapeutic agent and the PAI-1 inhibitor are able to exert an advantageously combined effect. In such instances, it is contemplated that one administers both modalities within about 12-24 hours of each other, or alternately, within about 6-12 hours of each other, or alternately, with a delay time of only about 12 hours. In some situations, it is desirable to extend the time period for treatment significantly, however, where several days (2, 3, 4, 5, 6 or 7) to several weeks (1, 2, 3, 4, 5, 6, 7 or 8) lapse between the respective administrations.

Systemic delivery of PAI-1 inhibitors to patients is a very efficient method for delivering a therapeutically effective amount of the compound to counteract the immediate clinical manifestations of a disease or disorder. Alternatively, local delivery of the PAI-1 inhibitor and/or the second therapeutic agent is appropriate in certain circumstances. In a certain embodiment, it is contemplated that the PAI-1 inhibitor is delivered to a patient for an extended period of time. It is further contemplated that the PAI-1 inhibitor is taken throughout a patient's lifetime to lower PAI-1, VLDL and/or LDL levels.

Pharmaceutical Compositions

As mentioned herein above, the invention also comprehends methods using pharmaceutical compositions comprising effective amounts of PAI-1 inhibitor together with pharmaceutically acceptable diluents, preservatives, solubilizers, emulsifiers, adjuvants and/or carriers useful in PAI-1 inhibitor therapy. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., thimersol, benzyl alcohol), and bulking substances (e.g., lactose, mannitol); incorporation of the material into particulate preparations of polymeric compounds, such as polylactic acid, polyglycolic acid, etc., or in association with liposomes or micelles. Such compositions will influence the physical state, stability, rate of in vivo release, and rate of in vivo clearance of the PAI-1 inhibitor. See, e.g., Remington's Pharmaceutical Sciences, 18th Ed. (1990) Mack Publishing Co., Easton, Pa., pages 1435-1712, which are herein incorporated by reference.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. In one aspect, the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physician's direction. For example, unit dosages may be made up in packeted powders, vials or ampoules and, in one aspect, in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patient's recovery rate.

The precise dosage to be employed depends upon several factors including the host, whether in veterinary medicine or human medicine, the nature and severity of the condition, e.g., disease or disorder, being treated, the mode of administration and the particular active substance employed. The compounds may be administered by any conventional route, in particular enterally, and, in one aspect, orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

PAI-1 inhibitors or derivatives thereof may be formulated for injection, or oral, nasal, pulmonary, topical, or other types of administration as one skilled in the art will recognize. The formulation may be liquid or may be solid, such as lyophilized, for reconstitution.

PAI-1 inhibitor or derivatives thereof are useful in the treatment of any of the acute or chronic diseases or disorders associated with increased levels of PAI-1, LDL, or VLDL. Conditions (e.g., diseases or disorders) alleviated or modulated by the administration of PAI-1 inhibitor, in some aspects, are those characterized by increased levels of VLDL and LDL. Such conditions may be induced as a course of therapy for other purposes, such as chemotherapy or radiation therapy. It is contemplated that such conditions may result from genetic inheritance or be the side effect of another condition or medication.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the vectors or cells of the invention, its use in therapeutic compositions is contemplated. Supplementary active ingredients also can be incorporated into the compositions.

The active compositions used in the methods of the invention include classic pharmaceutical preparations. Administration of these compositions according to the invention will be via any common route so long as the target tissue is available via that route. The pharmaceutical compositions may be introduced into the subject by any conventional method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents (for example, sugars or sodium chloride). Prolonged absorption of the injectable compositions can be brought about by the use in the compositions of agents delaying absorption (for example, aluminum monostearate and gelatin).

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients also can be incorporated into the compositions.

For oral administration of the compositions used in the methods of the invention, a PAI-1 inhibitor may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions used in the methods of the invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions used in the methods of the invention may be formulated in micelles or liposomes. Such formulations include sterically stabilized micelles or liposomes and sterically stabilized mixed micelles or liposomes. Such formulations can facilitate intracellular delivery, since lipid bilayers of liposomes and micelles are known to fuse with the plasma membrane of cells and deliver entrapped contents into the intracellular compartment.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

Generally, an effective amount of a PAI-1 inhibitor, or derivatives thereof, will be determined by the age, weight, and condition or severity of disease or disorder of the recipient. See, Remington's Pharmaceutical Sciences, supra, pages 697-773, herein incorporated by reference. Typically, a dosage of between about 0.001 µg/kg body weight/day to about 1000 µg/kg body weight/day, may be used, but more or less, as a skilled practitioner will recognize, may be used. Dosing may be one or more times daily, or less frequently, and may be in conjunction with other compositions as described herein. It should be noted that the invention is not limited to the dosages recited herein.

By initiating the treatment regimen with a minimal daily dose of about one gram, the blood levels of PAI-1 and the patient's symptomatic relief analysis may be used to determine whether a larger dose is indicated. One skilled in the art will appreciate that the appropriate dosage levels for treatment will thus vary depending, in part, upon the molecule delivered, the indication for which the PAI-1 inhibitor compound is being used, the route of administration, and the size (body weight, body surface or organ size) and condition (the age and general health) of the patient. Accordingly, the clinician may titer the dosage and may modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

"Unit dose" is defined as a discrete amount of a therapeutic composition dispersed in a suitable carrier. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, supra, pages 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

Appropriate dosages may be ascertained through the use of established assays for determining level of myocardial infarct in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment.

It will be appreciated that the pharmaceutical compositions and treatment methods of the invention are useful in fields of human medicine and veterinary medicine. Thus the subject to be treated is in one aspect a mammal. In another aspect, the mammal is a human.

In addition, the invention contemplates a kit containing components comprising a composition comprising a PAI-1 inhibitor; and optionally, at least one additional factor useful in the treatment of the acute and chronic diseases and disorders discussed herein.

Uses of Compounds of the Invention in the Treatment of Diseases or Disorders

The invention includes the use of compounds of the invention for the production of a medicament for the treatment or prevention of any disease or disorder discussed herein.

The compounds of the invention are inhibitors of the serine protease inhibitor PAI-1, and are therefore useful in the treatment or prophylaxis of those processes which involve the production and/or action of PAI-1. Thus, the compounds of the invention, in various aspects, are useful in preventing or reducing thrombosis, promoting thrombolysis, reducing fibrosis regulating lipid metabolism as described herein. In one aspect, the compounds of the invention are useful in treating high cholesterol and diseases or disorders associated with elevated levels of PAI-1. In another aspect, the compounds of the invention are useful in treating elevated levels of VLDL or LDL. In another aspect, the compounds of the invention are useful in elevating HDL.

In one aspect, the invention includes the uses of these inhibitors for the treatment of many diseases or disorders associated with PAI-1 activity. Such diseases or disorders include, but are not limited to, inflammation, cell migration and migration-driven proliferation of cells, and angiogenesis or thrombosis. Such inhibitors are also contemplated to be useful for modulation of endogenous fibrinolysis, and in conjunction with pharmacologic thrombolysis.

The compounds of the invention are useful in the treatment or prevention of insulin resistance, obesity, non-insulin dependent diabetes mellitus, cardiovascular disease, thrombotic events associated with coronary artery and cerebrovascular disease. The compounds of the invention are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint replacement), and peripheral arterial occlusion. These compounds are also useful in treating stroke associated with or resulting from atrial fibrillation.

The compounds of the invention are also used in the treatment or prophylaxis of high cholesterol and diseases or disorders associated with such a condition.

The compounds of the invention may also be used in the treatment of diseases or disorders associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be used in the treatment of malignancies, and diseases or disorders associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation.

The compounds of the invention may also be used in the treatment of Alzheimer's disease. This method may also be characterized as the inhibition of plasminogen activator by PAI-1 in a mammal, particularly a human, experiencing or subject to Alzheimer's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor-containing highly active antiretroviral therapy (HAART) for the treatment of diseases or disorders which originate from fibrinolytic impairment and hypercoagulability of HIV-1 infected patients receiving such therapy.

The compounds of the invention may be used for the treatment of diabetic nephropathy and renal dialysis associated with nephropathy.

The compounds of the invention may be used to treat cancer, septicemia, proliferative diseases, such as psoriasis, improving coagulation homeostasis, cerebrovascular diseases, microvascular disease, hypertension, dementia, atherosclerosis, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, fibrinolytic disorder, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, deep vein thrombosis, pulmonary embolism, reducing the risk of undergoing a myocardial revascularization procedure, microvascular diseases such as nephropathy, neuropathy, retinopathy and nephrotic syndrome, hypertension, Type 1 and 2 diabetes and related diseases, obesity, insulin resistance, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

The compounds in the invention can be used in the treatment of inflammatory diseases, septic shock and the vascular damage associated with infections and for the treatment of blood and blood products used in dialysis, blood storage in the fluid phase, especially ex vivo platelet aggregation. The compounds in the present invention may also be used in combination with prothrombolytic, fibrinolytic and anticoagulant agents. The present compounds may also be added to human plasma during the analysis of blood chemistry in hospital settings to determine the fibrinolytic capacity thereof.

This invention further comprises methods for treating, preventing, ameliorating or inhibiting each of the maladies mentioned herein in a mammal, in one aspect, in a human, the method(s) each comprising administering to a mammal in need of such treatment, prevention, amelioration or inhibition a pharmaceutically or therapeutically effective amount of a compound of this invention, or a pharmaceutically acceptable salt, ester, or prodrug form thereof.

The compounds of the invention may also be used to treat cancer including, but not limited to, breast and ovarian cancer, and as imaging agents for the identification of metastatic cancers.

It will be understood that a pharmaceutically or therapeutically effective amount of a compound herein refers to an amount of the compound in question which will sufficiently inhibit the serine protease inhibitor PAI-1 in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

EXAMPLES

The invention is described in more detail with reference to the following non-limiting examples, which are offered to more fully illustrate the invention, but are not to be construed as limiting the scope thereof. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

As discussed herein above, elevated levels of PAI-1 have been implicated in a variety of diseases and disorders. The development of therapeutic agents that act as selective inhibitors of PAI-1 may provide an approach to treat these diseases and disorders. The design and synthesis of a variety of compounds and their structure:activity relationship with PAI-1 is described. Additional synthetic methods for obtaining PAI-1 inhibitors are disclosed in US 2010/0137194, which is incorporated by reference in its entirety.

Example 1—Synthesis of Compounds of Formula III

General Procedure A

Compounds of formula III were synthesized according to the procedure described below and as shown in the following scheme:

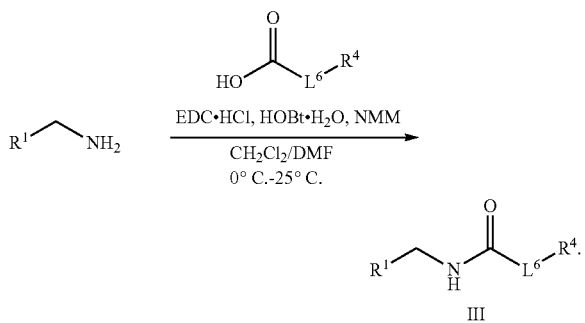

To a 0° C. solution of an appropriately-substituted carboxylic acid (1 equiv.), an appropriately-substituted amine (1.2 equiv.), N-methylmorpholine (1 equiv.), and HOBT.H$_2$O (1 equiv.) in 2.5:1 dry CH$_2$Cl$_2$ and DMF, EDC.HCl (1 equiv.) was added in portions. The resulting slurry was allowed to warm to room temperature overnight with stirring. The reaction mixture was concentrated by rotary evaporation, diluted with a 4:1 solution of EtOAc and hexane, washed with 0.1N HCl (2×), saturated NaHCO3 (2×), and brine (2×). The organic phase was dried with anhydrous MgSO$_4$ and concentrated in vacuo. The resultant solid was triturated with chloroform and the solid obtained after filtration was dried in vacuo, which afforded compounds of formula III.

Synthesis of N-(4-chloro-3-(trifluoromethyl)benzyl)-3-(3,4-dihydroxyphenyl)propanamide (compound C330)

N-(4-chloro-3-(trifluoromethyl)benzyl)-3-(3,4-dihydroxyphenyl)propanamide (compound C330) was synthesized according to General Procedure A. To a 0° C. solution of 3,4-dihydroxyhydro cinnamic acid (205.8 mg, 1.13 mmol), 4-chloro-3-(trifluoromethyl)benzylamine (0.2 mL, 1.36 mmol), N-methylmorpholine (0.12 mL, 1.13 mmol) and HOBT.H$_2$O (173.0 mg, 1.13 mmol) in 5 mL of dry CH$_2$Cl$_2$ and 2 mL of DMF, EDC.HCl (216.6 mg, 1.13 mmol) was added in portions. The resulting slurry was allowed to warm to room temperature overnight with stirring. The reaction mixture was concentrated by rotary evaporation, diluted with 30 mL of a 4:1 solution of EtOAc and hexane, washed with 0.1N HCl (2×), saturated NaHCO3 (2×), and brine (2×). The organic phase was dried with anhydrous MgSO₄ and concentrated in vacuo. The resultant solid was triturated with chloroform and the solid obtained after filtration was dried in vacuo, which afforded 235 mg (48%) of product as a pale yellow crystalline solid. $^{1}$H NMR (DMSO-d₆, 400 MHz) δ 8.66 (s, 1H), 8.59 (s, 1H), 8.35 (t, J=6.0 Hz, 1H), 7.66 (s, 1H), 7.57 (d, J=8.2 Hz, 1H), 7.31 (d, J=8.2 Hz, 1H), 6.57 (d, J=8.2 Hz, 1H), 6.54 (d, J=1.8 Hz, 1H), 6.39 (dd, J=1.8, 8.2 Hz, 1H), 4.27 (d, J=6.0 Hz, 2H), 2.62 (t, J=7.8 Hz, 2H), 2.33 (t, J=7.7 Hz, 2H). $^{13}$C NMR (DMSO-d₆, 100 MHz) δ 172.32, 145.53, 143.89, 140.46, 133.24, 132.45, 131.99, 129.25, 126.99 (q, J=5.7 Hz), 126.53 (q, J=30.5 Hz), 125.96, 123.41 (q, J=270.8 Hz), 119.30, 116.29, 115.92, 41.54, 37.90. HRMS, DART calcd. for $C_{17}H_{15}F_3NO_3Cl$ [M+H]⁺ 374.07707. found: 374.07880.

The following compounds also were synthesized according to General Procedure A: C279, C286, C330, C344, C345, C346, C347, C348, C356, C357, C358, C359, C360, C361, C363, C364.

Synthesis of N-(4-chloro-3-(trifluoromethyl)benzyl)-5-oxo-4,5-dihydro-1,3,4-oxadiazole-2-carboxamide (compound C285)

N-(4-Chloro-3-(trifluoromethyl)benzyl)-5-oxo-4,5-dihydro-1,3,4-oxadiazole-2-carboxamide (C285) was synthesized according to the procedure described below and as shown in the following scheme:

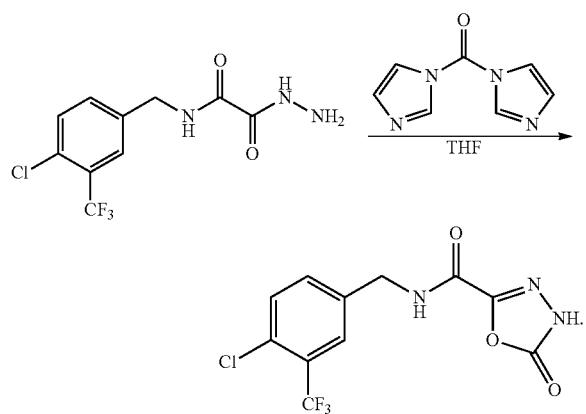

To a solution of compound C251 (0.125 g, 0.422 mmol) in 6 mL tetrahydrofuran was added 1,1'-carbonyldiimidazole (0.082 g, 0.506 mmol). The mixture was allowed to stir for 18 hr at room temperature, at which time the reaction was quenched with 1N HCl, taken up in 30 mL ethyl acetate, and washed with brine. The organic layer was dried, filtered, and concentrated in vacuo. The resulting residue was triturated with chloroform and filtered to provide 0.087 g (64%) of product (compound C285) as a solid.

Compounds C299 and C306 were prepared according to above procedure except that compound C282 and compound C305, respectively, were used in place of compound C251.

Example 2—Synthesis of Compounds of Formula IV

General Procedure B

Compounds of formula IV were synthesized according to the procedure described below and as shown in the following scheme:

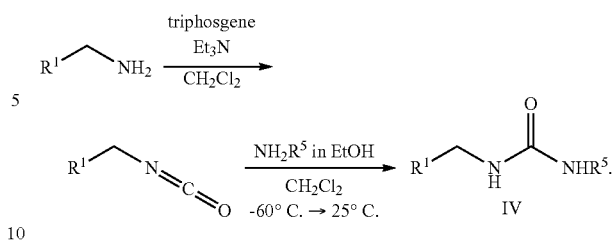

Step 1: To a 0° C. solution of triphosgene (1 equiv.) in dichloromethane, an appropriately-substituted amine (2.5 equiv.) was added dropwise with stirring. A solution of triethylamine (4.7 equiv.) in dichloromethane was then added. The mixture was allowed to stir for 5 min at 0° C., then overnight at 25° C. The reaction mixture was concentrated in vacuo, triturated with ethyl acetate, and filtered. The filtrate was concentrated in vacuo to provide the isocyanate product.

Step 2: An ethanolic solution of hydroxylamine (1 equiv.) was added to a −60° C. solution of an appropriately-substituted isocyanate (1 equiv.) in dry dichloromethane. The mixture was allowed to warm to room temperature and stir for 18 hr. The reaction solution was chilled in an ice bath and filtered cold. The filtrate was concentrated in vacuo and the resulting residue was taken up in ethyl acetate and washed with brine (1x). The organic layer was separated, dried, filtered, and concentrated in vacuo. The resulting residue was triturated with chloroform and filtered to provide compounds of formula IV.

Synthesis of 4-chloro-3-trifluoromethylbenzyl isocyanate

To a 0° C. solution of triphosgene (0.630 g, 2.12 mmol) in 10 mL dichloromethane, 4-chloro-3-trifluoromethylbenzyl amine (0.800 mL, 5.23 mmol) was added dropwise with stirring. A solution of triethylamine (1.39 mL, 10 mmol) in 5 mL dichloromethane was then added. A white precipitate formed immediately. The mixture was allowed to stir for 5 min at 0° C., then overnight at 25° C. The reaction mixture was concentrated in vacuo, triturated with ethyl acetate, and filtered. The filtrate was concentrated in vacuo to provide 1.19 g (97%) of 4-chloro-3-trifluoromethylbenzyl isocyanate as a clear oil.

Synthesis of 1-(4-chloro-3-(trifluoromethyl)benzyl)-3-hydroxyurea (compound C284)

An ethanolic hydroxylamine solution was prepared by addition at 0° C. of a solution of 25 mmol NaOH in 55 mL absolute ethanol to a stirring suspension of 25 mmol hydroxylamine hydrochloride in 60 mL of absolute ethanol. 8.9 mL of the ethanolic solution of hydroxylamine (1.93 mmol) was added to a −60° C. solution of 4-chloro-3-trifluoromethylbenzyl isocyanate (0.455 g, 1.93 mmol) in 10 mL dry dichloromethane. The mixture was allowed to warm to room temperature and stir for 18 hr. The reaction solution was chilled in an ice bath and filtered cold. The filtrate was concentrated in vacuo and the resulting residue was taken up in 30 mL ethyl acetate and washed with brine (1x). The organic layer was separated, dried, filtered, and concentrated in vacuo. The resulting residue was triturated with chloroform and filtered to provide 0.140 g (27%) of compound C284 as a white solid.

Example 3—Synthesis of Compounds of Formula V

General Procedure C

Compounds of formula V were synthesized according to the procedure described below and as shown in the following scheme:

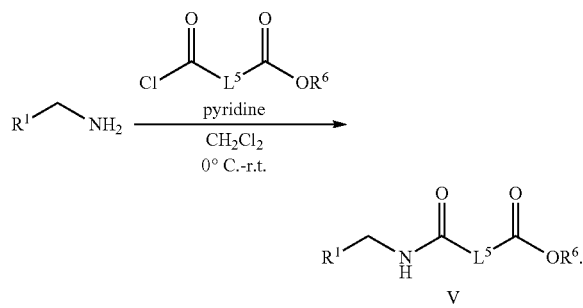

To a 0° C. solution of an appropriately-substituted amine (1 equiv.) and pyridine (3.7 equiv.) in dichloromethane, an appropriately-substituted chlorocarbonyl ester (1 equiv.) was added dropwise. The solution was removed from the ice bath and left to react for 30 minutes. The reaction mixture was washed with 0.2 N HCl (2×), saturated $NaHCO_3$ (2×), and brine (2×), and was then dried with $MgSO_4$, filtered and concentrated in vacuo to afford compounds of formula V.

Synthesis of ethyl 2-((4-chloro-3-(trifluoromethyl)benzyl)amino)-2-oxoacetate (compound C256)

Ethyl 2-((4-chloro-3-(trifluoromethyl)benzyl)amino)-2-oxoacetate (compound C256) was synthesized according to General Procedure C. To a 0° C. solution of 4-chloro-3-trifluoromethylbenzylamine (187 μL, 1.23 mmol) and pyridine (370 μL, 4.6 mmol) in dichloromethane (6 ml), ethyl 2-chloro-2-oxoacetate (170 μL, 1.25 mmol) was added dropwise. The solution was removed from the ice bath and left to react for 30 minutes. The reaction mixture was washed with 0.2 N HCl (2×), saturated $NaHCO_3$ (2×), and brine (2×), and was then dried with $MgSO_4$, filtered and concentrated in vacuo to afford 0.381 g of compound C256 as a white solid (74%). $^1H$ NMR ($CDCl_3$, 400 MHz) δ 7.48 (m, 3H), 4.53 (d, J=6.4 Hz, 2H), 4.35 (q, J=7.3 Hz, 6.9 Hz, 2H), 1.38 (t, J=6.9 Hz, 3H); $^{13}C$ NMR ($CDCl_3$, 100 MHz) δ 160.48, 156.87, 136.25, 132.48, 131.94, 131.85, 128.77 (q, J=31.5 Hz), 127.15 (q, J=4.8 Hz), 122.69 (q, J=271.7 Hz), 63.53, 42.89, 13.97.

The following compounds also were synthesized according to General Procedure C: C256, C259, C265, C267, C276, C277, C288.

General Procedure D

Carboxylic acids were synthesized according to the procedure described below and as shown in the following scheme:

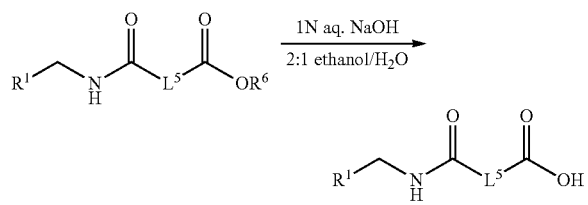

An appropriately-substituted ester (1 equiv.) was dissolved in a 2:1 solution of ethanol and water. 1.0 N NaOH (4 equiv.) was added to the reaction. After TLC analysis indicated that the starting material had been completely consumed, approximately 3 equivalents of 1.0 N HCl were used to quench the reaction. The reaction was cooled over ice as a precipitate formed and was then concentrated via filtration to afford the product carboxylic acid.

Synthesis of 2-((4-chloro-3-(trifluoromethyl)benzyl)amino)-2-oxoacetic acid (compound C309)

2-((4-Chloro-3-(trifluoromethyl)benzyl)amino)-2-oxoacetic acid (compound C309) was synthesized according to General Procedure D. Ethyl 2-((4-chloro-3-(trifluoromethyl)benzyl)amino)-2-oxoacetate (324.7 mg, 1.0 mmol) was dissolved in 12 ml of a 2:1 solution of ethanol and water. 4 ml of 1.0 N NaOH (4.0 mmol) was added to the reaction. After approximately 5 minutes, TLC analysis indicated that the starting material had been completely consumed. Approximately 3 equivalents of 1.0 N HCl (12 ml) were used to quench the reaction. The reaction was cooled over ice as a precipitate formed and was then concentrated via filtration to afford 143 mg (50%) of product as a white solid. $^1H$ NMR (DMSO-$d_6$, 400 MHz) δ 9.42 (t, J=6.0 Hz, 1H), 7.65 (d, J=8.3 Hz, 1H), 7.73 (d, J=1.8 Hz, 1H), 7.54 (dd, J=8.3 Hz, 1H), 4.34 (d, J=6.44 Hz, 2H); $^{13}C$ NMR (DMSO-$d_6$, 100 MHz) δ 162.38, 159.10, 139.26, 133.70, 132.15, 129.70 (q, J=1.9 Hz), 127.39 (q, J=4.8 Hz), 126.95 (q, J=30.5 Hz), 123.38 (q, J=271.7 Hz), 42.09. Percent Yield: 50.74%. HRMS, DART calcd. for $C_{10}H_8ClF_3NO_3$ 282.01448. found: 282.01169.

The following compound also was synthesized according to General Procedure D: C311.

Example 4—Synthesis of Compounds of Formula VI

General Procedure E

Compounds of formula VI were synthesized according to the procedure described below and as shown in the following scheme:

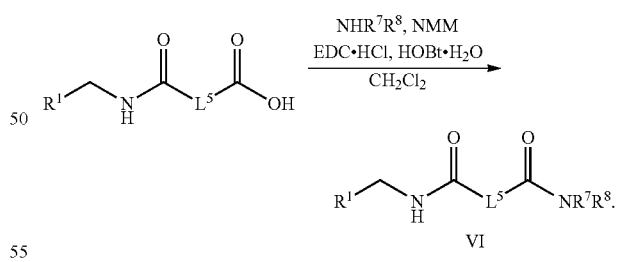

To a mixture of an appropriately-substituted carboxylic acid (1 equiv.), an appropriately-substituted amine (1.15 equiv.), 1-hydroxybenzotriazole [HOBt.$H_2O$] (1.15 equiv.), N-methylmorpholine [NMM] (1.15 equiv.) in methylene chloride, 1-ethyl-3-(3-dimethylaminopropyl) carbodiimide hydrochloride (EDC.HCl) (1.15 equiv.) was added and stirred for overnight. The resulting solution was diluted with ethyl acetate and washed with 1N HCl (2×), saturated $NaHCO_3$ (2×), and brine solution, dried with $MgSO_4$, filtered, and concentrated in vacuo to obtain compounds of formula VI.

Synthesis of N-(4-chloro-3-(trifluoromethyl)benzyl)-N'-methoxyoxalamide (compound C320)

N-(4-chloro-3-(trifluoromethyl)benzyl)-N'-methoxyoxalamide (compound C320) was synthesized according to General Procedure E. To a mixture of 2-((4-chloro-3-(trifluoromethyl)benzyl)amino)-2-oxoacetic acid (103.8 mg, 0.369 mmol), methoxyamine hydrochloride (36.9 mg, 0.426 mmol), 1-hydroxybenzotriazole [HOBt.H$_2$O] (65.8 mg, 0.426 mmol), N-methylmorpholine [NMM] (47.0 μl, 0.426 mmol) in methylene chloride (4 ml), 1-ethyl-3-(3-dimethylaminopropyl)carbodiimide hydrochloride (EDC.HCl) (82.4 mg, 0.426 mmol) was added and stirred for overnight. The resulting solution was diluted with ~20 ml of ethyl acetate and washed with 1N HCl (2×), saturated NaHCO$_3$ (2×), and brine solution, dried with MgSO$_4$, filtered, and concentrated in vacuo to obtain 0.0541 g (47.2%) of the product as a white solid. $^1$H NMR (DMSO-d$_6$, 400 MHz) δ 12.11 (bs, 1H), 9.45 (t, J=5.9 Hz, 1H), 7.73 (d, J=1.8 Hz, 1H), 7.65 (d, J=8.2 Hz, 1H), 7.53 (dd, J=6.8 Hz, J=1.4 Hz, 1H), 4.33 (d, J=6.4 Hz, 2H), 3.59 (s, 3H); $^{13}$C NMR (DMSO-d$_6$, 100 MHz) δ 160.17, 156.99, 139.26, 133.78, 132.16, 129.70, 127.52 (q, J=4.77 Hz), 126.92 (q, J=31.46 Hz), 223.38 (q, J=270.8 Hz), 63.67, 41.83; HRMS, DART calcd. for C$_{11}$H$_1$ClF$_3$N$_2$O$_3$ [M+H]$^+$ 311.04103. found: 311.03891.

The following compounds also were synthesized according to General Procedure E: C280, C300, C313, C314, C320, C323, C326, C328, C334, C342.

Example 5—Synthesis of Compounds of Formula VII

General Procedure F
Compounds of formula VII were synthesized according to the procedure described below and as shown in the following scheme:

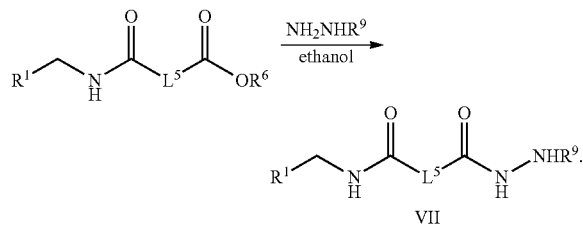

An appropriately-substituted compound of formula V prepared according to General Procedure C in Example 3 (1 equiv.) was dissolved in ethanol. An appropriately-substituted aqueous hydrazine (2 equiv.) was then added dropwise. The mixture was allowed to stir at room temperature for 48 hours. The solution was filtered, which afforded compounds of formula VII.

Synthesis of Compound C301

Compound C301 was synthesized according to General Procedure F. Ethyl 2-(2,3-dichlorobenzylamino)-2-oxoacetate (88.5 mg, 0.32 mmol, according to General Procedure C) was dissolved in 5 mL ethanol. 50% aqueous hydrazine hydrate (41 μL, 0.64 mmol) was then added dropwise. The mixture was allowed to stir at room temperature for 48 hours. The solution was filtered, which afforded 0.2045 g (quantitative yield) of product as a white solid. $^1$H-NMR (DMSO-d$_6$, 400 MHz) δ 10.06 (bs, 1H), 9.29 (t, J=6.0 Hz, 1H), 7.52 (dd, J=1.4, 7.8 Hz, 1H), 7.31 (t, J=7.8 Hz, 1H), 7.17 (dd, J=1.4, 7.8 Hz, 1H), 4.52 (bs, 2H), 4.38 (d, J=6.4 Hz, 2H); $^{13}$C-NMR (DMSO-d$_6$, 100 MHz) δ 160.67, 158.24, 138.79, 132.21, 130.29, 129.59, 128.59, 127.48, 41.31; HRMS, DART calcd. for C$_9$H$_{10}$N$_3$O$_2$Cl$_2$ [M+H$^+$] 262.01500. found: 262.00989.

The following compounds also were synthesized according to General Procedure F: C240, C241, C246, C248, C251, C255, C260, C261, C262, C263, C264, C266, C268, C278, C281, C282, C287, C289, C295, C296, C297, C301, C304, C305, C307, C310, C322, C336, C339, C340, C341, C362.

Example 6—Synthesis of Triazole Compounds of Formula XIII

General Procedure G
Compounds of formula XIII were synthesized according to the procedure described below and as shown in the following scheme:

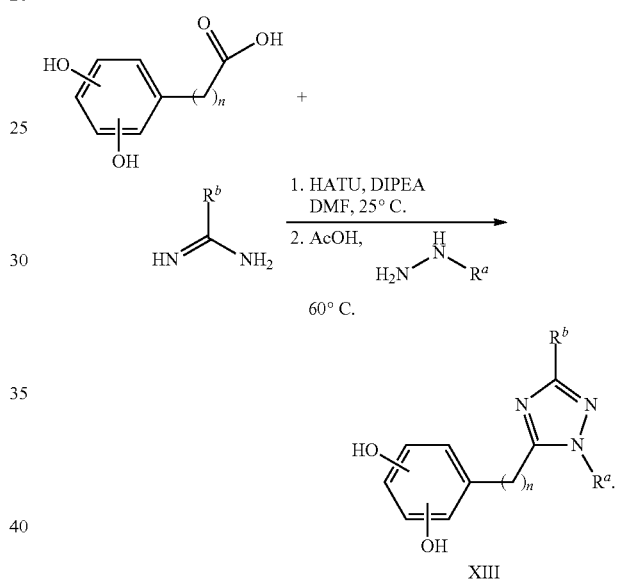

An appropriately-substituted carboxylic acid (1 equiv.), an appropriately-substituted amidine (1.4 equiv.), HATU (1.1 equiv.), diisopropylethylamine (2.8 equiv.), and DMF were added to a round bottom flask, stirred at 25° C. and monitored via TLC (20% methanol in CH$_2$Cl$_2$ with 2 drops of acetic acid) for consumption of acid and formation of intermediate. Upon consumption of the acid, an appropriately-substituted hydrazine (1.5 equiv.) and acetic acid (13.8 equiv.) were added, and the mixture was stirred at 80° C. and monitored via TLC (20% methanol in CH$_2$Cl$_2$) for formation of product. The mixture was taken up in 4:1 ethyl acetate/hexane, washed with saturated NaHCO$_3$ solution (3×), dried with MgSO$_4$, and concentrated by rotary evaporation. Flash chromatography (10% methanol in DCM) was used to isolate compounds of formula XIII. The above procedure was adapted from that described in Castanedo, G. M. et al., *J. Org. Chem.* 2011, 76, 1177-1179, which is incorporated by reference in its entirety.

Synthesis of 4-(1-(tert-butyl)-3-phenyl-1H-1,2,4-triazol-5-yl)benzene-1,2-diol (compound C201)

4-(1-(Tert-butyl)-3-phenyl-1H-1,2,4-triazol-5-yl)benzene-1,2-diol (compound C201) was synthesized according to General Procedure G. 3,4-Dihydroxybenzoic acid (265 mg, 1.72 mmol), benzamidine.HCl (292 mg, 2.43 mmol), HATU (707 mg, 1.86 mmol), diisopropylethylamine (850 µL, 4.86 mmol), and DMF (6 mL) were added to a 25 mL round bottom flask, stirred at 25° C. and monitored via TLC (20% methanol in CH$_2$Cl$_2$ with 2 drops of acetic acid) for consumption of acid and formation of intermediate. Upon consumption of the acid, t-butylhydrazine.HCl (189 mg, 2.55 mmol) and acetic acid (1 mL, 23.8 mmol) were added, and the mixture was stirred at 80° C. and monitored via TLC (20% methanol in CH$_2$Cl$_2$) for formation of product. The mixture was taken up in 100 mL of 4:1 ethyl acetate/hexane, washed with saturated NaHCO$_3$ solution (3×), dried with MgSO$_4$, and concentrated by rotary evaporation. Flash chromatography (10% methanol in DCM) was used to isolate 14.6 mg of product (3%). $^1$H NMR (CDCl$_3$, 400 MHz) δ 8.10 (dd, J=1.36, 8.24 Hz, 2H), 7.5-7.36 (m, 3H), 6.77 (d, J=1.84 Hz, 1H), 6.72 (d, J=7.8 Hz, 1H), 6.66 (dd, J=1.84, 7.76 Hz, 1H), 1.51 (s, 9H); $^{13}$C (CDCl$_3$, 100 MHz) δ 157.86, 155.02, 147.25, 143.99, 130.51, 129.37, 128.82, 128.71, 126.35, 121.92, 117.84, 114.90, 61.83, 30.76.

The following compounds also were synthesized according to General Procedure G: C208, C213, C214, C216, C220, C221, C222, C223.

Example 7—Synthesis of Thiazolidinedione Compounds of Formula XIV 3-(3-Bromobenzyl)thiazolidine-2,4-dione 3-(3-Bromobenzyl)thiazolidine-2,4-dione was synthesized according to the procedure described below and as shown in the following scheme:

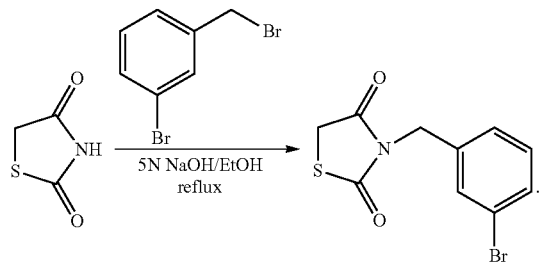

To a solution of 2,4-thiazolidinedione (0.50 g, 4.27 mmol) and 3-bromobenzyl bromide (1.03 g, 4.12 mmol) in 12.5 mL absolute ethanol, 1.27 mL 5N NaOH was added and the reaction mixture was heated to reflux. After 26 h the reaction was diluted with 15 mL H$_2$O and 20 mL ethyl acetate. The organic layer was washed with H$_2$O (3×15 mL) and brine (3×15 mL), dried over sodium sulfate, filtered, and concentrated in vacuo. The resulting residue was purified by flash column chromatography on silica (20:80 ethyl acetate: hexane) to provide 0.254 g (21%) of product.

Synthesis of (Z)-3-(3-bromobenzyl)-5-(3,4-dihydroxybenzylidene)thiazolidine-2,4-dione (compound C206)

(Z)-3-(3-bromobenzyl)-5-(3,4-dihydroxybenzylidene)thiazolidine-2,4-dione (compound C206) was synthesized according to the procedure described below and as shown in the following scheme:

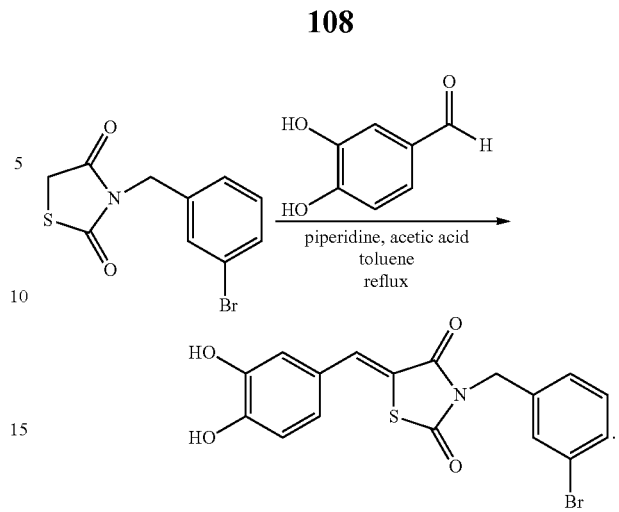

A solution of 3-(3-bromobenzyl)thiazolidine-2,4-dione (0.123 g, 0.43 mmol), 3,4-dihydroxybenzaldehyde (0.060 g, 0.43 mmol), piperidine (6 drops), acetic acid (6 drops), and 8 mL toluene was heated at reflux for 40 min. The reaction mixture was concentrated and purified by column chromatography (40:60 ethyl acetate:hexane) to provide 0.039 g (22%) of product (compound C206).

Compounds C199 and C203 were prepared according to above procedure except that 3-(benzyl)thiazolidine-2,4-dione and 3-(4-bromobenzyl)thiazolidine-2,4-dione, respectively, were used in place of 3-(3-bromobenzyl)thiazolidine-2,4-dione.

(Z)-5-(3,4-dihydroxybenzylidene)-3-((4'-(trifluoromethoxy)-[1,1'-biphenyl]-3-yl)methyl)thiazolidine-2,4-dione (compound C207)

(Z)-5-(3,4-dihydroxybenzylidene)-3-((4'-(trifluoromethoxy)-[1,1'-biphenyl]-3-yl)methyl)thiazolidine-2,4-dione (compound C207) was synthesized according to the procedure described below and as shown in the following scheme:

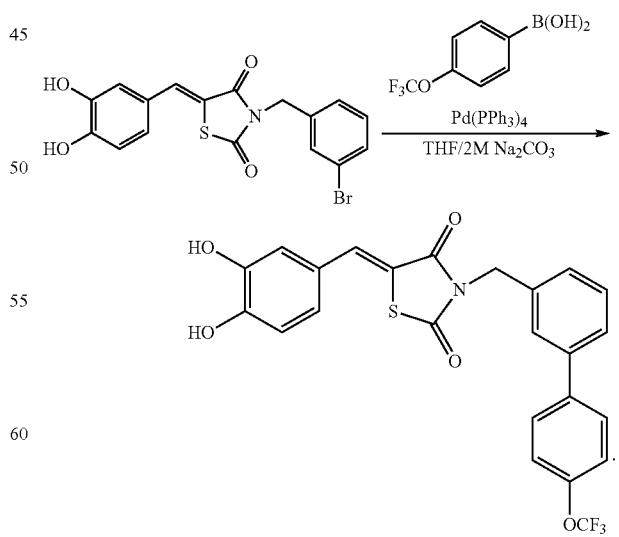

To a mixture of compound C206 (0.0365 g, 0.090 mmol), 4-trifluoromethoxy phenylboronic acid (0.028 g, 0.131 mmol), 1.3 mL tetrahydrofuran, and 0.15 mL of 2M Na₂CO₃ was added tetrakis(triphenylphosphine) palladium (0.0029 g, 0.0025 mmol). The mixture was heated to reflux for 3 h. The reaction mixture was diluted with 20 mL H₂O and acidified to pH 3 by dropwise addition of 1 N HCl. The solution was extracted with ethyl acetate (3×15 mL), and the combined organics were washed with H₂O (3×15 mL), dried over MgSO₄, filtered, and concentrated in vacuo. The resulted residue was recrystallized from ethanol to provide 0.034 g (78%) of product (compound C207).

Additional synthetic methods for obtaining PAI-1 inhibitors are disclosed in EP 166469 A1, which is incorporated by reference in its entirety.

Example 8—Synthesis of Oxindole Compounds of Formula XV

Synthesis of 5-(2-chloroacetyl)indolin-2-one 5-(2-Chloroacetyl)indolin-2-one was synthesized according to the procedure described below and as shown in the following scheme:

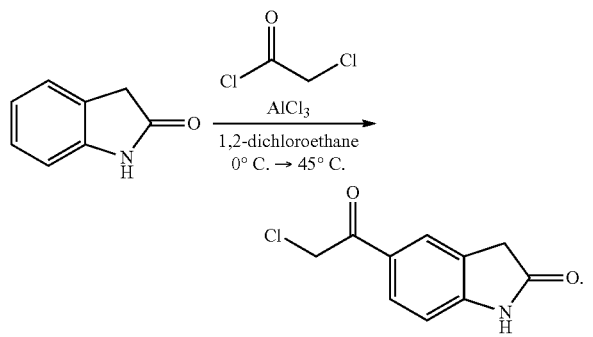

To a 0° C. round bottom flask containing a suspension of 7.53 g AlCl₃ (56.3 mmol) in 7 mL 1,2-dichloroethane, 3.6 mL (45.1 mmol) chloroacetyl chloride was added dropwise, resulting in a color change from yellow to dark red. The reaction was allowed to run for 1 hour after which a solution of 3.00 g oxindole (22.5 mmol) in 16 mL 1,2-dichloroethane was added. The reaction was allowed to run for an additional 2 hours at 0° C., and thereafter for another 3 hours at 45° C. The reaction was stopped by pouring into ice cold water, in which a tan precipitate formed immediately. The precipitate was filtered to provide 0.788 g (77%) of product as a beige solid.

Synthesis of 5,5'-(2,2'-(ethane-1,2-diylbis(azanediyl))bis(acetyl))bis(indolin-2-one) (compound C225)

5,5'-(2,2'-(Ethane-1,2-diylbis(azanediyl))bis(acetyl))bis(indolin-2-one) (compound C225) was synthesized according to the procedure described below and as shown in the following scheme:

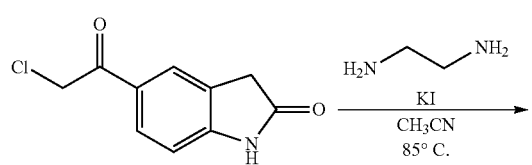

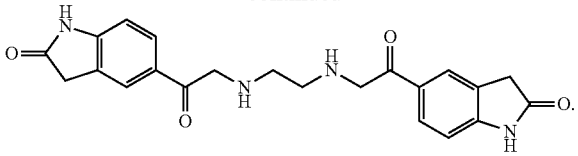

To a round bottom flask, 7.2 mL of acetonitrile, 320 mg potassium iodide (1.93 mmol), 250 mg potassium carbonate (1.79 mmol), and 24 µL of 1,2-ethylenediamine were added. Thereafter, 150 mg of 5-(2-chloroacetyl)indolin-2-one was added to the reaction flask and the reaction was allowed to run overnight (under nitrogen, with stirring) at reflux at 85° C. The reaction flask contents were concentrated in vacuo and transferred into a separatory funnel using ethyl acetate. The product was then washed with a saturated salt solution (3×). The organic layer was dried, filtered, and concentrated in vacuo to provide 0.291 g (6.6%) of product (compound C225).

Example 9—Synthesis of Oxindole Compounds of Formula XVII

Synthesis of 5-(2-(3,4-dimethoxyphenyl)thiazol-4-yl)indolin-2-one (C227)

5-(2-(3,4-dimethoxyphenyl)thiazol-4-yl)indolin-2-one (compound C227) was synthesized according to the procedure described below and as shown in the following scheme:

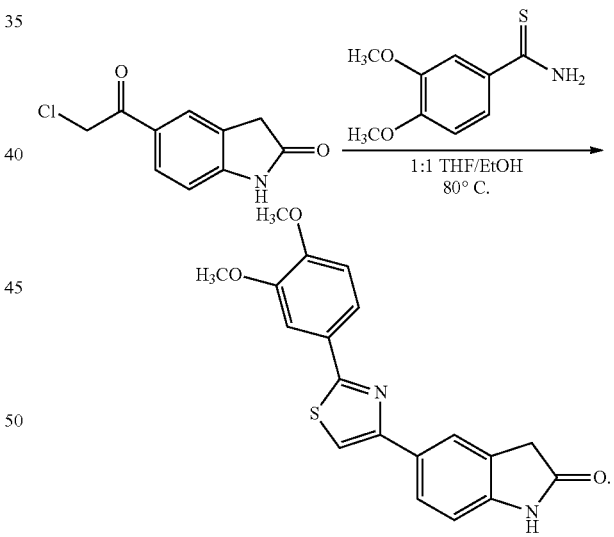

To a round bottom flask containing a solution of 60 mg (0.286 mmol) 5-(2-chloroacetyl)indolin-2-one, 1.5 mL THF, and 1.5 mL absolute ethanol was added 57 mg (0.286 mmol) 3,4-dimethoxythiobenazmide. The reaction was stirred overnight under nitrogen at reflux (80° C.). The reaction flask contents were then concentrated in vacuo and the resulting residue was purified by trituration in acetone to provide 50 mg (50%) of product (compound C227).

Compound C228 was prepared according to above procedure except that 3,4-dihydroxythiobenazmide was used in place of 3,4-dimethoxythiobenazmide.

Example 10—Synthesis of Oxindole Compounds of Formula XIX

Synthesis of 2-oxoindoline-5-sulfonyl chloride

2-Oxoindoline-5-sulfonyl chloride was synthesized according to the procedure described below and as shown in the following scheme:

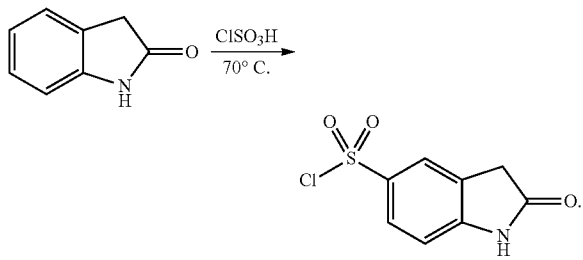

To a round bottom flask, 2.00 g oxindole (15.0 mmol) was added in small portions to 4.0 mL (61.2 mmol) chlorosulfonic acid at 30° C. while stirring. After all of the oxindole was added, the temperature was reduced to 25° C. and was left to react for 1.5 hours under nitrogen gas. The reaction heated to 70° C. for an additional 1.5 hr. The reaction mixture was then placed in an ice bath and quenched by dropwise addition of deionized water to the reaction mixture. Upon addition of water, a pink precipitate was formed, which was isolated by suction filtration to provide 1.47 g (42%) of product as a dusty rose solid.

Synthesis of
2-oxo-N-phenethylindoline-5-sulfonamide
(compound C229)

2-Oxo-N-phenethylindoline-5-sulfonamide (compound C229) was synthesized according to the procedure described below and as shown in the following scheme:

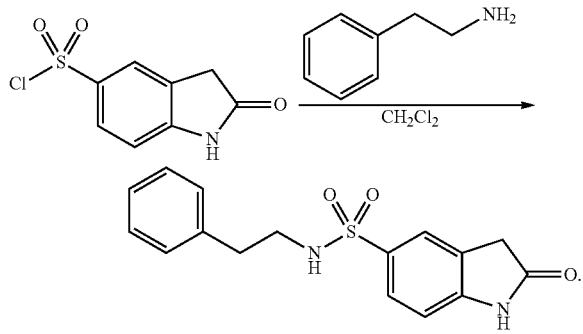

To a round bottom flask containing a solution of 100 mg 2-oxoindoline-5-sulfonyl chloride (0.432 mmol) in 9.5 mL methylene chloride, 0.119 mL (0.950 mmol) of phenethylamine was added. The reaction was stirred for 12 hours at room temperature under nitrogen gas. The reaction mixture was then diluted with 45 mL of ethyl acetate. This solution was washed with 1M HCl (3×15 mL) and a saturated salt solution (1×15 mL). The organic layer was collected and dried over magnesium sulfate, filtered, and concentrated in vacuo to provide 0.110 g (67%) of product (compound C229).

Example 11—Fluorometric PAI-1/uPA $IC_{50}$ Plate Assay at pH 7.4

To determine the efficacy of various synthesized compounds as PAI-1 inhibitors, a fluorometric plate assay was carried out to measure the half maximal inhibitory concentration ($IC_{50}$) of these compounds on recombinant active human PAI-1 in vitro. An $IC_{50}$ is a measure of the effectiveness of a compound in inhibiting biological or biochemical function. Stated another way, $IC_{50}$ represents the concentration of a drug that is required for 50% inhibition in vitro. The $IC_{50}$ of various compounds was measured using a fluorometric plate assay as set out below, and the results are shown in Tables 1 and 12.

PAI-1 inhibitor compounds were dissolved in DMSO to a final concentration of (10-50 mM), depending upon solubility. Compounds were then diluted in physiologic buffer (40 mM HEPES, 100 mM NaCl, 0.05% Tween-20, pH7.4) containing 10% DMSO and a dilution series (from 0 to 1000 uM depending on solubility) was prepared. 80 µL of compound was added per well to a 96-well black, opaque microplate in duplicate. 10 µL of 20 nM Recombinant active human PAI-1 (Molecular Innovations) in physiologic buffer (40 mM HEPES, 100 mM NaCl, 0.05% Tween-20, 10% DMSO, pH 7.4), or physiologic buffer with 15 mg/mL, or physiologic buffer with 10% human plasma, was added and the mixture was agitated for 15 minutes at room temperature. 10 µL of 25 nM uPA (Rheotromb®) was added to each reaction well and the plate was agitated for an additional 30 minutes at room temperature. Tripeptide aminomethylcoumarin Gly-Gly-Arg-AMC (Calbiochem) fluorogenic substrate (100 µL of 100 µM) was then added and residual uPA activity was determined based upon cleavage of this substrate. The rate of AMC release by uPA (fluorescence) was measured at an excitation wavelength of 370 nm and an emission wavelength of 440 nm. Controls included PAI-1 and uPA in the absence of compound and uPA alone. Percent PAI-1 inhibition was calculated using the following formula: [(uPA alone-uPA/PAI-1+ compound)/(uPA alone-PAI-1/uPA)]*100%. The $IC_{50}$ was calculated using Graphit ($IC_{50}$ 0-100%).

Example 12—Fluorometric PAI-1/uPA $I_{C50}$ Plate Assay at pH 7.8

To determine the efficacy of various synthesized compounds as PAI-1 inhibitors at pH 7.8, additional fluorometric plate assays were carried out to measure the half maximal inhibitory concentration ($IC_{50}$) of these compounds on recombinant active human PAI-1 in vitro. The $IC_{50}$ of each of these various compounds was measured using an assay as set out below, and the results are shown in Tables 3, 5, 7, 9, and 11.

PAI-1 inhibitor compounds were dissolved in DMSO to a final concentration of (10-50 mM), depending upon solubility. Compounds were then diluted in physiologic buffer (40 mM HEPES, 100 mM NaCl, 0.05% Tween-20, pH7.8) containing (10% DMSO and a dilution series (from 0 to 1000 uM depending on solubility) was prepared. 80 µL of compound was added per well to a 96-well black, opaque microplate in duplicate. 10 µL of 20 nM PAI-1 in physiologic buffer (pH 7.8) was added and the mixture was agitated for 15 minutes at room temperature. 10 µL of 25 nM uPA was added and the plate was agitated for an additional 30 minutes at room temperature. 100 µL of 100 µM fluorogenic, tripeptide aminomethylcoumarin Gly-Gly-Arg-AMC (Calbiochem) fluorogenic substrate was then added and residual uPA activity was determined based upon cleavage of this substrate. Fluorescence, as a measure of the rate of AMC release by uPA, was read at the following wavelengths; excitation 370 nm, emission 440 nm. Controls included PAI-1 and uPA in the absence of compound and uPA alone. Percent PAI-1 inhibition was calculated using the following formula: [(uPA alone-uPA/PAI-1+ compound)/(uPA alone-PAI-1/uPA)]*100%. The $IC_{50}$ was calculated using Graphit ($IC_{50}$ 0-100%).

Example 13—Fluorometric PAI-1/tPA $I_{C50}$ Plate Assay at pH 7.8

Additional fluorometric plate assays were carried out, as set out below, to determine the $IC_{50}$ of various synthesized compounds as PAI-1 inhibitors. Results are shown in Tables 3, 5, 7, 9, and 11.

PAI-1 inhibitor compounds were dissolved in DMSO to a final concentration of (10-50 mM), depending upon solubility. Compounds were then diluted in physiologic buffer (40 mM HEPES, 100 mM NaCl, 0.05% Tween-20, pH7.8) containing (10% DMSO and a dilution series (from 0 to 1000 µM depending on solubility) was prepared. 80 µL of compound was added per well to a 96-well black, opaque microplate in duplicate. 10 µL of 20 nM recombinant active human PAI-1 (Molecular Innovations) in physiologic buffer, as set out above, was added per well and the mixture was agitated for 15 minutes at room temperature. 10 uL of 25 nM human tissue type PA (tPA) (Activase® (alteplase), Genentech) was added per well and the plate was agitated for an additional 30 minutes at room temperature. Tissue type PA activity in each reaction mixture was determined by adding Phe-Gly-Arg-AMC fluorogenic substrate (100 µL of 100 µM) (Centerchem). The rate of AMC release by tPA was measured at an excitation wavelength of 370 nm and an emission wavelength of 440 nm. Controls included PAI-1 and tPA in the absence of compound and tPA alone. Percent PAI-1 inhibition was calculated using the following formula: [(tPA alone-tPA/PAI-1+ compound)/(tPA alone-PAI-1/tPA)]*100%. The IC50 is calculated using Graphit (IC50 0-100%).

Example 14—Fluorometric ATIII/αIIa $I_{C50}$ Plate Assay at pH 7.8

Additional fluorometric plate assays were carried out, as set out below, to determine the $IC_{50}$ of various synthesized compounds as PAI-1 inhibitors. Results are shown in Tables 3, 5, and 7.

Alpha-thrombin is an active enzyme, related to uPA or tPA. Alpha-thrombin is inhibited by the serpin ATIII, which is closely related to PAI-1. This assay was used therefore as a control in testing for specificity of the PAI-1 inhibitor compounds. Thus, any compound that is specific for inhibiting PAI-1 should not inhibit ATIII.

PAI-1 inhibitor compounds were dissolved in DMSO to a final concentration of (10-50 mM), depending upon solubility. Compounds were then diluted in physiologic buffer (40 mM HEPES, 100 mM NaCl, 0.05% Tween-20, pH7.8) containing (10% DMSO and a dilution series (from 0 to 1000 µM depending on solubility) was prepared. 80 µL of compound was added per well to a 96-well black, opaque microplate in duplicate. 10 µL of 20 nM recombinant active anti-thrombin III (ATIII) (Molecular Innovations), a PAI-1-related protein, in physiologic buffer, as set out above, was added and the mixture was agitated for 15 minutes at room temperature. 10 µL of 25 nM human α-Thrombin (αIIa) (Haematologic Technologies) was added to each reaction well and the plate was agitated for an additional 30 minutes at room temperature. 100 µL of 100 µM fluorogenic, tripeptide aminomethylcoumarin benzoyl Phe-Val-Arg-AMC substrate was then added and residual αIIa activity was determined based upon cleavage of this substrate. The rate of AMC release by αIIa was measured at an excitation wavelength of 370 nm and an emission wavelength of 440 nm. Controls included PAI-1 and αIIa in the absence of compound and αIIa alone. Percent PAI-1 inhibition is calculated using the following formula: [(αIIa alone-αIIa/PAI-1+ compound)/(αIIa alone-PAI-1/αIIa)]*100%. The IC50 is calculated using Graphit (IC50 0-100%).

The invention has been described in terms of particular embodiments found or proposed to comprise preferred modes for the practice of the invention. It will be appreciated by those of ordinary skill in the art that, in light of the disclosure, numerous modifications and changes can be made in the particular embodiments exemplified without departing from the intended scope of the invention. Therefore, it is intended that the appended claims cover all such equivalent variations which come within the scope of the invention as claimed.

What is claimed is:

1. A compound of formula I or a salt thereof:

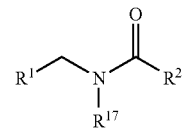

wherein:

$R^1$ is selected from the group consisting of dihalophenyl, trihalophenyl, fluoro(trifluoromethyl)phenyl, chloro(trifluoromethyl)phenyl, bromo(trifluoromethyl)phenyl, iodo(trifluoromethyl)phenyl, xylyl, fluorotolyl, chlorotolyl, bromotolyl, iodotolyl, fluoroxylyl, chloroxylyl, bromoxylyl, iodoxylyl, (trifluoromethoxy)phenyl, and cyanophenyl, each of which may be optionally substituted;

$R^2$ is -$L^5$-C(=O)$R^3$;

$R^3$ is NHNH$R^9$;

$R^9$ and $R^{17}$ are independently selected from the group consisting of H and $C_1$ to $C_{12}$ alkyl; and $L^5$ is selected from the group consisting of null, $C_1$ to $C_{12}$ alkylene, and $C_1$ to $C_{12}$ alkenylene.

2. The compound or salt of claim 1 having formula VII:

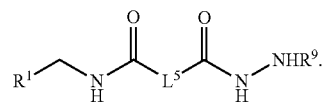

3. The compound or salt of claim 1, wherein $R^1$ is selected from the group consisting of:

4. The compound or salt of claim 1 having a formula selected from the group consisting of C251, C255, C261, C262, C268, C278, C282, C287, C301, C304, C305, C307, C336, C340, and C341:

-continued

C304
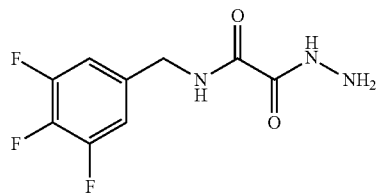

C305
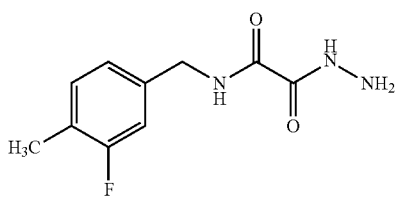

C307
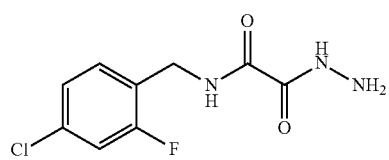

C336
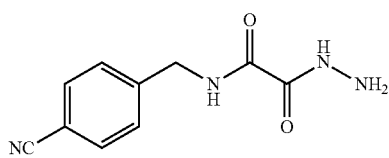

C340
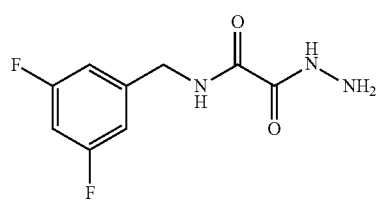

C341
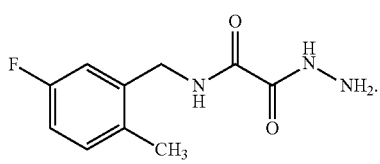

5. A composition comprising the compound or salt according to claim 1 and a pharmaceutically acceptable carrier.

6. A method of treating a disease or disorder associated with an elevated level of PAI-1 in a subject comprising administering an effective amount of a composition comprising the compound or salt according to claim 1 and a pharmaceutically acceptable carrier to decrease the elevated level of PAI-1 in the subject, wherein the disease or disorder is obesity, insulin resistance, a disease or disorder associated with dysregulation of lipid metabolism, a disease or disorder associated with an elevated level of VLDL or LDL, high cholesterol, fibrosis and fibrotic disease, cerebrovascular disease, fibrinolytic disorder, stroke, coronary heart disease, myocardial infarction, thrombosis, deep vein thrombosis, diabetes, or fibrinolytic impairment.

7. A method of modulating cholesterol, lipid clearance, and/or lipid uptake in a subject with an elevated level of PAI-1 comprising administering an effective amount of a composition comprising the compound or salt according to claim 1 and a pharmaceutically acceptable carrier in an amount effective to decrease the elevated level of PAI and modulate cholesterol, lipid clearance, and/or lipid uptake in the subject.

8. The method of claim 7, wherein the composition increases circulating high density lipoprotein (HDL) and/or decreases circulating very low density lipoprotein (VLDL) in the subject.

9. The method of claim 7, wherein the composition inhibits apolipoprotein E (ApoE) or apolipoprotein A (ApoA) binding to VLDL-R.

10. The method of claim 7, wherein the composition affects HDL or apolipoprotein E (ApoE) or apolipoprotein A (ApoA) binding to an ApoA receptor.

11. The method of claim 7, wherein the composition decreases PAI-1 binding to apolipoprotein E (ApoE), apolipoprotein A (ApoA), and/or VLDL.

12. The method of claim 7, wherein the composition binds to PAI-1 in the presence of vitronectin and/or urokinase type plasminogen activator (uPA).

* * * * *